United States Patent
Kim et al.

(10) Patent No.: US 10,960,182 B2
(45) Date of Patent: Mar. 30, 2021

(54) STEERABLE INTRA-LUMINAL MEDICAL DEVICE

(71) Applicant: BOARD OF REGENTS OF THE UNIVERSITY OF TEXAS SYSTEM, Austin, TX (US)

(72) Inventors: Daniel H. Kim, Houston, TX (US); Dong Suk Shin, Houston, TX (US); Viljar Palmre, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 61 days.

(21) Appl. No.: 15/562,690

(22) PCT Filed: Feb. 3, 2017

(86) PCT No.: PCT/US2017/016513
§ 371 (c)(1),
(2) Date: Sep. 28, 2017

(87) PCT Pub. No.: WO2017/136729
PCT Pub. Date: Aug. 10, 2017

(65) Prior Publication Data
US 2019/0192822 A1 Jun. 27, 2019

Related U.S. Application Data

(60) Provisional application No. 62/292,064, filed on Feb. 5, 2016.

(51) Int. Cl.
*A61M 25/01* (2006.01)
*A61L 29/04* (2006.01)
(Continued)

(52) U.S. Cl.
CPC ....... *A61M 25/0158* (2013.01); *A61L 29/041* (2013.01); *A61M 25/0009* (2013.01);
(Continued)

(58) Field of Classification Search
CPC .......... A61M 25/0158; A61M 25/0113; A61M 25/09041; A61M 2025/0058;
(Continued)

(56) References Cited

U.S. PATENT DOCUMENTS

| 5,174,168 A | 12/1992 | Takagi et al. |
| 5,337,732 A | 8/1994 | Grundfest et al. |

(Continued)

FOREIGN PATENT DOCUMENTS

| AU | 2001089246 A1 | 2/2002 |
| CN | 105307601 A | 2/2016 |

(Continued)

OTHER PUBLICATIONS

European Search Report, Application No. 17748266.8, dated Jan. 2, 2019, 9 pages.
(Continued)

*Primary Examiner* — Laura A Bouchelle
*Assistant Examiner* — Anh Bui
(74) *Attorney, Agent, or Firm* — Patterson + Sheridan, LLP

(57) ABSTRACT

The disclosure provides a flexible, narrow medical device (such as a micro-catheter or a guidewire) that is controllably moved and steered through lumens of a body. The medical device may include an electrically-actuatable bendable portion at a distal end, which may be provided by a polymer electrolyte layer, electrodes distributed about the polymer electrolyte layer, and electrical conduits coupled to the electrodes, such that the polymer electrolyte layer deforms asymmetrically in response to an electrical signal through (Continued)

one or more conduits. The disclosure further includes a controller for moving the device into and out of bodily lumens and for applying the electrical signal for steering the device. The device further includes methods of preparing the polymer electrolyte layer in tubular shape.

20 Claims, 21 Drawing Sheets

(51) Int. Cl.
  *A61M 25/09* (2006.01)
  *A61M 25/00* (2006.01)
(52) U.S. Cl.
  CPC .. *A61M 25/0113* (2013.01); *A61M 25/09041* (2013.01); *A61M 2025/0042* (2013.01); *A61M 2025/0058* (2013.01); *A61M 2025/09133* (2013.01); *A61M 2025/09175* (2013.01)
(58) Field of Classification Search
  CPC ......... A61M 2025/09133; A61M 2025/09175; A61M 2205/0283
  See application file for complete search history.

(56) References Cited

U.S. PATENT DOCUMENTS

| | | |
|---|---|---|
| 5,534,762 A | 7/1996 | Kim |
| 5,624,380 A | 4/1997 | Takayama et al. |
| 6,162,171 A | 12/2000 | Ng et al. |
| 6,244,644 B1 | 6/2001 | Lovchik et al. |
| 6,398,726 B1 | 6/2002 | Ramans et al. |
| 6,417,638 B1 | 7/2002 | Guy et al. |
| 6,468,203 B2 | 10/2002 | Belson |
| 6,554,844 B2 | 4/2003 | Lee et al. |
| 6,610,007 B2 | 8/2003 | Belson et al. |
| 6,679,836 B2 | 1/2004 | Couvillon, Jr. |
| 6,684,129 B2 | 1/2004 | Salisbury, Jr. et al. |
| 6,699,235 B2 | 3/2004 | Wallace et al. |
| 6,817,974 B2 | 11/2004 | Cooper et al. |
| 6,835,173 B2 | 12/2004 | Couvillon, Jr. |
| 6,858,005 B2 | 2/2005 | Ohline et al. |
| 6,869,396 B2 | 3/2005 | Belson |
| 6,879,315 B2 | 4/2005 | Guy et al. |
| 6,879,880 B2 | 4/2005 | Nowlin et al. |
| 6,890,297 B2 | 5/2005 | Belson |
| 6,949,106 B2 | 9/2005 | Brock et al. |
| 6,969,395 B2 | 11/2005 | Eskuri |
| 6,997,870 B2 | 2/2006 | Couvillon, Jr. |
| 7,044,907 B2 | 5/2006 | Belson |
| 7,063,671 B2 | 6/2006 | Couvillon, Jr. |
| 7,087,013 B2 | 8/2006 | Belson et al. |
| 7,097,615 B2 | 8/2006 | Banik et al. |
| 7,169,141 B2 | 1/2007 | Brock et al. |
| 7,199,052 B2 | 4/2007 | Cohen |
| 7,261,686 B2 | 8/2007 | Couvillon, Jr. |
| 7,320,700 B2 | 1/2008 | Cooper et al. |
| 7,411,576 B2 | 8/2008 | Massie et al. |
| 7,503,474 B2 | 3/2009 | Hillstead et al. |
| 7,543,518 B2 | 6/2009 | Buckingham et al. |
| 7,608,083 B2 | 10/2009 | Lee et al. |
| 7,615,066 B2 | 11/2009 | Danitz et al. |
| 7,631,834 B1 | 12/2009 | Johnson et al. |
| 7,666,135 B2 | 2/2010 | Couvillon, Jr. |
| 7,678,117 B2 | 3/2010 | Hinman et al. |
| 7,736,356 B2 | 6/2010 | Cooper et al. |
| 7,744,608 B2 | 6/2010 | Lee et al. |
| 7,744,622 B2 | 6/2010 | Brock et al. |
| RE41,475 E | 8/2010 | Grabover et al. |
| 7,766,896 B2 | 8/2010 | Komkven Volk et al. |
| 7,819,884 B2 | 10/2010 | Lee et al. |
| 7,854,738 B2 | 12/2010 | Lee et al. |
| 7,862,580 B2 | 1/2011 | Cooper et al. |
| 7,879,004 B2 | 2/2011 | Seibel et al. |
| 7,909,844 B2 | 3/2011 | Alkhatib et al. |
| 7,955,321 B2 | 6/2011 | Kishi et al. |
| 8,020,468 B2 | 9/2011 | Yang |
| 8,021,377 B2 | 9/2011 | Eskuri |
| 8,062,212 B2 | 11/2011 | Belson |
| 8,069,747 B2 | 12/2011 | Buckingham et al. |
| 8,083,669 B2 | 12/2011 | Murakami et al. |
| 8,092,371 B2 | 1/2012 | Miyamoto et al. |
| 8,114,097 B2 | 2/2012 | Brock et al. |
| 8,133,199 B2 | 3/2012 | Weber et al. |
| 8,142,421 B2 | 3/2012 | Cooper et al. |
| 8,182,418 B2 | 5/2012 | Durant et al. |
| 8,187,169 B2 | 5/2012 | Sugiyama et al. |
| 8,192,422 B2 | 6/2012 | Zubiate et al. |
| 8,206,429 B2 | 6/2012 | Gregorich et al. |
| 8,224,485 B2 | 7/2012 | Unsworth |
| 8,226,546 B2 | 7/2012 | Belson |
| 8,306,656 B1 | 11/2012 | Schaible et al. |
| 8,317,777 B2 | 11/2012 | Zubiate et al. |
| 8,323,297 B2 | 12/2012 | Hinman et al. |
| 8,328,714 B2 | 12/2012 | Couvillon, Jr. |
| 8,337,521 B2 | 12/2012 | Cooper et al. |
| 8,347,754 B1 | 1/2013 | Veltri et al. |
| 8,348,834 B2 | 1/2013 | Bakos |
| 8,365,633 B2 | 2/2013 | Simaan et al. |
| 8,366,604 B2 | 2/2013 | Konstorum |
| 8,414,598 B2 | 4/2013 | Brock et al. |
| 8,414,632 B2 | 4/2013 | Komkven Volk et al. |
| 8,439,828 B2 | 5/2013 | Dejima et al. |
| 8,444,547 B2 | 5/2013 | Miyamoto et al. |
| 8,483,880 B2 | 7/2013 | de la Rosa Tames et al. |
| 8,486,010 B2 | 7/2013 | Nomura |
| 8,517,921 B2 | 8/2013 | Tremaglio et al. |
| 8,517,924 B2 | 8/2013 | Banik et al. |
| 8,517,926 B2 | 8/2013 | Uchimura |
| 8,523,899 B2 | 9/2013 | Suzuki |
| 8,578,810 B2 | 11/2013 | Donhowe |
| 8,608,647 B2 | 12/2013 | Durant et al. |
| 8,617,054 B2 | 12/2013 | Miyamoto et al. |
| 8,641,602 B2 | 2/2014 | Belson |
| 8,644,988 B2 | 2/2014 | Prisco et al. |
| 8,663,097 B2 | 3/2014 | Arai |
| 8,672,837 B2 | 3/2014 | Roelle et al. |
| 8,679,004 B2 | 3/2014 | Konstorum |
| 8,708,892 B2 | 4/2014 | Sugiyama et al. |
| 8,715,270 B2 | 5/2014 | Weitzner et al. |
| 8,721,530 B2 | 5/2014 | Ohline et al. |
| 8,758,232 B2 | 6/2014 | Graham et al. |
| 8,768,509 B2 | 7/2014 | Unsworth |
| 8,771,260 B2 | 7/2014 | Conlon et al. |
| 8,777,843 B2 | 7/2014 | Banju et al. |
| 8,790,243 B2 | 7/2014 | Cooper et al. |
| 8,827,894 B2 | 9/2014 | Belson |
| 8,827,948 B2 | 9/2014 | Romo et al. |
| 8,834,354 B2 | 9/2014 | Belson |
| 8,834,390 B2 | 9/2014 | Couvillon, Jr. |
| 8,845,524 B2 | 9/2014 | Belson et al. |
| 8,845,622 B2 | 9/2014 | Paik et al. |
| 8,919,348 B2 | 12/2014 | Williams et al. |
| 8,920,970 B2 | 12/2014 | Sunkara et al. |
| 8,927,048 B2 | 1/2015 | Leeflang et al. |
| 8,986,196 B2 | 3/2015 | Larkin et al. |
| 9,055,961 B2 | 6/2015 | Manzo et al. |
| 9,060,678 B2 | 6/2015 | Larkin et al. |
| 9,060,796 B2 | 6/2015 | Seo |
| 9,147,825 B2 | 9/2015 | Kim et al. |
| 9,149,274 B2 | 10/2015 | Spivey et al. |
| 9,173,548 B2 | 11/2015 | Omori |
| 9,173,713 B2 | 11/2015 | Hart et al. |
| 9,192,447 B2 | 11/2015 | Choi et al. |
| 9,193,451 B2 | 11/2015 | Salyer |
| 9,205,560 B1 | 12/2015 | Edsinger et al. |
| 9,259,274 B2 | 2/2016 | Prisco |
| 9,289,266 B2 | 3/2016 | Weitzner et al. |
| 9,314,309 B2 | 4/2016 | Seo |
| 9,345,462 B2 | 5/2016 | Weitzner et al. |
| 9,358,031 B2 | 6/2016 | Manzo |
| 9,370,640 B2 | 6/2016 | Zhang et al. |
| 9,393,000 B2 | 7/2016 | Donhowe |

(56) References Cited

U.S. PATENT DOCUMENTS

| | | |
|---|---|---|
| 9,498,601 B2 | 11/2016 | Tanner et al. |
| 9,561,083 B2 | 2/2017 | Yu et al. |
| 9,724,162 B2 | 8/2017 | Crainich et al. |
| 2002/0120252 A1 | 8/2002 | Brock et al. |
| 2002/0133173 A1 | 9/2002 | Brock et al. |
| 2003/0006669 A1* | 1/2003 | Pei .................. A61M 5/142 310/309 |
| 2005/0096502 A1 | 5/2005 | Khalili |
| 2005/0250983 A1* | 11/2005 | Tremaglio ........... A61B 1/0052 600/101 |
| 2006/0058582 A1 | 3/2006 | Maahs et al. |
| 2006/0111618 A1* | 5/2006 | Couvillon, Jr. ... A61M 25/0105 600/152 |
| 2006/0261709 A1 | 11/2006 | Kato et al. |
| 2007/0027519 A1 | 2/2007 | Ortiz et al. |
| 2007/0112311 A1 | 5/2007 | Harding et al. |
| 2007/0123750 A1 | 5/2007 | Baumgartner et al. |
| 2007/0247033 A1 | 10/2007 | Eidenschink et al. |
| 2007/0249909 A1 | 10/2007 | Volk et al. |
| 2007/0250036 A1 | 10/2007 | Volk et al. |
| 2007/0299422 A1 | 12/2007 | Inganas et al. |
| 2007/0299427 A1 | 12/2007 | Yeung et al. |
| 2008/0051829 A1 | 2/2008 | Eidenschink et al. |
| 2008/0086081 A1 | 4/2008 | Eidenschink et al. |
| 2008/0177282 A1 | 7/2008 | Lee et al. |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0221391 A1 | 9/2008 | Weitzner et al. |
| 2008/0243175 A1 | 10/2008 | Moore et al. |
| 2009/0024086 A1 | 1/2009 | Zhang et al. |
| 2009/0082723 A1 | 3/2009 | Krogh et al. |
| 2009/0105645 A1 | 4/2009 | Kidd et al. |
| 2009/0157048 A1 | 6/2009 | Sutermeister et al. |
| 2009/0171160 A1 | 7/2009 | Ito et al. |
| 2009/0171161 A1 | 7/2009 | Ewers et al. |
| 2009/0259141 A1 | 10/2009 | Ewers et al. |
| 2009/0326319 A1 | 12/2009 | Takahashi et al. |
| 2010/0010309 A1 | 1/2010 | Kitagawa |
| 2010/0101346 A1 | 4/2010 | Johnson et al. |
| 2010/0113875 A1 | 5/2010 | Yi et al. |
| 2010/0300230 A1 | 12/2010 | Helmer |
| 2011/0040408 A1 | 2/2011 | De La Rosa Tames et al. |
| 2011/0092963 A1 | 4/2011 | Castro |
| 2011/0100146 A1 | 5/2011 | Feng |
| 2011/0251599 A1 | 10/2011 | Shellenberger et al. |
| 2011/0295063 A1 | 12/2011 | Umemoto et al. |
| 2012/0004502 A1 | 1/2012 | Weitzner et al. |
| 2012/0071863 A1 | 3/2012 | Lee et al. |
| 2012/0078053 A1 | 3/2012 | Phee et al. |
| 2012/0143174 A1 | 6/2012 | Choi et al. |
| 2012/0179097 A1 | 7/2012 | Cully et al. |
| 2012/0238952 A1 | 9/2012 | Mitchell et al. |
| 2012/0239032 A1 | 9/2012 | Zhang et al. |
| 2013/0035537 A1* | 2/2013 | Wallace ................. A61B 34/30 600/8 |
| 2013/0072913 A1 | 3/2013 | Yi et al. |
| 2013/0123692 A1 | 5/2013 | Zhang et al. |
| 2013/0199327 A1 | 8/2013 | Park et al. |
| 2013/0213170 A1 | 8/2013 | Kim et al. |
| 2013/0218005 A1 | 8/2013 | Desai et al. |
| 2013/0253424 A1* | 9/2013 | Kim .................... H01L 41/047 604/95.05 |
| 2013/0255410 A1 | 10/2013 | Lee et al. |
| 2013/0263424 A1 | 10/2013 | Giocastro |
| 2013/0281924 A1 | 10/2013 | Shellenberger |
| 2014/0005683 A1 | 1/2014 | Stand et al. |
| 2014/0012286 A1 | 1/2014 | Lee et al. |
| 2014/0046305 A1 | 2/2014 | Castro et al. |
| 2014/0107570 A1 | 4/2014 | Mitchell et al. |
| 2014/0142591 A1 | 5/2014 | Alvarez et al. |
| 2014/0142592 A1 | 5/2014 | Moon et al. |
| 2014/0163318 A1 | 6/2014 | Swanstrom |
| 2014/0163327 A1 | 6/2014 | Swanstrom |
| 2014/0180089 A1 | 6/2014 | Alpert et al. |
| 2014/0228631 A1 | 8/2014 | Kwak et al. |
| 2014/0243592 A1 | 8/2014 | Kato et al. |
| 2014/0257329 A1 | 9/2014 | Jang et al. |
| 2014/0257330 A1 | 9/2014 | Choi et al. |
| 2014/0276594 A1 | 9/2014 | Tanner et al. |
| 2014/0276940 A1 | 9/2014 | Seo |
| 2014/0288413 A1 | 9/2014 | Hwang et al. |
| 2014/0303643 A1 | 10/2014 | Ha et al. |
| 2014/0324070 A1 | 10/2014 | Min et al. |
| 2014/0336669 A1 | 11/2014 | Park |
| 2014/0379000 A1 | 12/2014 | Romo et al. |
| 2015/0018841 A1 | 1/2015 | Seo |
| 2015/0045812 A1 | 2/2015 | Seo |
| 2015/0066051 A1 | 3/2015 | Kwon et al. |
| 2015/0088060 A1 | 3/2015 | Wang et al. |
| 2015/0101442 A1 | 4/2015 | Romo |
| 2015/0105629 A1 | 4/2015 | Williams et al. |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Boguslcy et al. |
| 2015/0164596 A1 | 6/2015 | Romo et al. |
| 2015/0165163 A1 | 6/2015 | Alvarez et al. |
| 2015/0230869 A1 | 8/2015 | Shim et al. |
| 2015/0297865 A1 | 10/2015 | Hinman et al. |
| 2015/0335480 A1 | 11/2015 | Alvarez et al. |
| 2016/0001038 A1 | 1/2016 | Romo et al. |
| 2016/0151122 A1 | 6/2016 | Alvarez et al. |
| 2016/0151908 A1 | 6/2016 | Woodley et al. |
| 2016/0184032 A1 | 6/2016 | Romo et al. |
| 2016/0270865 A1 | 9/2016 | Landey et al. |
| 2016/0270866 A1 | 9/2016 | Yu et al. |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0331477 A1 | 11/2016 | Yu et al. |
| 2016/0331613 A1 | 11/2016 | Lee et al. |
| 2016/0374541 A1 | 12/2016 | Agrawal et al. |
| 2016/0374766 A1 | 12/2016 | Schuh |

FOREIGN PATENT DOCUMENTS

| | | |
|---|---|---|
| EP | 1876504 A1 | 1/2008 |
| EP | 1891880 A1 | 2/2008 |
| EP | 1 931 411 A2 | 6/2008 |
| JP | H0810336 A | 1/1996 |
| JP | 2005530558 A | 10/2005 |
| JP | 2007125256 A | 5/2007 |
| JP | 2016189884 A | 11/2016 |
| WO | 03/001986 A2 | 1/2003 |
| WO | 2003105671 A2 | 12/2003 |
| WO | 2004098060 A1 | 11/2004 |
| WO | 2006084744 A2 | 8/2006 |
| WO | 2010039387 A1 | 4/2010 |
| WO | 2011060317 A2 | 5/2011 |
| WO | 2012070838 A2 | 5/2012 |
| WO | 2012167043 A2 | 12/2012 |
| WO | 2012168936 A1 | 12/2012 |
| WO | 2013162206 A1 | 10/2013 |
| WO | 2014126653 A1 | 8/2014 |
| WO | 2015/057990 A1 | 4/2015 |
| WO | 2015/127250 A1 | 8/2015 |
| WO | 2015142290 A1 | 9/2015 |

OTHER PUBLICATIONS

Supplemental Partial European Search Report, EP17748276, dated Oct. 15, 2018, 18 pages.
Japanese Patent Application No. 2018-541109, Office Action dated Aug. 28, 2019, 13 pages.
European Patent Application No. 17748276.7, Extended Search Report dated Mar. 1, 2019, 20 pages.
International Search Report and Written Opinion dated May 17, 2017 for Application No. PCT/US2017/016513.
Chinese Patent Application No. 201780007564.X, Office Action dated May 22, 2020, 23 pages.

(56) References Cited

OTHER PUBLICATIONS

Japanese Patent Application No. 2018-541109, Office Action dated Jun. 2, 2020, 12 pages.
Australian Application No. 2017214568, Examination Report No. 1 dated Feb. 17, 2020, 5 pages.
Australian Application No. 2020203523, Examination Report No. 1 dated Jun. 29, 2020, 3 pages.
Australian Application No. 2020203478, Examination Report No. 1 dated Jul. 7, 2020, 3 pages.

\* cited by examiner

STEERABLE INTRA-LUMINAL MEDICAL DEVICE

CROSS REFERENCE TO RELATED APPLICATIONS

This application depends from and claims priority to U.S. Provisional Application No. 62/292,064 filed on Feb. 7, 2016, which is fully incorporated herein by reference in its entirety.

STATEMENT REGARDING FEDERALLY SPONSORED RESEARCH OR DEVELOPMENT

Not applicable.

BACKGROUND OF THE INVENTION

Field of the Invention

The invention relates to a steerable intraluminal medical device and, more particularly, to a flexible, narrow medical device (such as a micro-catheter or a guidewire) introduced into and controllably moved through lumens of a body. The medical device may include an electrically-actuatable bendable portion at a distal, leading end that can be selectively manipulated for steering the medical device to a targeted anatomical location within a body.

Discussion of the Related Art

Intraluminal medical devices have various structures depending on the location within the body and the methods of treatment using the devices. Intraluminal devices generally include of a very slender and flexible tube that can be inserted into and guided through a lumen such as an artery or a vein, or a bodily passageway such as a throat, a urethra, a bodily orifice or some other anatomical passage. Examples of such medical devices include syringes, endoscopes, catheters and micro-catheters, guide wires and other surgical instruments.

Some medical devices have a portion for being introduced into a body that generally comprises a flexible material that is easily bent by application of external force. In some medical devices, a distal, leading end (usually inserted first) may be selectively bent in a desired direction through manipulation of a steering mechanism by the user. The medical device can be inserted into a targeted lumen or bodily passage and moved to dispose a distal end of the medical device at a desired location in the body.

Surgical techniques for inserting and/or guiding a medical device into and/or through a lumen or passage in a body have been proposed in response to the rise in demand for minimally invasive surgical techniques. Many surgical techniques offer poor directional control or cumbersome manipulative components.

SUMMARY OF THE INVENTION

Embodiments of the steerable intraluminal medical device provide improved steering control and intra-body positioning of an actuation part (e.g., a micro-catheter or a guidewire) of a medical device wherein the actuation part is adapted to be introduced into a lumen or a bodily passage of a body and manipulated while being extended for movement into and through the lumen and/or bodily passage to dispose a distal end of the actuation part of the medical device at a desired anatomical location within the body. Embodiments of the medical device provide more precise control of movement and positioning of one or more manipulatable microsurgical components disposed at a distal, leading end of the actuation part of the medical device for performing a surgical procedure or other medical operation at the desired location within the body.

One embodiment of a medical device having an actuation part (e.g., a micro-catheter or a guidewire) for being moved into and/or through a lumen or a bodily passage comprises a slender, elongate and flexible portion having a distal end and a proximal end, an ionic electroactive polymer actuator comprising a polymer electrolyte layer disposed adjacent to the distal end of the elongate and flexible portion. The ionic electroactive polymer actuator, as will be discussed in greater detail below, is an actuator comprising a polymer electrolyte layer in which cations are free to migrate in response to an imposed electrical field. The electrical field is provided through energization of a plurality of angularly distributed electrodes disposed on the polymer electrolyte layer. The plurality of angularly distributed electrodes are one of embedded in, deposited on and secured against at least a portion of an exterior wall of the polymer electrolyte layer. Each of the plurality of electrodes may be connected to a source of electrical current through one or more electrically-conductive conduit such as, for example, a metal wire, being surrounded with the outer member and having a proximal end coupled to the source of electrical current and a distal end coupled to the electrode. Selective electrical energization of one or more of the plurality of electrodes causes the polymer electrolyte layer to deform as a result of contraction along a side or portion of the polymer electrolyte layer and/or swelling along a side or portion of the polymer electrolyte layer. It will be understood that cations within the polymer electrolyte layer will migrate towards an energized and anodic electrode, and away from an energized and cathodic electrode, while remaining within the matrix of the polymer electrolyte layer. This causes a portion adjacent to an energized anodic electrode to swell and a portion adjacent to an energized and cathodic electrode to contract, thereby causing the polymer electrolyte layer to bend. It will be understood that coordinated control of electrical signals delivered to the electrodes through electrically-conductive conduits can produce bending in an intended direction. In some embodiments, the plurality of electrodes may be further electrically connected to a sensing member to sense changes in the electrical signal at each of the plurality of electrodes. Accordingly, the sensing member may detect whether the ionic electroactive polymer actuator deformed or not.

In one embodiment of the medical device, the ionic electroactive polymer actuator may comprise a plurality of angularly distributed electrodes equi-angularly distributed about the exterior wall of the polymer electrolyte layer. In one embodiment of the medical device, the ionic electroactive polymer actuator may be included in a bendable portion at the distal end of an actuation part (e.g., a micro-catheter or a guidewire) of the medical device. For example, but not by way of limitation, the bendable portion of the medical device may, in one embodiment, comprise three angularly-distributed electrodes that are separated, at their centerlines, one from the others by about 120 degrees (2.094 radians). As another example, but not by way of limitation, the bendable portion of the medical device may comprise eight angularly-distributed electrodes that are separated, at their centerlines, by about 45 degrees (0.785 radians). It will be understood that each of the plurality of electrodes occupies a circumferential span about the exterior wall of the polymer electrolyte layer, and that the "angular separation" may therefore be stated in terms of the centerlines of the electrodes instead of in terms of the adjacent edges of the electrodes, which will be much closer to the adjacent edge of the adjacent electrode. In some embodiments of the medical device, the electrodes are spaced in a manner to provide a substantial gap intermediate adjacent electrodes.

In a bendable portion at the distal end of an actuation part of another embodiment of the medical device, the ionic electroactive polymer actuator is provided in which the plurality of electrodes circumferentially distributed about the exterior wall of a polymer electrolyte layer are, along with at least a portion of an adjacent inner member of the elongate and flexible portion, surrounded by an outer member, coating, sheath or other barrier having a bore in which at least a portion of the plurality of electrodes and at least a portion of the polymer electrolyte layer surrounded by the electrodes are together disposed. The outer member, or an exterior wall of the outer member, may comprise a low-friction, hydrophilic and/or lubricious material that promotes smooth sliding engagement between the elongate and flexible portion of the medical device and an interior wall of a lumen or a bodily passage into which the actuation part of the medical device is introduced and through which the elongate and flexible portion of the medical device is extended to position a distal end of the actuation part of the medical device at a targeted location within a body. The outer member may comprise one or more materials including, but not limited to, nylon, polyurethane and/or a thermoplastic elastomer such as, for example, PEBAX®, a polyether block amide material available from Arkema France Corporation of Colombes, France.

In one embodiment of the medical device, the plurality of electrically-conductive conduits that conduct electrical signals from a source of electricity to one or more of the plurality of electrodes to affect bending of the polymer electrolyte layer comprise a noble metal for superior chemical stability and corrosion resistance. For example, but not by way of limitation, the electrically-conductive conduits that deliver current to selected electrodes to actuate the polymer electrolyte layer may comprise highly conductive platinum, a platinum alloy, silver or a silver alloy, or they may comprise gold or a gold alloy which, in addition to being chemically stable and corrosion resistant, is malleable and can be advantageously formed into very slender electrically-conductive conduits with very low resistance to bending.

In a relaxed or un-energized state, the polymer electrolyte layer of the ionic electroactive polymer actuator remains in its original form.

One embodiment of the elongate and flexible portion of the medical device includes an elongate, flexible inner member having a distal end, a proximal end, a radially interior bore with an axis, and a radially exterior wall, at least one ionic electroactive polymer actuator comprising polymer electrolyte layer having a bore, the polymer electrolyte layer secured adjacent to the distal end of the inner member with the bore of the polymer electrolyte layer aligned with the bore of the inner member, a plurality of electrodes circumferentially distributed about the at least one polymer electrolyte layer, and a plurality of electrically-conductive conduits, each having a proximal end and a distal end coupled to at least one of the plurality of electrodes, and an elongate and flexible center wire having a proximal end, a distal end and a diameter therebetween that is smaller than the diameter of the bore of the inner member to enable the distal end of the center wire to be introduced into the bore of the inner member and to then be pushed through the bore of the inner member to position the distal end of the center wire adjacent to the distal end of the inner member, a radially compressed and resilient spring member coupled to the distal end of the center wire, the compressed spring member sized, in an uncompressed or expanded configuration, for exceeding the diameter of the bore of the inner member in an expanded configuration and for fitting within and being positioned in the bore of the inner member by the center wire in a compressed configuration, wherein the polymer electrolyte layer of the ionic electroactive polymer actuator deforms asymmetrically in response to the application of one or more electrical signals conducted from a source of electrical current (which may be further coupled to the proximal end of each electrically-conductive conduit) through at least one of the plurality of electrically-conductive conduits to at least one of the plurality of electrodes coupled to a distal end of the at least one of the plurality of electrically-conducting electrodes, and wherein the center wire can be used to position the spring member immediately adjacent to the distal end of the inner member with the inner member disposed within or immediately adjacent to an obstruction in a lumen into which the inner member is introduced, and wherein the spring member can be expanded from the compressed configuration to the expanded configuration to engage and grip the obstruction in the lumen by retracting the inner member while maintaining the center wire stationary relative to the inner member to cause the compressed spring member to be removed from the bore of the inner member and released from the radially compressed configuration to the expanded configuration within the obstruction to be gripped by the expanded spring member, thereby allowing the obstruction to be retrieved from the lumen by retrieving the center wire and the inner member together from the lumen. In one embodiment, the spring member is a coil spring having a plurality of coils aligned in a series. In another embodiment, the spring member includes a plurality of corrugated or sinusoidally shaped wires, each wire coupled at the apexes of the waves or peaks to the apexes of the waves or peaks of an adjacent wire to form a generally tubular or cylindrically shaped spring assembly. It will be understood that expandable spring elements of this type generally elongate as they radially expand from a radially compressed configuration to a radially expanded configuration.

One embodiment of the medical device includes an electrically insulating layer disposed within the bendable portion of the medical device. This insulating layer provides a flexible insulating boundary layer that contains but conforms to the polymer electrolyte layer as it deforms in response to an electrical field imposed by electrical signals conducted to the surrounding electrodes to provide advantageous steering of the medical device as it is positioned within a lumen or bodily passage.

The polymer electrolyte layer comprises an electrolyte (e.g., ionic liquid, but not limited to this) and a polymer selected from the group consisting of fluoropolymers and intrinsically conducting polymers. One embodiment of a method of preparing a tubular polymer electrolyte layer for use in providing an ionic electroactive polymer actuator in a bendable portion of a medical device comprises: providing a liquid dispersion of a base material selected from the group consisting of fluoropolymers and intrinsically conducting polymers, disposing the liquid dispersion on a substrate, curing the liquid dispersion of the selected base material to form a polymer film on the substrate, providing a mandrel, wrapping the polymer film onto the mandrel, and providing a heat-shrink tube, covering a portion of the mandrel wrapped in the polymer film with the heat shrink tube, and heating the heat-shrink tube to cause reflow the polymer film to form a tubular polymer electrolyte layer.

The polymer electrolyte layer may comprise, for example, but not by way of limitation, a polymer membrane containing a electrolyte (e.g., solvent such as, water or an ionic liquid). Alternately, the polymer electrolyte may comprise a porous polyvinylidene fluoride or polyvinylidene difluoride, a highly non-reactive thermoplastic fluoropolymer produced by the polymerization of vinylidene difluoride, and containing ionic liquid or salt water. Alternately, the polymer electrolyte may comprise a gel formed by polyvinylidene fluoride or polyvinylidene difluoride, propylene carbonate and an ionic liquid.

In one embodiment of the method of preparing a tubular polymer electrolyte layer for use in providing an ionic electroactive polymer actuator in a bendable portion of a medical device, the material selected to use in forming the base material comprising fluoropolymers and/or intrinsically conducting polymers. For example, the material may be, one of Nafion® and Flemion®, which are perfluorinated ionomers. In another embodiment of the method, the material selected to use in forming the base material comprising one of polyvinylidene difluoride (PVDF) and/or one of a co-polymer thereof, for example, one of polyvinylidene difluoride-co-chlorotrifluoroethylene (P(VDF-CTFE)) and polyvinylidene fluoride-co-hexafluoropropylene (P(VDF-HFP)), which are fluoropolymers. In yet another embodiment of the method, the material selected to use in forming the base material comprising an intrinsically conductive polymer (ICP), for example, one of polyaniline (PANI), polypyrrole (Ppy), poly(3,4-ethylenedioxythiophene) (PEDOT) and poly(p-phenylene sulfide)(PPS). In yet another embodiment of the method of preparing a tubular polymer electrolyte layer, the material selected to use in forming the base material comprises a combination of two or more of the above listed and described base materials.

One embodiment of the method of preparing a tubular polymer electrolyte layer includes the step of dissolving the base material in a volatile solvent to form the liquid dispersion. The volatile solvents that may be used for this step include, but are not limited to, acetates, alcohol, chloroform, ether, aliphatic hydrocarbons, aromatic hydrocarbons, chlorinated hydrocarbons and ketones.

One embodiment of the method of preparing a tubular polymer electrolyte layer includes the step of disposing the liquid dispersion of the selected base material onto a solid substrate comprising one of polytetrafluoroethylene (PTFE) or glass. However, other solid substrates having non-stick surfaces may be substituted.

A first example of an embodiment of the method of preparing a tubular polymer electrolyte layer includes preparing a liquid dispersion of Nafion® in 10 to 20 wt. % alcohol, disposing the liquid dispersion on a flat PTFE substrate using a doctors' blade method to form a thickness of 15-25 µm, curing the liquid dispersion on the substrate at 68° F. (20° C.), removing volatile solvents by thermal treatment at 176 to 248° F. (80 to 120° C.), rolling the resulting Nafion® film around a stainless steel mandrel rod having an outside diameter of 0.025" (0.635 mm) by manually rotating the mandrel while translating the mandrel across the substrate to roll-up the Nafion® film into a tubular shape having an interior diameter and a wall thickness.

The resulting interior diameter and wall thickness of the resulting polymer tubing depend on the mandrel size, the thickness of the Nafion® film and the number of times the mandrel can be wrapped with the Nafion® film during the rolling step. The mandrel with the rolled Nafion® film is fitted into a fluorinated ethylene-propylene (FEP) heat-shrink sleeve and then heated at the recovery temperature of the heat-shrink material 392 to 446° F. (200 to 230° C.). During heating, the layers of the rolled Nafion® film are reflowed into a single homogenous polymer layer. After cooling and removing the heat-shrink tube and mandrel, a Nafion® tube having a homogenous morphology without traces of rolled layers. The tolerance of the wall thickness of the prepared Nafion tube is similar to commercially extruded Nafion tubing (+/−10%) but is prepared without the need for commercial extrusion equipment that can require a large amount of space and equipment.

A second example of an embodiment of the method is to prepare a PVDF tube, including the steps of providing a plurality of Poly[(vinylidene difluoride)-co-(chlorotrifluoroethylene)] (P(VDF-CTFE)) pellets, dissolving the pellets in acetone by heating and stirring the pellets in the acetone at about 122° F. (50° C.) for 4 hours. The prepared dispersion is disposed on a flat PTFE substrate using the doctors' blade. The substrate and dispersion disposed thereon are cured at 68° F. (20° C.) for 30 minutes and the resulting film is then peeled from the PTFE substrate. The prepared P(VDF-CTFE) film is vacuum dried at 172° F. (80° C.) to remove the residual solvent. The formed PVDF film of 15-25 µm in thickness is rolled around a stainless steel mandrel rod having an outer diameter of 0.025 inches (0.635 mm) by manually rotating the mandrel and translating the mandrel across the film. The mandrel with the rolled PVDF film thereon is fitted into a heat-shrink polymer tube (e.g., fluorinated ethylene-propylene (FEP)) and heated at a recovery temperature of the heat-shrink material 392 to 446° F. (200 to 230° C.). The heating causes the layers of the rolled PVDF film to reflow into a single homogenous polymer tube wall. The heat-shrink tube is removed after cooling from the mandrel to remove the PVDF tube.

To further prepare an ionic electroactive polymer actuator, the prepared Nafion tube or PVDF tube may be further processed to deposit metal electrodes thereon (e.g., platinum or gold electrodes) using conventional methods such as an electrochemical process. Then, wires (e.g., gold wires) can be further integrated and embedded into the prepared metal electrodes using conducting paste or laser welding to serve as electrically-conductive conduits. Alternatively, in one embodiment, the prepared Nafion tube or PVDF tube may be further processed to deposit carbon-based electrodes using a new reflow method provided and explained in further detail below for use in providing a tubular ionic electroactive polymer actuator. Then, wires (such as gold wires) can be further integrated and embedded into the prepared carbon-based electrodes during the reflow method to serve as electrically-conductive conduits.

In one embodiment, a method of preparing a tubular ionic electroactive polymer actuator of a medical device by disposing carbon-based electrodes on a polymer electrolyte layer with a heat-shrink tube using reflow process is provided. The method may comprise: providing a polymer electrolyte layer having a radially exterior wall, providing a mixture of a carbon-based conductive powder in a volatile solvent, providing a plurality of electrically-conductive conduits, each having a proximal end and a distal end, disposing the mixture on the exterior wall of the polymer electrolyte layer to form a carbon electrode layer thereon, contacting the distal end of each electrically-conductive conduit to the carbon electrode layer, providing a heat-shrink tube, covering the polymer electrolyte layer and the carbon electrode layer thereon with the heat-shrink tube, and heating the heat-shrink tube to cause reflow of the polymer electrolyte layer to form the ionic electroactive polymer actuator. In another embodiment of the method of preparing a tubular ionic electroactive polymer actuator of a medical device, the polymer electrolyte layer may be further impregnated with an electrolyte. For example, the electrolyte may be an ionic liquid including, but not limited to, 1-ethyl-3-methylimidazolium tetrafluoroborate (EMI-BF4), 1-ethyl-3-methylimidazolium bis(trifluoromethylsulfonyl)imide (EMI-TFSI) or the combination thereof. In yet another embodiment of the method of preparing a tubular ionic electroactive polymer actuator of a medical device, a portion of the carbon electrode layer is further covered with one or more metal layer to increase the electrical conductivity of the obtained carbon-based electrodes. The metal layer herein may be, for example, but are not limited to a gold layer, a platinum layer or the combination thereof.

In other embodiment of the method of preparing a tubular ionic electroactive polymer actuator of a medical device, the carbon-based conductive powder may be carbide-derived carbon, carbon nanotube, carbon aerogel, graphene, or the combination thereof. In some embodiments, the carbon-based conductive powder may optionally comprise fillers such as transition metal oxide powder, metal powder or the combination thereof. In some embodiments, the mixture of a carbon-based conductive powder is disposed on the exterior surface of the polymer electrolyte layer using brush coating or spray coating. In other embodiments, the carbon electrode layer is further micro-machined to form a plurality of electrodes after heating the heat-shrink tube.

In one embodiment of the medical device, an electrical controller is provided for controlling bending of the bendable portion by applying electrical signals to an ionic electroactive polymer actuator in the bendable portion. The electrical controller may be provided at the proximal end of the elongate, flexible portion and electrically connected to the electrically-conductive conduits for selectively controlling the electrical charges carried by the electrically-conducting conduits and imparted to the plurality of electrodes to manipulate the at least one ionic electroactive polymer actuator of the medical device. In another embodiment, the electrical controller may be further instructed by a master controller. The master controller may comprise a manipulatable control member for inputting the bending control signals to the at least one ionic electroactive polymer actuator for providing two degrees of freedom of bending through the electrical controller.

To steerably control the medical device, in some embodiments, the medical device further comprises a driving assembly for moving the medical device (e.g., the flexible, elongated member portion) lengthwise. The drive assembly includes: a first rotary drive member with a gripping surface, an adjacent second rotary drive member with a gripping surface disposed proximal to the gripping surface of the first rotary drive member, and at least one electrically powered motor coupled to controllably rotate at least one of the first rotary drive member and the second rotary drive member and wherein, the medical device is disposed intermediate and engaged by the gripping surface of the first rotary drive member and the gripping surface of the adjacent second rotary drive member so that rotation of one of the first rotary drive member and the second rotary drive member axially moves the medical device. In one embodiment of steerably controlling the medical device, clockwise rotation of the first rotary drive member and counterclockwise rotation of the adjacent second rotary drive member moves the medical device in a first direction; and counterclockwise rotation of the first rotary drive member and clockwise rotation of the adjacent second rotary drive member moves the medical device in a second direction opposite to the first direction. In another embodiment, the driving assembly may be also further instructed by the master controller that comprise a manipulatable control member for inputting advance and retract control signals to the drive assembly for providing one degree of freedom of translation. In some embodiments, the master controller may provide the bending control signals as well as the advance and retract signals.

In one embodiment of steerably controlling the medical device, the medical device may further comprise a case that includes: a first portion having a sealed interior portion containing the first rotary drive member, the second rotary drive member, a proximal port through which the medical device passes, a distal port through which the medical device passes, and an interior cavity for storing windings of the medical device; and wherein the case further includes a second portion supporting the motor. In another embodiment, the second portion of the case and the first portion of the case are adapted for being coupled one to the other to operatively engage the motor with at least one of the first rotary member and the second rotary member. In other embodiments, the first portion may be disposable, for example, after use and contamination by bodily fluids contacted by the medical device.

In one embodiment, for remotely controlling/positioning the medical device when being introduced into and moving through a lumen of a human body, the medical device may further comprise: a transmitter coupled to the master controller for transmitting a signal corresponding to the manipulation of the master controller; and a receiver electrically connected to the drive assembly and the electrical controller for receiving the signal transmitted by the transmitter to the drive assembly and/or the electrical controller to correspond to the manipulation of the controller.

BRIEF DESCRIPTION OF THE DRAWINGS

The appended illustrative drawings provide a further understanding of embodiments and are incorporated into and constitute a part of this application and, together with the written description, serve to explain the present invention. The appended drawings are briefly described as follows.

DETAILED DESCRIPTION OF THE PREFERRED EMBODIMENTS

Medical devices such as catheters or guidewires may be sufficiently slender for being inserted into a lumen such as an artery, a vein, a throat, an ear canal, a nasal passage, a urethra or any of a number of other lumens or bodily passages. These slender catheters (also referred to as microcatheters) and guidewires, enable physicians to perform non-invasive surgery requiring a substantially shortened recovery period by preventing the need for cutting a subject or a patient to provide local access for performing a surgical procedure or medical operation. As used herein, the terms "subject" or "patient" refer to the recipient of a medical intervention with the device. In certain aspects, the patient is a human patient. In other aspects, the patient is a companion, sporting, domestic or livestock animal.

e following paragraphs describe certain embodiments of medical devices that can be used to perform or to enable the performance of surgical operations using the same, and methods that can be used to enable the preparation of such medical devices for same. It will be understood that other embodiments of medical devices and methods are within the scope of the claims appended herein below, and the illustration of such embodiments is not limiting of the present invention.

Figure 1:
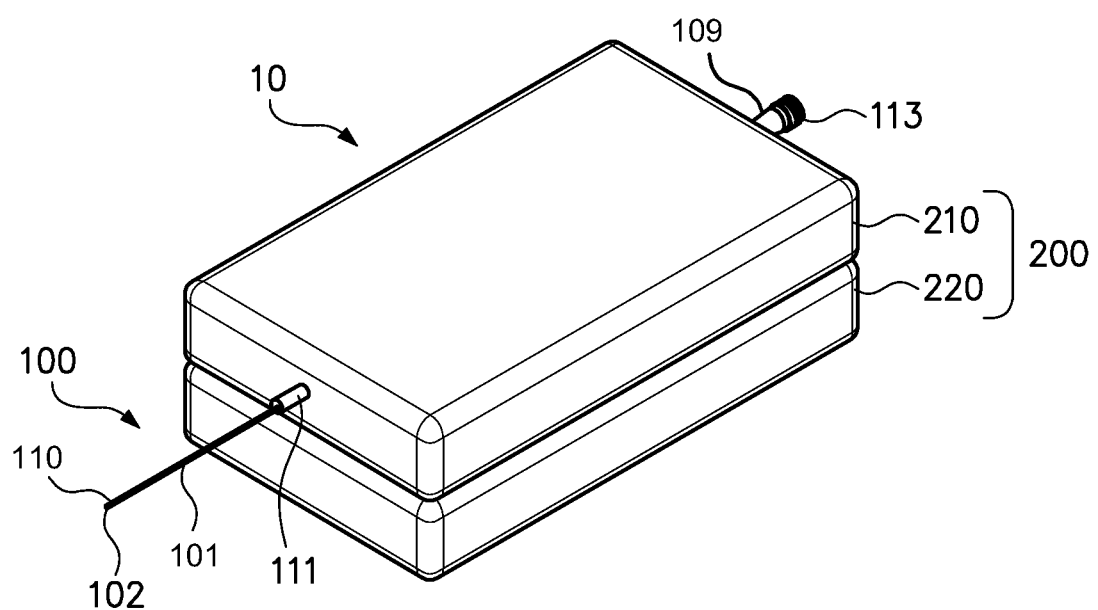
FIG. 1 is a perspective view showing one embodiment of a case for containing components used to controllably extend and retract an extendable actuation part of a medical device.

FIG. 1 is a perspective view showing one embodiment of a medical device 10 having a case 200 and an actuation part 100. The medical device 10 of FIG. 1 includes an upper case portion 210 and a lower case portion 220 of the case 200, the medical device 10 further including a flexible, elongate and slender actuation part 100 that comprises an elongate, flexible portion 101 to be extendable from the upper case portion 210 of the case 200 and a bendable portion 110 (FIG. 2) disposed at the distal end 102. The elongate, flexible portion 101 comprises an inner member 120 (FIG. 2) that is sufficiently slender to can be inserted into a lumen (not shown) of a body (not shown). Also the inner member 120 is sufficiently flexible and substantially axially incompressible so that it can be advanced through a lumen having a winding pathway by pushing or driving the elongate, flexible portion 101 of the actuation part 100 forward after a distal end 102 of the actuation part 100 is introduced into the lumen of the body (not shown). The actuation part 100 further includes a proximal end 109. The medical device 10 may be a micro-catheter having a bendable portion 110 that comprise an interior bore 140 (FIG. 2) to facilitate the movement of an elongate structure (not shown). In one embodiment, the elongate structure may be fed from the proximal end 109 through the interior bore 140 (FIG. 2) to and through the distal end 102 of the actuation part 100 of the medical device 10. Alternatively, the medical device 10 may be a guidewire having a bendable portion 110 without an interior bore 140 (e.g., FIG. 29).

Optionally, the proximal end 109 of the actuation part 100 may include a fastener such as, for example, threads 113, for use in securing a mating socket or other structure to the proximal end 109 of the actuation part 100. Optionally, the upper case portion 210 of the case 200 of the medical device 10 may include a guide barrel 211 for imparting a forward directional aspect to a distal portion 102 of the actuation part 100 that extends beyond the case 200.

Figure 2:
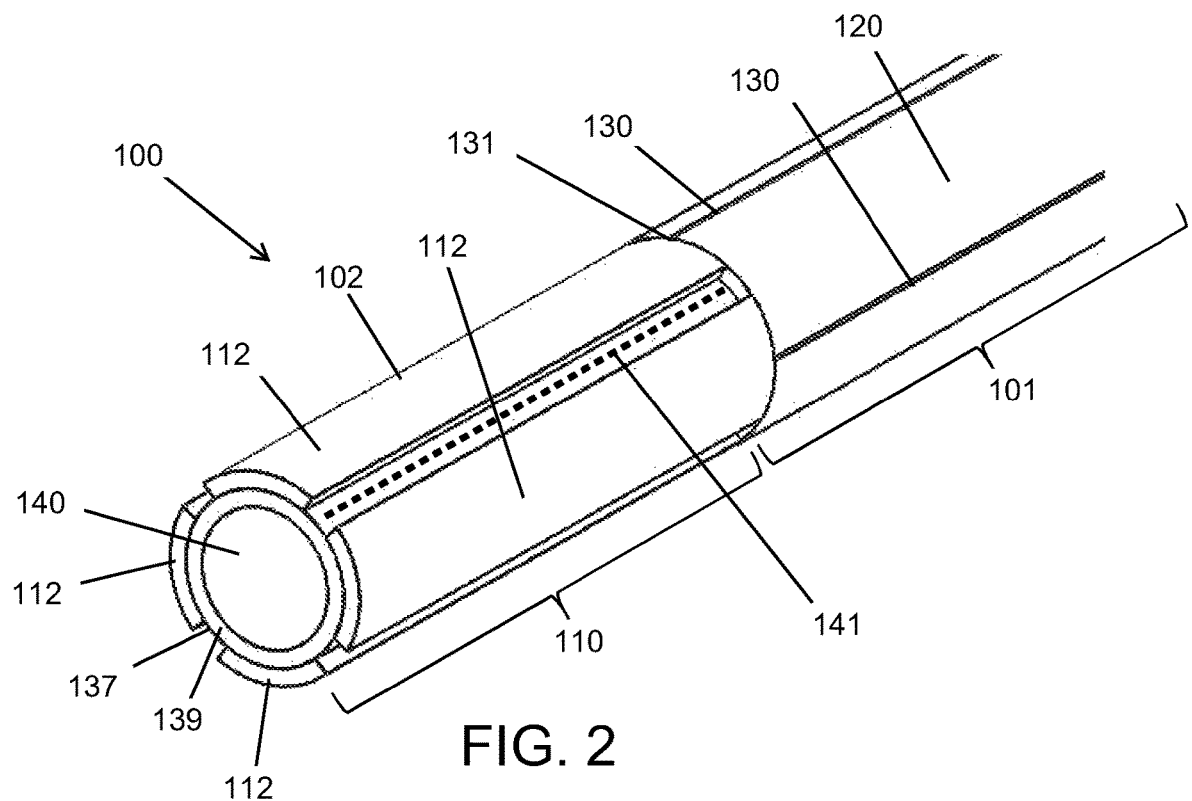
FIG. 2 is a perspective view of the elongate, flexible portion and a bendable portion disposed at the distal end of the actuation part of the embodiment of the medical device of FIG. 1.

FIG. 2 is a perspective view of the elongate, flexible portion 101 and a bendable portion 110 disposed at the distal end 102 of the actuation part 100 of the embodiment of the medical device 10 (e.g., a micro-catheter) of FIG. 1. The bendable portion 110 of the actuation part 100 includes an ionic electroactive polymer actuator comprising a polymer electrolyte layer 139 disposed adjacent to the inner member 120 of the elongate, flexible portion 101 and centrally to an angularly-distributed plurality of energizable electrodes 112. Each of the plurality of electrodes 112 that surrounds the exterior wall 137 of the polymer electrolyte layer 139 is connected to a distal end 131 of an electrically-conductive conduit 130 through which an electrical signal or current may be supplied to the connected electrode 112. The polymer electrolyte layer 139 includes a bore 140 through which other elongate structures may be inserted to position, control and/or actuate an effector or surgical tool or instrument disposed at the distal end of the elongate structure. The bore 140 of the polymer electrolyte layer 139 is, in a relaxed or de-energized condition, centered about an axis 141. The bendable portion 110 of FIG. 2 is illustrated in the straight mode. The bendable portion 110 can be selectively and controllably deformed to a bent mode by selective energization of one or more of the plurality of electrodes 112, as will be explained in further detail below.

In one embodiment of the medical device 10, the ionic electroactive polymer actuator of the bendable portion 110 of FIG. 2 is an ionic polymer-metal composite (IPMC) actuator. In one embodiment of the medical device 10, the ionic electroactive polymer actuator comprises a polymer electrolyte layer 139 made of a perfluorinated ionomer of Nafion® (Nafion® is available from E. I. DuPont de Nemours and Company) that have superior ion transport properties. Alternately, other embodiments of the ionic electroactive polymer actuator of the medical device 10 may include a polymer electrolyte layer 139 that comprises a perfluorinated ionomer such as Aciplex™ (available from Asahi Kasei Chemical Corp. of Tokyo, Japan), Flemion® (available from AGC Chemical Americas, Inc. of Exton, Pa., USA) or Fumapem® F-series (available from Fumatech BWT GmbH, Bietigheim-Bissingen, Federal Republic of Germany). In a preferred embodiment, the perfluorinated ionomer is Nafion®.

In one embodiment of the medical device 10, the electrically-conductive conduits 130 may comprise one of platinum, gold, carbon, alloys thereof or a combination thereof. In other embodiments, the material for electrodes 112 may comprise carbon, such as carbide-derived carbon, carbon nanotubes, a composite of carbide-derived carbon or ionomer, and a composite of carbon nanotube and ionomer. A method according to one embodiment of disposing the carbon-based electrodes 112 onto the polymer electrolyte layer 139 will be discussed herein below.

Each of the plurality of electrodes 112 is connected to a distal end 131 of an electrically-conductive conduit 130 through which an electrical signal may be applied to the electrode 112 to which the conduit 130 is connected, thereby causing metal cations within the polymer electrolyte layer 139 to move in a direction determined by the applied electrical signal. This cation migration produced by the applied electrical signal causes the polymer electrolyte layer 139 to swell in the portion of the polymer electrolyte layer 139 disposed proximal to the anode and to bend or warp in the direction of the remaining unswelled portion. As a result, the magnitude and the direction of bending deformations of the polymer electrolyte layer 139 of the ionic electroactive polymer actuator can be controlled by strategically selecting the electrodes 112 to energize and by adjusting the electrical signal applied through the electrically-conductive conduits 130 to the electrodes 112.

As shown in FIG. 2, the polymer electrolyte layer 139 includes a circular bore 140, and the plurality of electrodes 112 are angularly distributed about the circumference of the polymer electrolyte layer 139.

Figure 3:
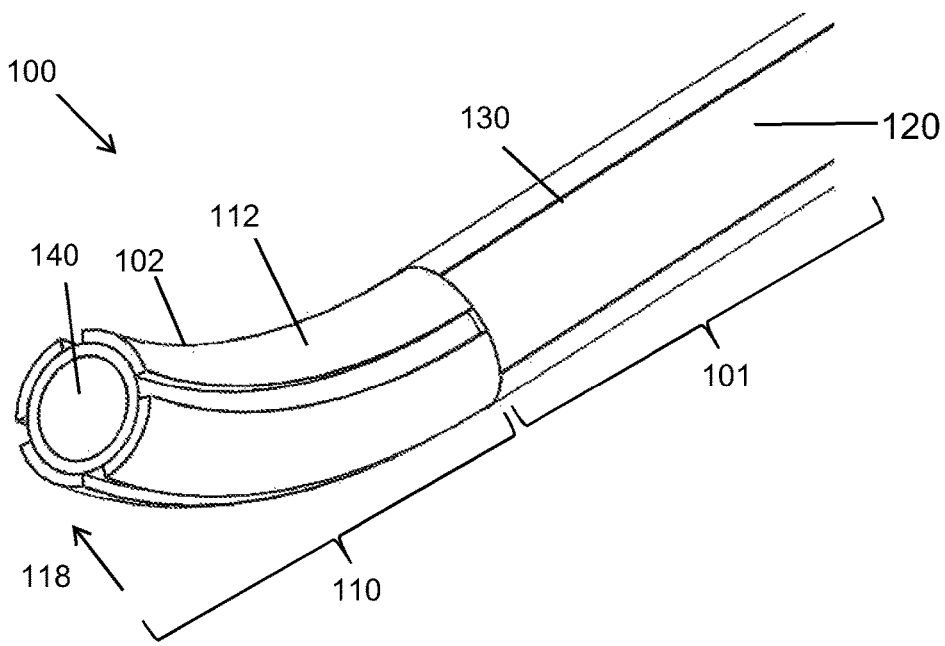
FIG. 3 is the perspective view of the distal, bendable portion at the distal end of the actuation part of FIG. 2 illustrating the bending mode.

FIG. 3 is a perspective view of the bendable portion 110 at the distal end 102 of the actuation part 100 of FIG. 2 illustrating the deformed or bending mode. The bendable portion 110 of the actuation part 100 of the medical device 10 is illustrated as having been actuated from the straight mode shown in FIG. 2 to the deformed or bent mode of FIG. 3 through the selective application of electrical signals to selected electrodes 112 to deform the polymer electrolyte layer 139. The energization of selected electrodes 112 causes the bendable portion 110 to be deformed from the straight mode to the bent mode by application of an external force indicated by arrow 118.

Alternately, in the event that the actuation part 100 is observed to be in a deformed mode in the absence of the application of one or more electrical signals to one or more of the plurality of the electrodes 112, the magnitude of the observed deflection can be used to determine the magnitude and direction of an external force applied to the actuation part 100 or, alternately, in the event that the application of a known current to the electrodes 112 fails to produce an anticipated deformation of the bendable portion 110 of the actuation part 100, the difference between the anticipated deformation and the actual deformation (if any) can be used as an indicator of the magnitude of an external force applied to the bendable portion 110 at the distal end 102 of the actuation part 100 of the medical device 10.

Figure 4B:
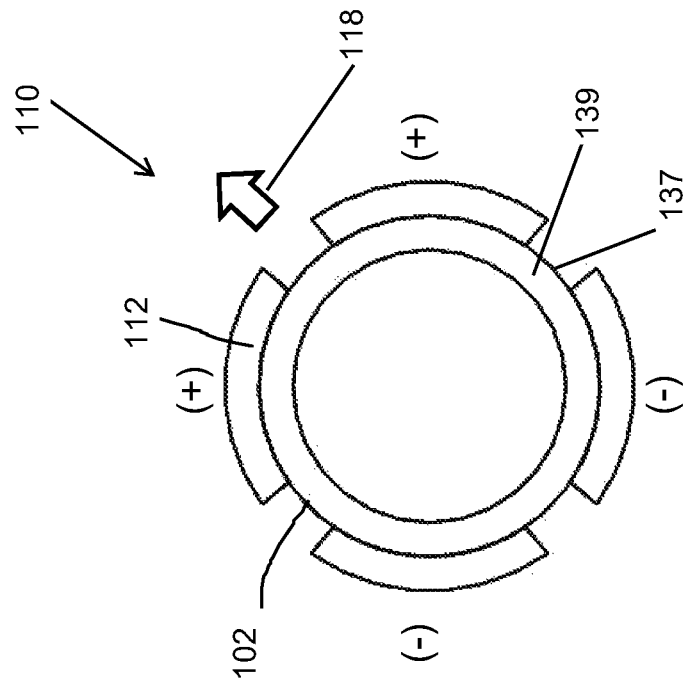
FIG. 4B is the cross-sectional view of the distal end of the bendable portion of FIG. 4A revealing a second selected set of four electrical signals applied to the angularly distributed electrodes disposed about the polymer electrolyte layer. The arrow indicates the direction of bend produced by the application of the illustrated electrical signals to the four individual electrodes.
Figure 4A:
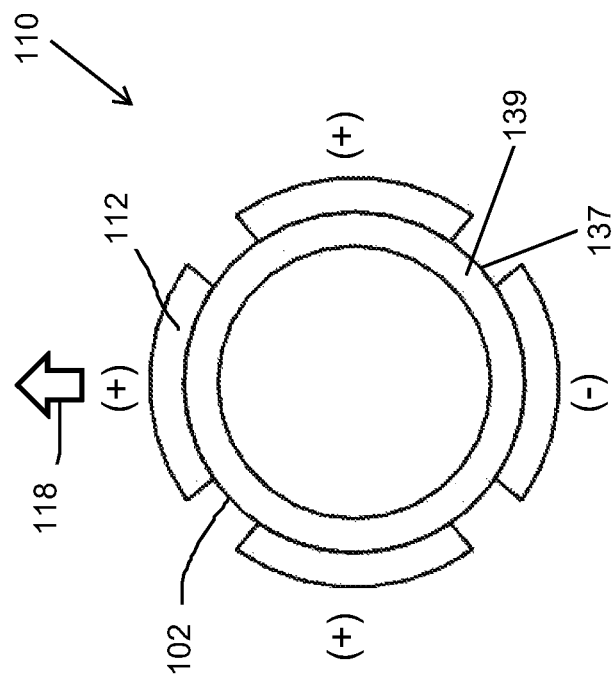
FIG. 4A is a cross-sectional view of the distal end of the bendable portion of FIGS. 2 and 3 illustrating a first selected set of four electrical signals applied to the four angularly-distributed electrodes disposed about the polymer electrolyte layer. The arrow indicates the direction of bend produced by the application of the illustrated set of electrical signals to the four individual electrodes.

FIG. 4A is a cross-sectional view of the distal end 102 of the bendable portion 110 of the actuation part 100 of FIGS. 2 and 3 illustrating a first selected set of four electrical signals applied to four circumferentially distributed electrodes 112 disposed about the exterior wall 137 of the polymer electrolyte layer 139. FIG. 4A illustrates the electrical signals that may be applied to the plurality of angularly distributed electrodes 112 to impart bending of the bendable portion 110 of the actuation part 100 in the direction of the arrow 118. It will be understood that the application of a positive charge on the electrodes 112 on the left and right sides of the bendable portion 110 of FIG. 4A, in addition application of a positive charge to the electrode 112 at the top of FIG. 4A, and further in addition to the application of a negative charge to the electrode 112 at the bottom of FIG. 4A, may result in a different amount of deformation than would occur as a result of the application of a positive charge on the electrode 112 at the top of FIG. 4A with a negative charge imparted to the remaining electrodes 112. It will be understood that the user may select the plurality of electrical signals that produces the deformation desired by the user.

FIG. 4B is the cross-sectional view of the distal end 102 of the bendable portion 110 of the extendable actuation part 100 of FIG. 4A revealing a second selected set of four electrical signals applied to the circumferentially distributed electrodes 112 disposed about the polymer electrolyte layer 139. FIG. 4B illustrates the application of a positive charge to the electrode 112 at the top of the bendable portion 110 of FIG. 4B and also to the electrode 112 at the right side of the bendable portion 110 of FIG. 4B, and FIG. 4B further illustrates the application of a negative charge to the electrode 112 at the bottom of FIG. 4B and also to the electrode 112 at the left side of FIG. 4B. The deformation of the polymer electrolyte layer 139 resulting from the application of these electrical charges is in the direction of the arrow 118.

It will be understood from FIGS. 4A and 4B that the distal end 102 of the bendable portion 110 of the actuation part 100 of the medical device 10 (e.g., a micro-catheter) can be bent in multiple directions and with varying degrees of deformation or deflection by strategic control of the electrical charges imparted to each of the individual electrodes 112. Although the embodiment illustrated in FIGS. 4A and 4B illustrates a bendable portion 110 including four electrodes 112, it will be understood that the bendable portion 110 of the actuation part 100 of the medical device 10 may include fewer than four or more than four electrodes 112, and such other embodiments will have differing deflection and deformation directional capacities.

Figure 5:
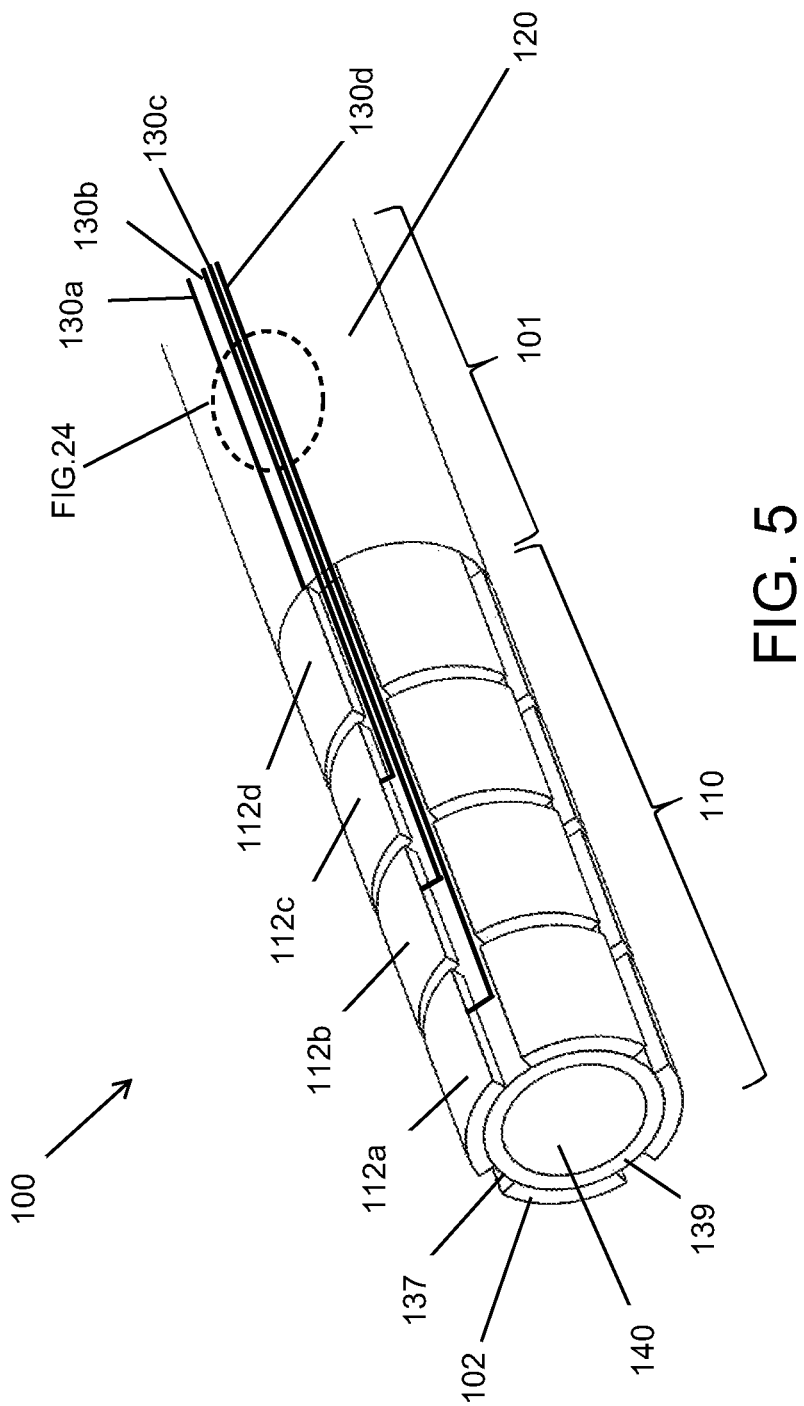
FIG. 5 is a perspective view of an alternative embodiment of a bendable portion and an elongate, flexible portion of an actuation part of a medical device of one embodiment having a plurality of individual electrodes separated both longitudinally and circumferentially. Each individual electrode is connected to an electrically-conductive conduit which provides an electrical signal to the electrode.

FIG. 5 is a perspective view of an alternative embodiment of a bendable portion 110 of an actuation part 100 of a medical device 10 (e.g., a micro-catheter). FIG. 5 illustrates how the magnitude and direction of deflection and deformation of the polymer electrolyte layer 139 may be tailored by disposing a plurality of electrodes 112a, 112b, 112c and 112d at varying positions along the length of the bendable portion 110 of the actuation part 100. By way of example and not by limitation, the bendable portion 110 of the actuation part 100 of FIG. 5 may include sixteen circumferentially and axially distributed electrodes 112a, 112b, 112c and 112d with the first set of four electrodes 112a disposed proximal to the distal end 102 of the bendable portion 110 of the actuation part 100, a second set of four electrodes 112b disposed adjacent to the first set of electrodes 112a, a third set of four electrodes 112c disposed adjacent to the second set of electrodes 112b, and a fourth set of electrodes 112d disposed adjacent to the third set of electrodes 112c. Each of the sixteen electrodes 112a, 112b, 112c and 112d (four sets) disposed on the bendable portion 110 of the actuation part 100 of the medical device 10 is connected to one of sixteen electrically-conductive conduits 130a, 130b, 130c and 130d, each for delivering an energizing current to the respective electrodes. The embodiment of the bendable portion 110 of the actuation part 100 illustrated in FIG. 5 results in enhanced deformation of the bendable portion 110 due to reduced resistance to bending intermediate the axially-spaced apart sets of electrodes 112.

Figure 6:
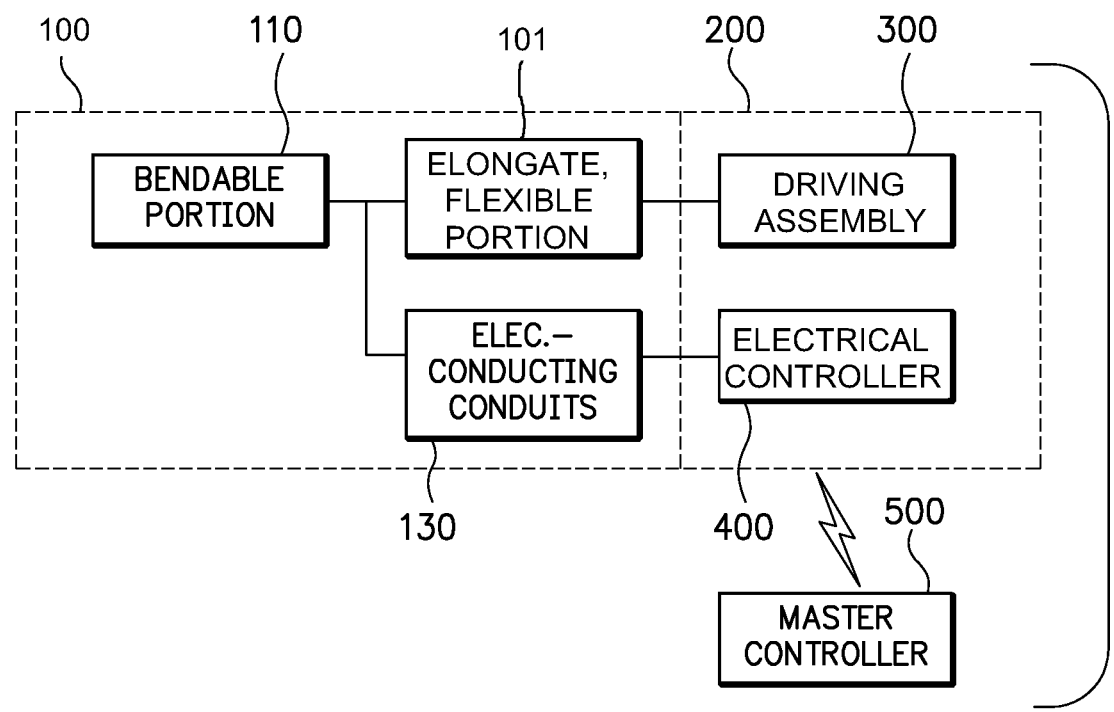
FIG. 6 is a block diagram schematically illustrating the systems and components that are used to use and control an embodiment of the medical device of FIGS. 1-4B.

FIG. 6 is a block diagram schematically illustrating the control system structure for the embodiment of the medical device 10 of FIGS. 1-4B. The medical device 10 herein may be a micro-catheter with an interior bore 140 (e.g., FIGS. 2-4B) or a guidewire without the interior bore 140 (e.g., FIG. 29). The medical device 10 includes an actuation part 100 adapted for insertion into a lumen or bodily passage and a case 200 with a drive assembly 300 (see FIGS. 8A-9) for advancing the elongate, flexible portion 101 and the bendable portion 110 of the actuation part 100 into and through a lumen or bodily passage and for selectively bending the bendable portion 110 at the distal end 102 of the actuation part 100. FIG. 6 illustrates the control interaction between the case 200, which contains both the drive assembly 300 for use in advancing the actuation part 100 into and through the lumen or bodily passage and an electrical controller 400 for selectively controlling the electrical charges carried by the electrically-conductive conduits 130 and imparted to the plurality of electrodes 112 to manipulate the bendable portion 110 of the actuation part 100 of the medical device 10. The electrical controller 400 may comprise a processor (not shown) that calculates the values of an electrical signal applied to the electrodes 112, in response to a user's input signals from the master controller 500. The master controller 500, which may be at a location other than the location of the patient, is shown wirelessly, telephonically and/or via the Internet, communicating with the case 200 of the medical device 10 in FIG. 6. It will be understood that, in one embodiment illustrated in FIG. 6, the master controller 500 of the medical device 10 may be in the presence of a surgeon (operator or user) that is remote from the patient (body) and the medical device 10. In that embodiment, the medical device 10 will include the master controller 500 or, alternately, an embodiment of the medical device 10 may not include a master controller 500 and may be used by a surgeon who is present in the operating room along with the patient and with the case 200. The master controller 500 may include, for example, a joystick for enabling the user to input the bending control signals to the electrodes 112 of the bendable portion 110 for providing two degrees of freedom of bending through the electrical controller 400, and a rolling input, such as, for example, a track ball or track wheel, for enabling the user to input advance and retract control signals to the drive assembly 300 for providing one degree of freedom of translation.

Figure 7:
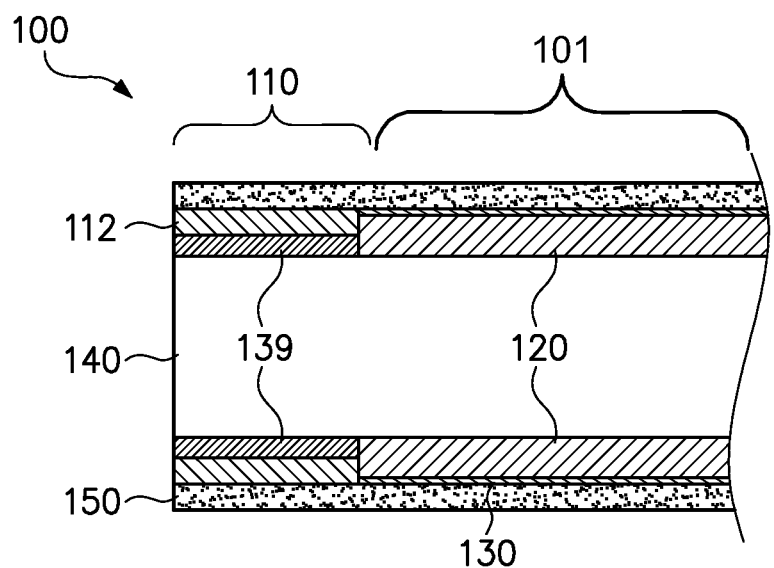
FIG. 7 is a lengthwise sectional view of a distal end of an extendable and steerable actuation part of an embodiment of a medical device, including a distal, bendable portion and an elongate, flexible portion.

FIG. 7 is a lengthwise sectional view of an extendable and steerable intraluminal actuation part 100 of an embodiment of a medical device 10 (e.g., a micro-catheter), including a distal, bendable portion 110 and an elongate, flexible portion 101.

FIG. 7 reveals the polymer electrolyte layer 139 and a plurality of surrounding electrodes 112. Each electrode 112 is electrically coupled to an electrically-conductive conduit 130. The bendable portion 110 is disposed adjacent to and aligned with the inner member 120 of the actuation part 100. The elongate, flexible portion 101 may further comprise a protective outer member 150 to surround the inner member 120, the electrically-conductive conduits 130, the electrodes 112 and the polymer electrolyte layer 139. The protective outer member 150 is adapted for low-friction sliding engagement with the interior wall of a lumen or other bodily passage into which the actuation part 100 of the medical device 10 may be introduced. In an embodiment of a micro-catheter of the medical device 10, the bore 140 provides a passage through which a surgical instrument such as, for example, an effector, a cutting implement, an imaging device (camera), a light source, a stint, a stint retriever or some other manipulatable surgical instrument can be passed and/or controlled by the user during surgery. Alternately, the bore 140 may form a fluid passage through which a drug, a radiation source or other material can be injected for precise placement in the body having the lumen or bodily passage. Although FIG. 7 illustrates an empty bore 140 in the elongate, flexible portion 101 of the actuation part 100, this bore 140 is intended for multiple uses. It will be further understood that a surgical instrument positioned, controlled or introduced through the bore 140 of the actuation part 100 may be connected to an effector, instrument, tool or other implement disposed adjacent to the bendable portion 100. It will be further understood that other devices for positioning a wire or other elongate slender device inserted into the bore 140 such as those described in relation to FIG. 6 may be used to position a wire or other device within the bore 140 without impairment of the function of devices used to position the actuation part 100 within the lumen.

Figure 8A:
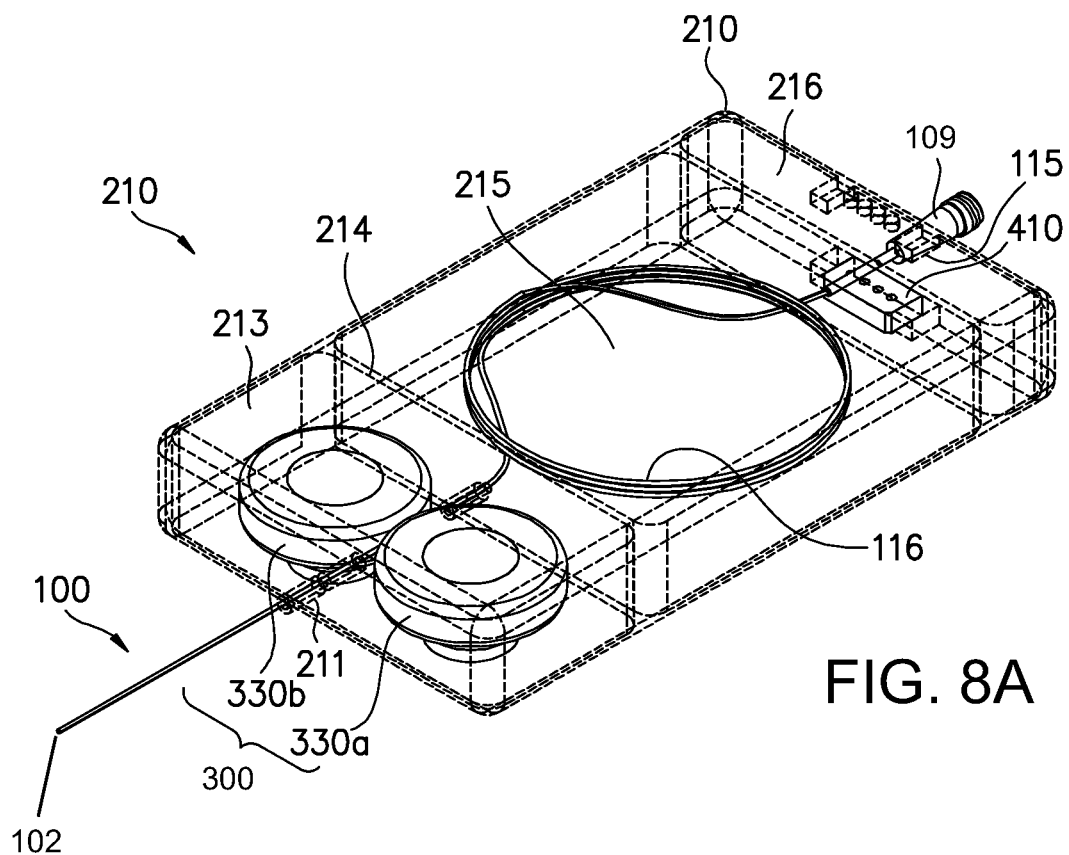
FIG. 8A is a perspective view of an upper case portion of the case of the embodiment of the medical device of FIG. 1 with the upper case portion of the case indicated in dotted lines to better reveal the components disposed therein.
Figure 8B:
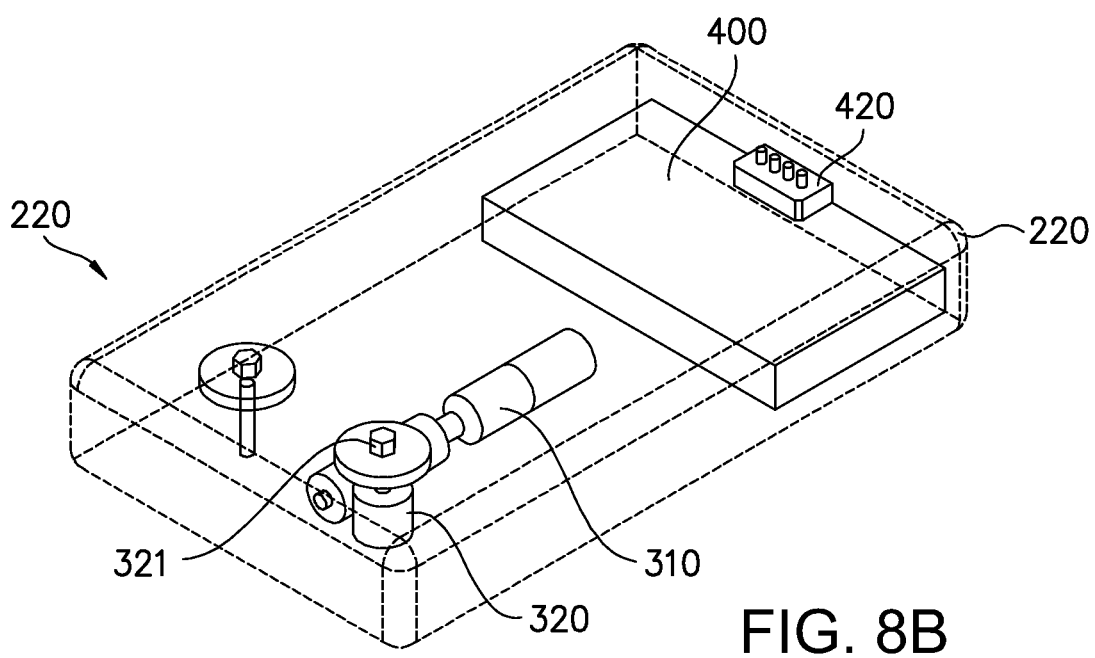
FIG. 8B is a perspective view of a lower case portion of the case of the embodiment of the medical device of FIG. 1 with the lower case portion of the case indicated in dotted lines to better reveal the components disposed therein.

FIGS. 8A and 8B together provide an exploded perspective view of an embodiment of a medical device 10. The medical device 10 herein may be a micro-catheter with an interior bore 140 (e.g., FIGS. 2-4B) or a guidewire without the interior bore 140 (e.g., FIG. 29).

FIG. 8A is a perspective view of an upper case portion 210 of the case 200 (see FIG. 1) of the embodiment of the medical device 10 of FIG. 1 with the upper case portion 210 indicated in dotted lines to better reveal the components of the medical device 10 disposed therein. In one embodiment of the medical device 10, the upper case portion 210 may be disposable because it includes the actuation part 100 that is inserted into, and contaminated by, the lumen or bodily passage of the patient into which it is inserted and from which it is later withdrawn. The upper case portion 210 illustrated in FIG. 8A includes a guide barrel 211 through which the distal end 102 of the actuation part 100 passes. The guide barrel 211 obscures an aperture (not shown) in the upper case portion 210 through which the actuation part 100 advances and withdraws. Similarly, the proximal end 109 of the actuation part 100 may pass through or may be fixedly disposed in an aperture 115. The proximal end 109 of the actuation part 100 may further include threads 113 (FIG. 1) for being paired with a mating socket or connection associated with a surgical instrument or tool. A cavity 215 within the upper case portion 210 may be used to store windings 116 formed in the length of the actuation part 100. The windings 116 of the actuation part 100 do not include the bendable portion 110, but do include the electrically-conductive conduits 130 and the inner member 120 (e.g., FIG. 7), both components of the actuation part 100 that are used to supply, position and control the components that are part of or adjacent to the bendable portion 110. The upper case portion 210 of FIG. 8A further includes a drive assembly 300 including a first rotary drive member 330a and an adjacent second rotary drive member 330b. The actuation part 100 is shown passing intermediate the first rotary drive member 330a and an adjacent second rotary drive member 330b. It will be understood that clockwise rotation of the first rotary drive member 330a and counterclockwise rotation of the adjacent second rotary drive member 330b will withdraw the actuation part 100 from the lumen or bodily passage of the patient and into the case 200, and counter-clockwise rotation of the first rotary drive member 330a and clockwise rotation of the adjacent second rotary drive member 330b will advance the actuation part 100 from the case 200 and into a lumen or bodily passage of the patient into which the distal end 102 of the actuation part 100 has been introduced.

FIG. 8B is a perspective view of a lower case portion 220 of the case 200 (see FIG. 1) of the embodiment of the medical device 10 of FIG. 1 with the lower case portion 220 indicated in dotted lines to better reveal the components of the medical device 10 disposed therein. In one embodiment of the medical device 10 in which the upper case portion 210 is disposable, the lower case portion 220 may be adapted for repeated and use, each use requiring pairing of a decontaminated lower case portion 220 with a new or refurbished upper case portion 210. The shape of the lower case portion 220 corresponds to the shape of the upper case portion 210 of FIG. 8A to facilitate the pairing of the lower case portion 220 with the upper case portion 210 to provide an assembled case 200. The lower case portion 220 of FIG. 8B includes components that have a low risk of contamination and those that are of a sufficient cost that they are useful for being refurbished, recycled and/or decontaminated after each use.

Components of the medical device 10 that are disposed in or on the lower case portion 220 are positioned to engage related components of the medical device 10 disposed in or on the upper case portion 210 to enable the coupling of these related components upon assembly of the upper case portion 210 of FIG. 8A and the lower case portion 220 of FIG. 8B. For example, but not by way of limitation, the drive assembly 300 of the upper case portion 210 of FIG. 8A that engages and moves the flexible actuation part 100 may also engage a motor 310 through an intermediate worm gear 320. The motor 310 drives the worm gear 320 to controllably rotate a drive fitting 321 positioned to be received into a corresponding drive socket (not shown) formed in the first rotary drive member 330a of the upper case portion 210 shown in FIG. 8A. In the embodiment shown in FIGS. 8A and 8B, an interface device 420 enables the case 200 of the medical device 10 to receive control signals, for example, signals to advance or withdraw the actuation part 100 using drive assembly 300 or to impart bending to the distal end 102 of the actuation part 100 using the bendable portion 110 from a master controller 500 (FIG. 9) used by a surgeon or operator (which includes for example other operators or users such as but not limited to medical practitioners, physicians, surgical technicians, nurses or assistants, veterinarians, etc.).

Figure 9:
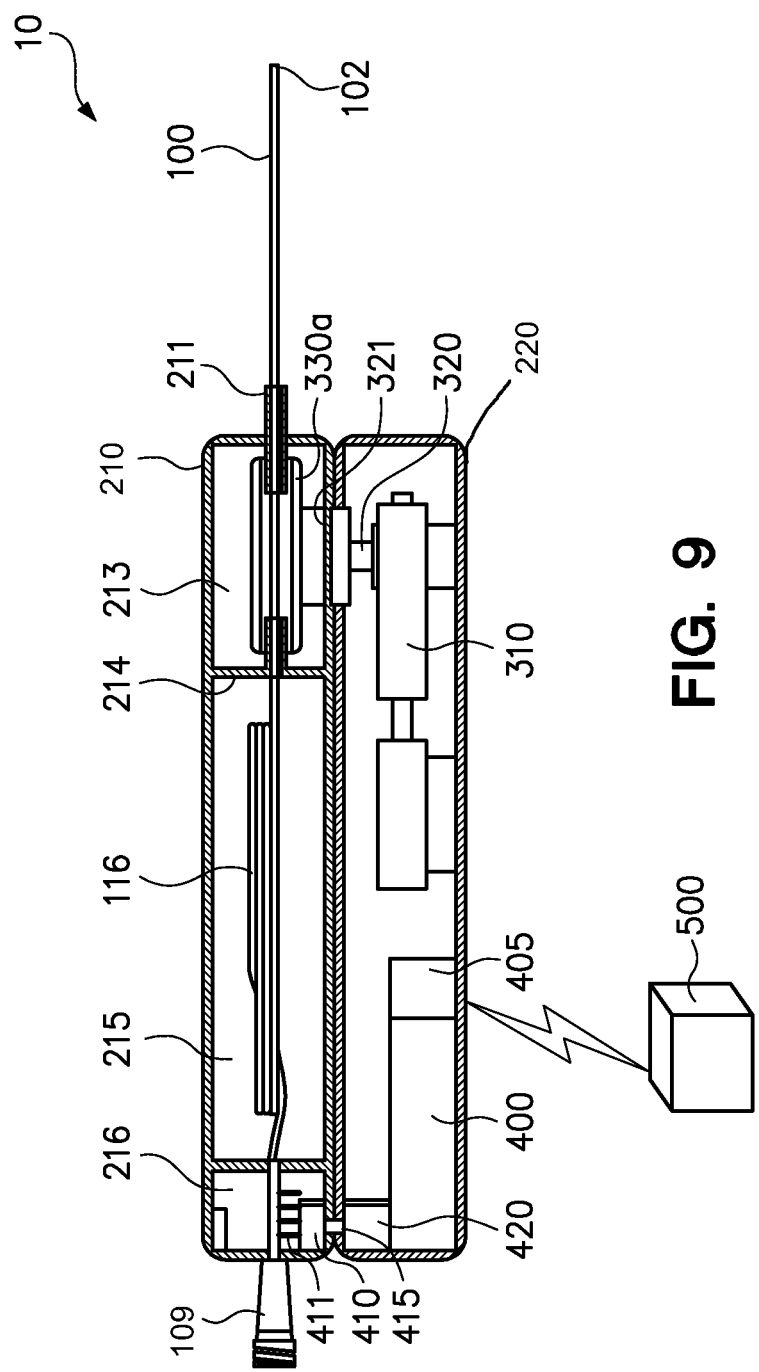
FIG. 9 is an elevational sectional view of an embodiment of a medical device provided by assembling of the upper case portion and the lower case portion of FIGS. 8A and 8B. The medical device is in wireless communication with a master controller.

FIG. 9 is an elevational sectional view of an embodiment of a medical device 10 provided by assembling of the upper case portion 210 and the lower case portion 220 of FIGS. 8A and 8B. The windings 116 of the actuation part 100 of the medical device 10 are stored within the cavity 215 of the upper case portion 210 of the case 200. The actuation part 100 of the medical device 10 extends from the proximal end 109 through the windings 116, to the distal end 102 of the actuation part 100 that extends beyond the guide barrel 211 of the upper case portion 210. FIG. 9 shows the manner in which the drive fitting 321 (see FIG. 8B) engages a socket (not shown) in the first rotary drive member 330a which cooperates with the second rotary drive member 330b to controllably advance and withdraw the actuation part 100 from and back into the case 200 of the medical device 10, respectively. Optionally, the upper case portion 210 includes a cavity wall 214 that separates the cavity 215 that houses the windings 116 of the actuation part 100 from the adjacent cavity 213 that houses the first rotary drive member 330a and the second rotary drive member 330b (FIG. 8A) of the drive assembly 300. The medical device 10 of FIG. 9 further includes the electrical controller 400 disposed in the lower case portion 220 and used to receive command signals from the master controller 500 and to generate control electrical signals to the plurality of electrically-conductive conduits 130 (FIG. 2) within the actuation part 100 to energize the plurality of electrodes 112 (e.g., FIG. 2) to bend the bendable portion 110 (e.g., FIG. 2) of the actuation part 110. The electrical controller 400 relays the electrical currents through the interface 402 disposed in the lower case portion 220 to the current distributor 410 disposed in the upper case portion 210. The current distributor 410 is the interface between the electrical controller 400 and the actuation part 100 of the medical device 10. The proximal end 109 of the actuation part 100 of the medical device 10 is fixed relative to the upper case portion 210 to maintain a plurality of electrical feeder wires 411 extending between the current distributor 410 and the stationary proximal end 109 of the actuation part 100. It will be understood that the distributor cavity 216 of the upper case portion 210 may be sealed to protect the feeder wires 411 and related terminals from contamination sources that may exist in the adjacent windings 116.

In the embodiment of the medical device of FIG. 9, the number of the plurality of feeder wires 411 provided to deliver electrical current from the electrical controller 400 to the electrically-conductive conduits 130 (e.g., FIG. 2) will match the number of the plurality of electrically-conductive conduits 130. An interface socket 415 may be disposed intermediate the interface 420 of the lower case portion 220 and the current distributor 410 of the upper case portion 210. In one embodiment, the electrical controller 400 may include a wireless interface device 405 that is electrically connected to the electrical controller 400 and drive assembly 300 enables the electrical controller 400 and drive assembly 300 to wirelessly communicate with the master controller 500.

Figure 10:
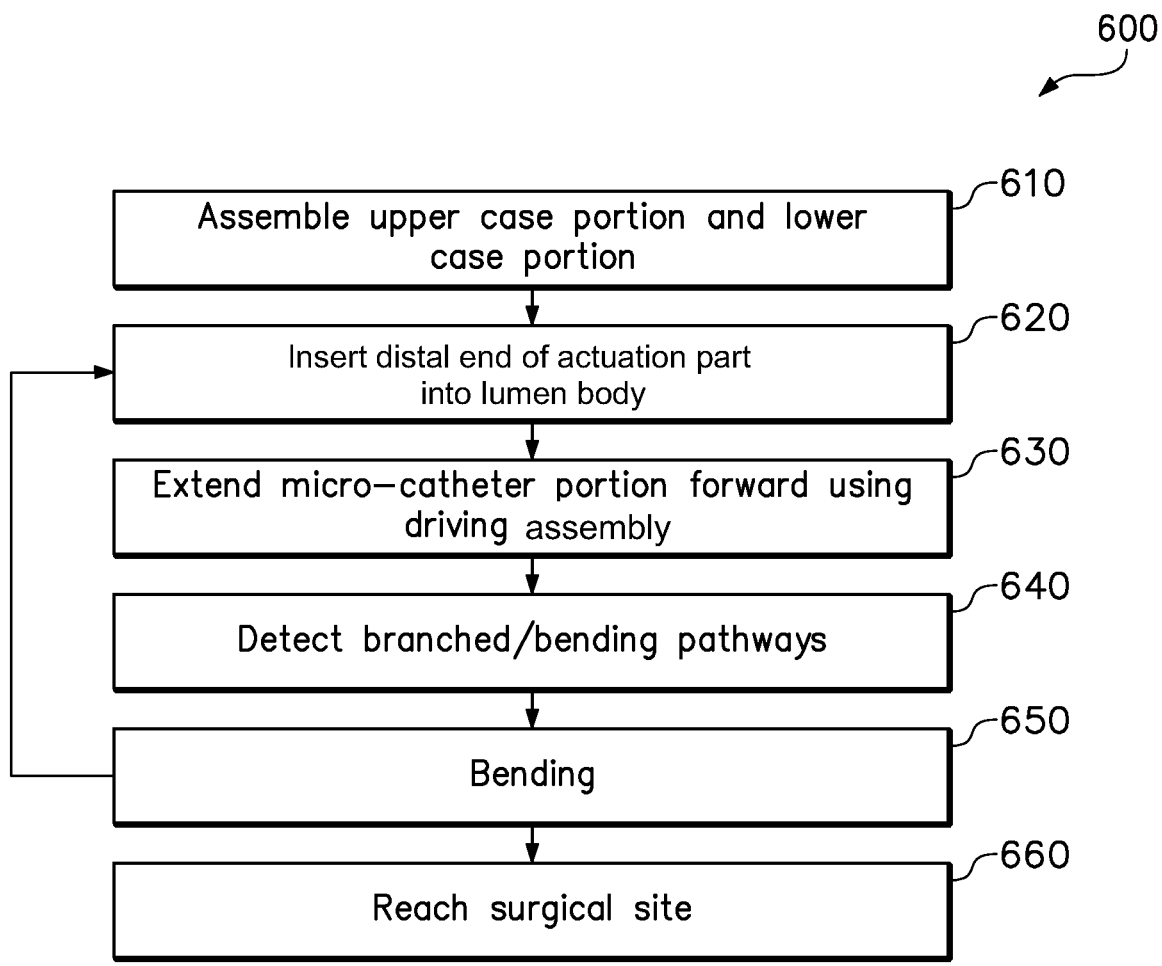
FIG. 10 is a flowchart illustrating the steps of a method of performing surgery by use of the embodiment of an embodiment of the medical device illustrated in FIGS. 7A, 7B and 8.

FIG. 10 is a flowchart illustrating the steps of a method 600 of performing surgery on a body of a patient using an embodiment of the medical device 10 illustrated in FIGS. 8A and 8B. The method 600 includes a step 610 of assembling the upper case portion 210 and the lower case portion 220 to form a case 200, the step 620 of introducing the distal end 102 of the actuation part 100 into a lumen of the body, the step 630 of extending the actuation part 100 forward and into the lumen of the patient using the drive assembly 300, the step 640 of detecting a branched or bending pathways of the lumen or bodily passage in which the actuation part 100 is disposed using an imaging device, the step 650 of bending the bendable portion 110 at the distal end 102 of the actuation part 100 of the medical device 10 to steer the actuation part 100 into a desired direction through the branched or bending pathways observed using an imaging device, and the step 660 of reaching the surgical site with the distal end 102 of the actuation part 100.

Conventional techniques and methods known in the medical sciences may be used in conjunction with the methods and with the medical device 10. For example, but not by way of limitation, the step 640 in FIG. 10 requires the surgeon to "detect branched and bending pathways" of the lumen of the body in which the actuation part 10 is introduced. More specifically, the surgeon or operator performing the method of FIG. 10 using the medical device 10 may view images of the lumen or bodily passage (pathway) in the body along which the distal end 102 of the actuation part 100 of the medical device 10 is pushed forward using radiography, magnetic resonance imaging, ultrasound, elastography, tactile imaging, photoacoustic imaging, tomography and other imaging technologies and devices. It will be understood that an imaging device can be present in the room with the patient and that the output of the imaging device can be electrically transmitted to the surgeon or operator using a hardwired connection, for a surgeon who is nearby, and using telecommunications, such as but not limited to the Internet or wireless communications, for a surgeon or operator who is remotely located.

Figure 11:
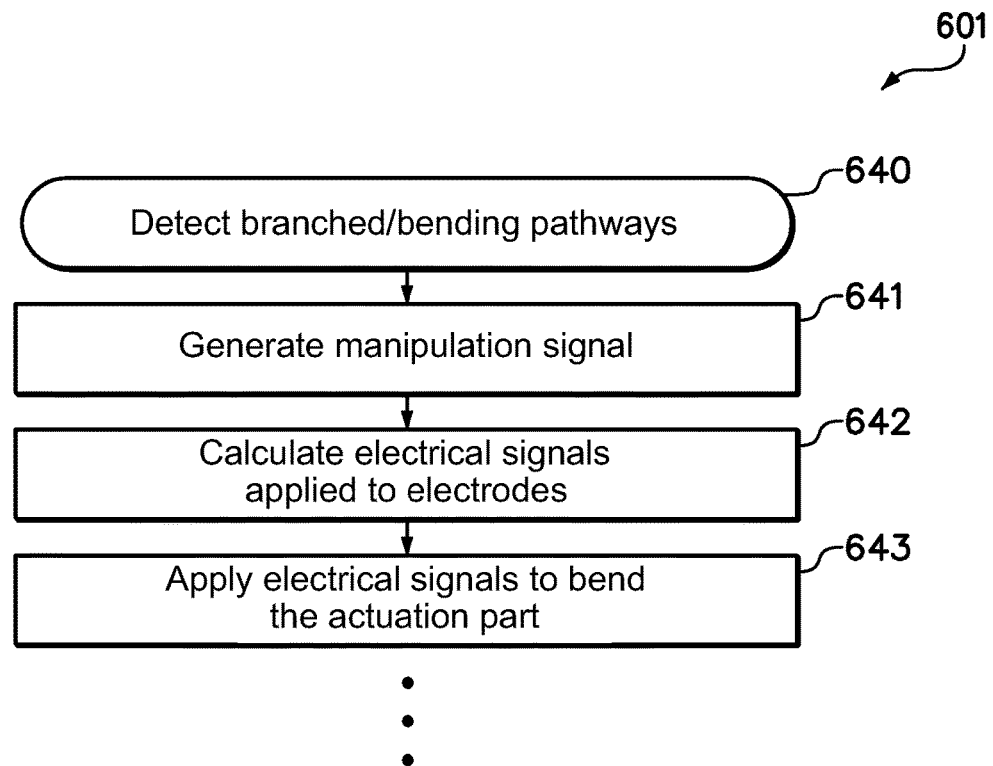
FIG. 11 is a flowchart illustrating a method of imparting a bend to a bendable portion at the distal end of an actuation part of an embodiment of the medical device.

FIG. 11 is a flowchart illustrating a method 601 of controlling an embodiment of the medical device 10 and, more specifically, of imparting a bend to a bendable portion 110 at the distal end 102 of an actuation part 100 of an embodiment of the medical device 10 (e.g., a micro-catheter or a guidewire). Referring also to FIGS. 2 and 9, the method 601 includes the step 641 of generating a manipulation signal using the master controller 500 which will be received by the electrical controller 400 through the wireless interface device 405, step 642 of using the electrical controller 400 to determine the electrical signals to be applied to one or more of the plurality of electrodes 112 to obtain the desired direction and magnitude of bend of the bendable portion 110 of the distal end 102 of the actuation part 100 of the medical device 10, and step 643 of applying the determined electrical signals to be conducted over the electrically-conductive conduits 130 to one or more of the plurality of electrodes 112 to obtain the desired movement in the distal end 102 of the actuation part 100 of the medical device 10.

Figure 12:
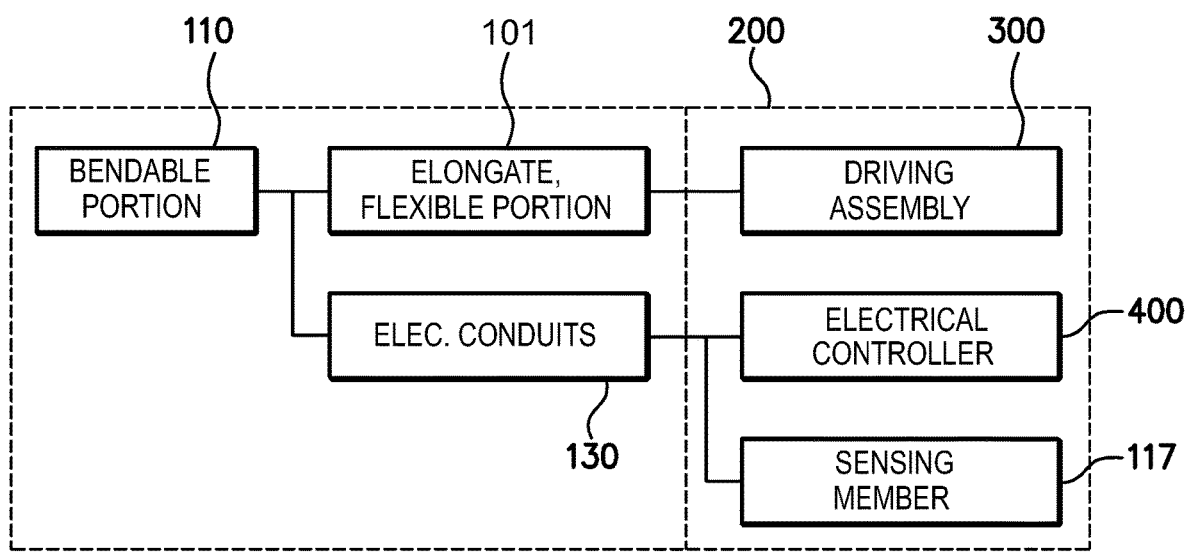
FIG. 12 is a modification of the block diagram of FIG. 6 illustrating the control system structure for an alternative embodiment of the medical device including an actuation part and a case.

FIG. 12 is a modification of the block diagram of FIG. 6 illustrating the control system structure for an alternative embodiment of the medical device 10 including an actuation part 100 and a case 200 (e.g., FIG. 1). The medical device 10 herein may be a micro-catheter with an interior bore 140 (e.g., FIGS. 2-4B) or a guidewire without the interior bore 140 (e.g., FIG. 29). The actuation part 100 includes a bendable portion 110 and an elongate, flexible portion 101. The case 200 includes a drive assembly 300 and electrical controller 400, and further includes a sensing member 117. The sensing member 117 is a bendable portion sensor that is electrically connected to the plurality of electrodes 112 of the bendable portion 110 to sense changes in the electrical signal at each of the plurality of electrodes 112. More specifically, the sensing member 117 is individually electrically connected to each of the plurality of electrodes 112 to monitor changes in the potential at each of the plurality of electrodes 112. Accordingly, the sensing member 117 detects deformation of the bendable portion 110 or the absence thereof based on changes in potential in each of the plurality of electrodes 112 over time.

For example, but not by way of limitation, as the bendable portion 110 and the elongate, flexible portion 120 of the actuation part 100 is advanced forward using the drive assembly 300 of the case 200, the sensing member 117 detects whether the lumen or bodily passage through which the bendable portion 100 of the actuation part 100 is advanced is obstructed or whether there is a bend or obstruction in the lumen or bodily passage that is sufficient to prevent or impair forward movement of the actuation part 100. Also, because an electrical signal is applied to each of the plurality of electrodes 112 by the electrical controller 400, the sensing member 117 may determine whether the intended bending deformation corresponding to the plurality of electrical signals generated by the electrical controller 400 has occurred by receiving feedback about the electrical signal at each of the plurality of electrodes 112 and by comparing that feedback to the electrical signals assigned to each of the plurality of electrodes 112.

The sensing member 117 is electrically connected to each of the electrically-conductive conduits 130 that supply electrical signals to each of the electrodes 112. It will be understood that, just as the character and nature of an electrical signal delivered to an energized electrode 112 determines the unimpaired deformation imparted to the polymer electrolyte layer 139 disposed adjacent to an energized electrode 112, the actual deformation of the polymer electrolyte layer 139 can be compared to the electrical signal delivered to the adjacent electrodes to determine the direction and magnitude of an external force acting on the polymer electrolyte layer 139.

Figure 13:
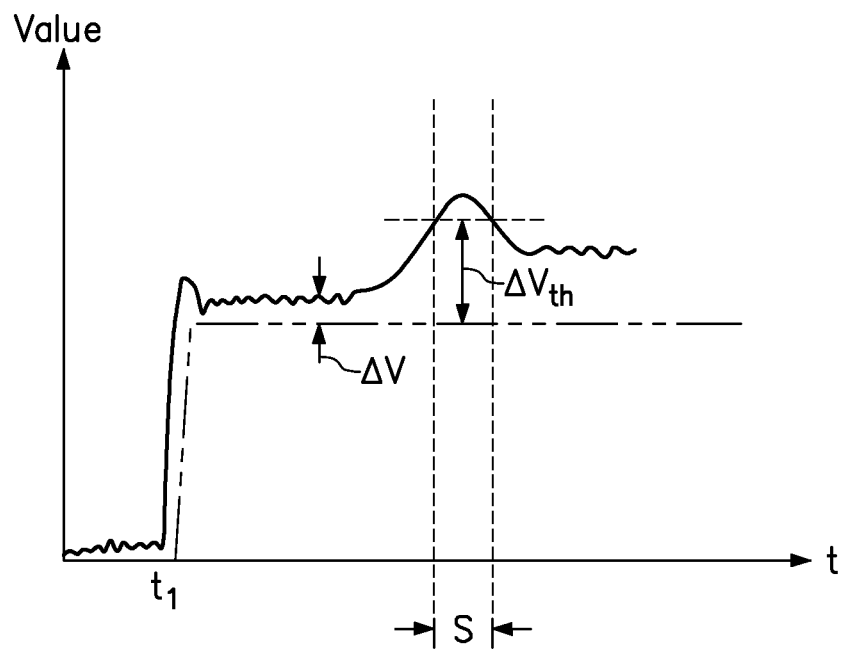
FIG. 13 is a graph illustrating variance over time in an electrical signal applied to an electrode disposed with other electrodes to surround a polymer electrolyte layer of a bendable portion of an actuation part of an embodiment of a medical device.

FIG. 13 is a graph illustrating variance over time in an electrical current applied to a polymer electrolyte layer 139 of a bendable portion 110 of an actuation part 100 of an embodiment of a medical device 10. FIG. 13 is a graph showing a change in electrical signal occurring at an electrode 112 monitored using the sensing member 117. The solid line of FIG. 13 indicates the value of a sensed electrical signal at any one of a plurality of electrodes 112. The dotted line of FIG. 13 indicates the value of an electrical signal that is applied to an electrode 112 to produce a bend in a desired direction and at a desired magnitude as determined using the electrical controller 400 and an input signal from the master controller 500.

Changes in the electrode potential sensed by the sensing member 117 are caused by both an electrical signal applied to the plurality of electrodes 112 by the electrical controller 400 for bending control, and by external forces. Accordingly, the sensing member 117 may be used to determine the presence, direction and magnitude of an external force applied to the bendable portion 110 by taking into account how the electrical controller 400 performs bending control. As illustrated in FIG. 13, an electrical signal is applied to an electrode 112 at a time designated as $t_1$. As a result, the value of the electrical signal sensed by the sensing member 117 increases abruptly at time $t_1$. Therefore, the sensing member 117 may determine the direction and magnitude of any external force that may be applied to the bendable portion 110 based on the difference in the electrical signal, or $\Delta V$, between the sensed value and $\Delta V_{th}$, the value applied by the electrical controller 400.

The sensing member 117 may be configured to determine the direction and/or the magnitude of an applied external force depending on whether the difference between the sensed value and the value applied by the master controller 500 exceeds a preset threshold value, $\Delta V_{th}$. For example, the actuation part 100 may be subjected to a small amount of external force as the distal end 102 is brought into contact with a lumen wall or as it encounters sliding friction while being pushed forward along a lumen or bodily passage. Accordingly, it is possible to permit an expected small amount of external force during intraluminal movement of the actuation part 100 and to detect the application of a larger magnitude external force by determining whether an external force is applied or not based on a threshold value.

While FIG. 13 illustrates the value applied to the electrode upon bending and the value sensed at the electrode due to a deformation on the same scale, this is for ease of explanation and these values may vary in an actual situation, depending on the position of installation and the wire characteristics. In this case, using a method of calculation suitable for the wire characteristics, the application of an external force can be determined based on the value applied upon bending.

In this exemplary embodiment, an external force is sensed by using a plurality of four electrodes 112 used for bending control, without the addition of external force sensing electrodes to the bendable portion 110. However, this is merely an example, and an external force may be sensed using various structures.

Figure 14:
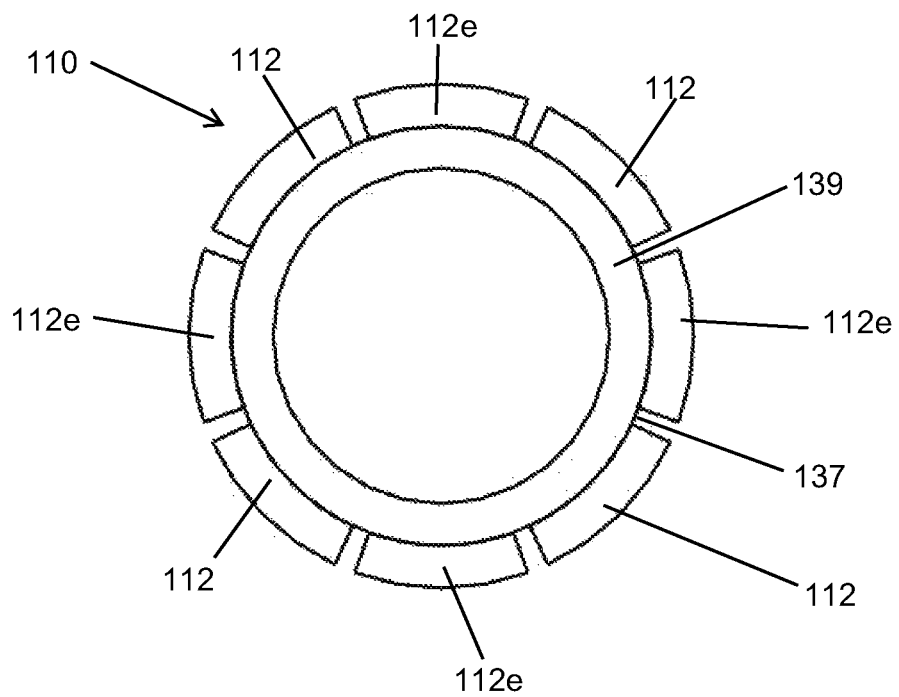
FIG. 14 is a cross-sectional view illustrating an alternative distribution of individual electrodes in recesses formed into a polymer electrolyte layer of a bendable portion of an actuation part of an embodiment of a medical device.

FIG. 14 is a cross-sectional view illustrating an alternative distribution of the plurality of electrodes 112 in a bendable portion 110 of an actuation part 100 of an embodiment of a medical device 10. The arrangement of the eight electrodes of the bendable portion 110 illustrated in FIG. 14 includes four (motive) electrodes 112 for responding to electrical signals generated by the electrical controller 400 (not shown) and an additional four sensing electrodes 112e for sensing the deformation of the bendable portion 110 in which the eight electrodes are together disposed. The embodiment of the bendable portion 110 of FIG. 14 includes a polymer electrolyte layer 139 having an exterior wall 137 for disposing the electrodes 112 and 112e.

Figure 15:
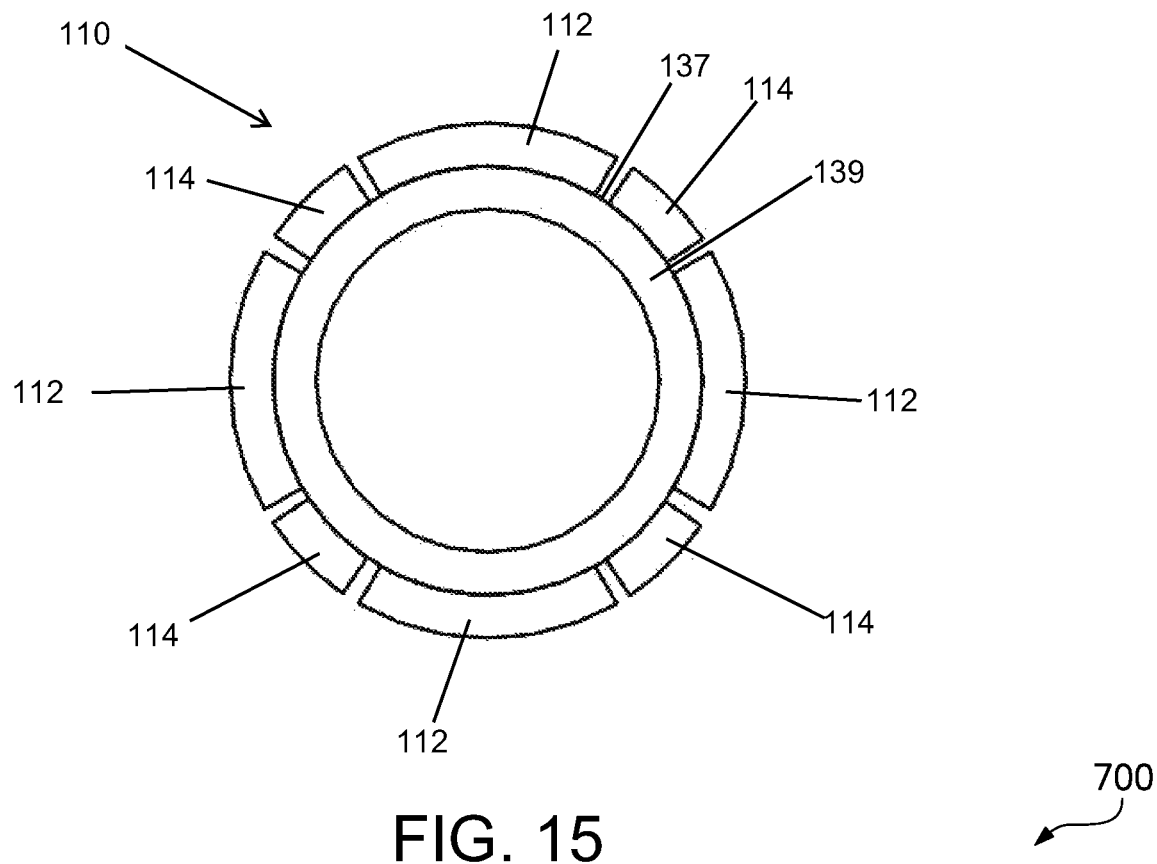
FIG. 15 is a cross-sectional view of an alternative configuration for a bendable portion of an actuation part of the medical device.

FIG. 15 is a cross-sectional view of an alternative configuration for a bendable portion 110 of an actuation part 100 of an embodiment of the medical device 10. FIG. 15 illustrates a polymer electrolyte layer 139 having an exterior wall 137 for disposing the electrodes 112. Circumferentially intermediate each adjacent pair of electrodes 112 resides a strain gauge 114 that measures the strain applied to the bendable portion 110 of the actuation part 100 as a result of internal forces applied by the deformation of the polymer electrolyte layer 139 disposed adjacent one or more energized electrodes 112 and external forces applied to the bendable portion 110 as a result of physical interaction with the lumen or bodily passage through which the actuation part 100 of the medical device 10 is being advanced.

Figure 16:
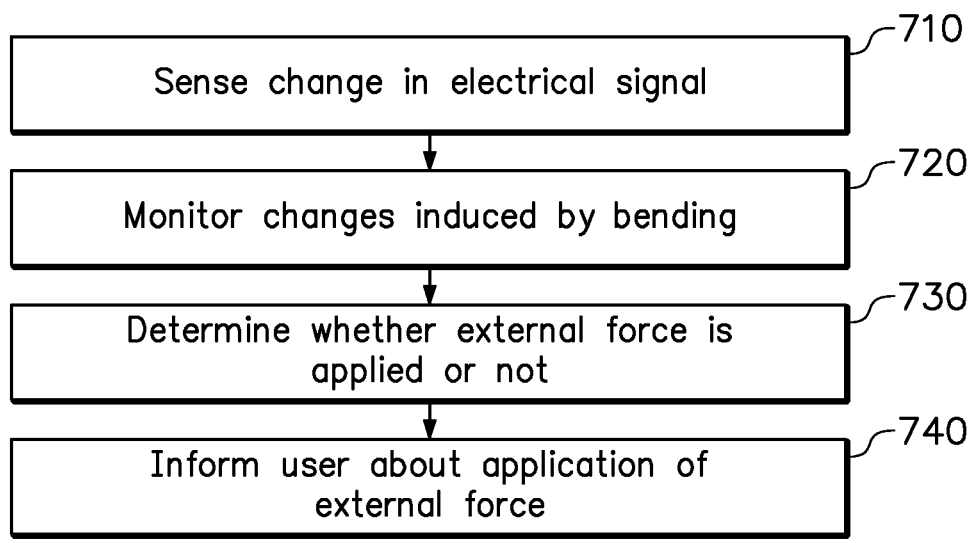
FIG. 16 is a flowchart illustrating a method of using a sensing member to monitor the performance of an embodiment of a medical device and of determining the impact of an external force on the performance of the embodiment of the medical device.

FIG. 16 is a flowchart illustrating a method of using a sensing member 117 to monitor the performance of an embodiment of a medical device 10 and of determining the impact of an external force on the performance of the embodiment of the medical device 10. The medical device 10 herein may be a micro-catheter with an interior bore 140 (e.g., FIGS. 2-4B) or a guidewire without the interior bore 140 (e.g., FIG. 29). The sensing member 117 may be used to continuously monitor changes in electrical signal sensed at the plurality of electrodes 112 of the bendable portion 110. For example, the sensed value of the electrical signal may be the potential of each of the plurality of electrodes 112.

The sensing member 117 may monitor changes in electrical signal induced by the user's bending. That is, the sensing member 117 receives information about the user's bending from the electrical controller 400 or the master controller 500 and the sensing member 117 then monitors changes in electrical signals induced by bending of the bendable portion 110. Then, the sensing member 117 monitors changes in electrical signal induced by actual bending due to both internal and external forces and compares that change in the electrical signal to the isolated electrical signal indicating the intended bending.

When a change in signal (except for a change induced by bending) is sensed during monitoring, the sensing member 117 determines whether the change exceeds a preset threshold value or not, and if so, determines that an external force is applied. Furthermore, in this step, the direction of the external force or the amount of the external force may be calculated by combining information about changes at the electrodes 112.

Once the application of an external force is detected, the step of informing the user of this is performed. In this exemplary embodiment, the sensing member 117 may send an external force generation signal to the master controller 500, and issue an alarm message, an alarm sound, or haptic feedback to the user through the master controller 500. In this case, the sensing member 117 may, through the master controller 500, advise the user of both the direction and magnitude of an external force being applied to the bendable portion 110 and thereby enable the user to determine how to manipulate the bendable portion 110 for advancing beyond the obstacle engaging the actuation part 100, as well as the generation of the external force. It will be understood that if the actuation part 100 is advanced through a lumen or bodily passage with excessive force damage to contacted body tissues may occur. The capacity to detect the application of external force to the bendable portion 110 of the actuation part 100 of the medical device 10 enables the user to deactivate or slow the drive assembly 300 through the master controller 500.

The embodiments of the medical device 10 illustrated in FIGS. 1, 8A, 8B and 9 include a drive assembly 300 comprising a motor 310, an intermediate worm gear 320 and a drive fitting 321 positioned to be received into a corresponding drive socket (not shown in FIG. 8A) formed in the first rotary drive member 330a of the upper case portion 210 shown in FIG. 8A. It will be understood that the first rotary drive member 330a and the second rotary drive member 330b illustrated in FIG. 8B are limited in the amount of surface contact between these drive components and the actuation part 100 engaged thereby. As a result of the limited amount of surface contact between the first rotary drive member 330a and the second rotary drive member 330b illustrated in FIG. 8B, on the one hand, and the actuation part 100, on the other hand, the resulting frictional force between the actuation part 100 and the first rotary drive member 330a and the second rotary drive member 330b are also limited. If the resistance to movement and advance of the actuation part 100 into or through a lumen or bodily passage is sufficiently high, then it may become difficult to smoothly and controllably move the actuation part 100 to the desired position for performing a planned surgery in the body.

Figure 17:
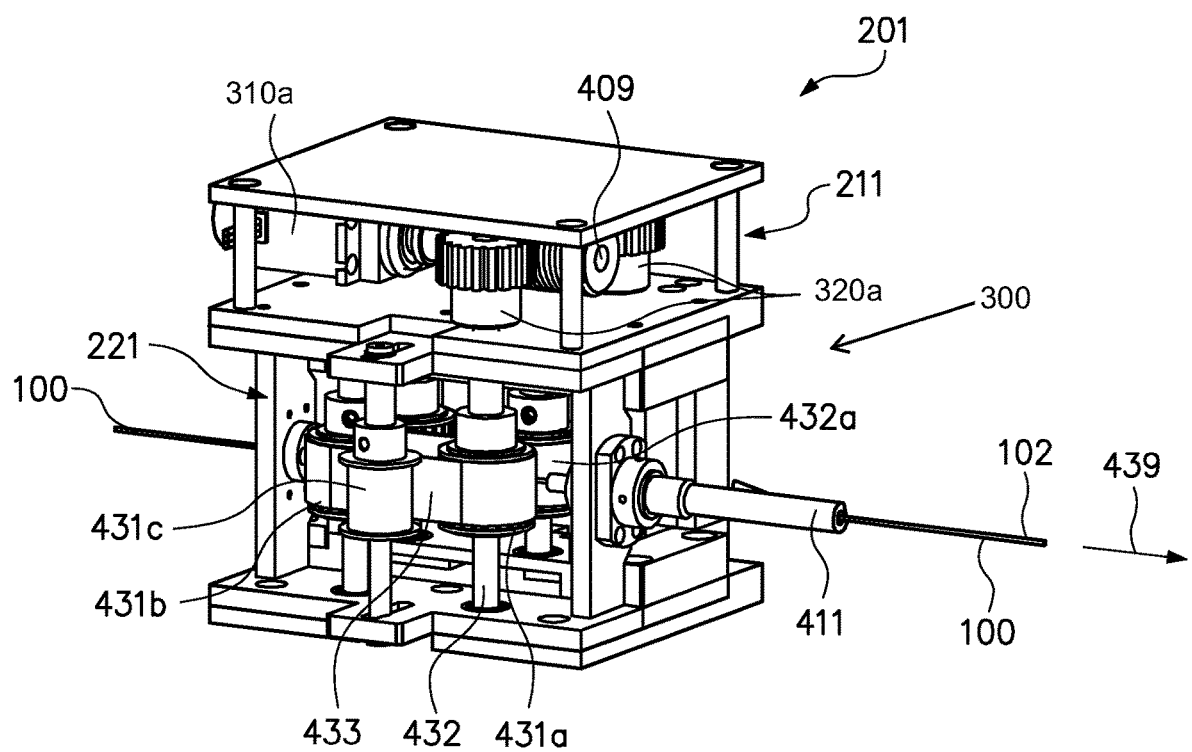
FIG. 17 illustrates an alternate embodiment of the case portion of the medical device for controllably advancing and withdrawing the actuation part of the medical device.

FIG. 17 illustrates an alternate embodiment of the case 201 portion of the medical device 10 for controllably advancing and withdrawing the actuation part 100 of the medical device 10. The medical device 10 herein may be a micro-catheter with an interior bore 140 (e.g., FIGS. 2-4B) or a guidewire without the interior bore 140 (e.g., FIG. 29). The case 201 of the embodiment of the medical device 10 illustrated in FIG. 17 includes a drive assembly 300 that provides increased contact area between the drive members 431a and 432a and the actuation part 100 and, as a result, provides increased frictional force for moving the actuation part 100 against resistance to movement. A drive assembly 300 of the case 201 of FIG. 17 includes a guide barrel 411, a motor 310a, one or more intermediate worm gears 320a, and the drive assembly 300 is operated by the motor 310a working through the one or more worm gears 320a. Like the case 200 illustrated in FIGS. 8A and 8B, the case 201 of FIG. 17 includes a case upper portion 211 and a case lower portion 221 adapted for engaging and being coupled with the case upper portion 211. The motor 310a and the one or more worm gears 320a are disposed in the case upper portion 211 and a worm gear 320a is positioned to dispose a drive fitting (not shown in FIG. 17) disposed on the bottom of the worm gear 320a into engagement with an inversely-shaped socket (not shown in FIG. 17) on a drive shaft 432 that is a part of the drive assembly 300. The drive assembly 300 includes a pair of drive spools 431a and 432a that are positioned one opposing the other on opposite sides of a pathway through the case lower portion 221 in which the actuation part 100 moves through the case lower portion 221. Drive spool 431a is coupled through a first belt 433 to an auxiliary spool 431b and drive spool 432a is coupled through a second belt 434 (not shown in FIG. 17—see FIG. 18) to an auxiliary spool 432b (not shown in FIG. 17—see FIG. 18). The actuation part 100 passes intermediate belts 433 and 434 and is engaged by both of the belts 433 and 434. The actuation part 100 is controllably pushed forward in the direction of arrow 439 or withdrawn (in the opposite direction of the arrow 439) by operation of the motor 310a to drive the drive spools 431a and 432a. It will be understood that the contact area between the belts 433 and 434 and the actuation part 100 is substantially greater in the drive assembly 300 of the case 201 of the medical device 10 illustrated in FIG. 17 as compared to the contact area between the first rotary drive member 330a and the second rotary drive member 330b of the drive assembly 300 of the case 200 of the medical device 10 of FIG. 8A. Optionally, belts 433 and 434, on the one hand, and the mating drive spools 431a and 432a, on the other hand, may include a series of grooves (or other recesses) and/or ridges (or other protrusions), respectively, to promote non-slip engagement with the actuation part 100. Optionally, a pair of worm gears 320a may be disposed on opposite sides of a motor shaft 409 to evenly distribute torque from the motor 310a to the drive spools 431a and 431b. Optionally, tensioners 431c may be provided to enable the adjustment and maintenance of proper tension in the belts 433 and 434. Optionally, the drive spools 431a and 431b may together be biased into engagement with the actuation part 100 to ensure non-slip frictional engagement between the belts 433 and 434 and the actuation part 100 to improve controllability and prevent slippage. Optionally, as will be seen in FIG. 18, one of the drive spools 431a and 431b may be biased into engagement with the actuation part 100 for the same purposes.

Figure 18:
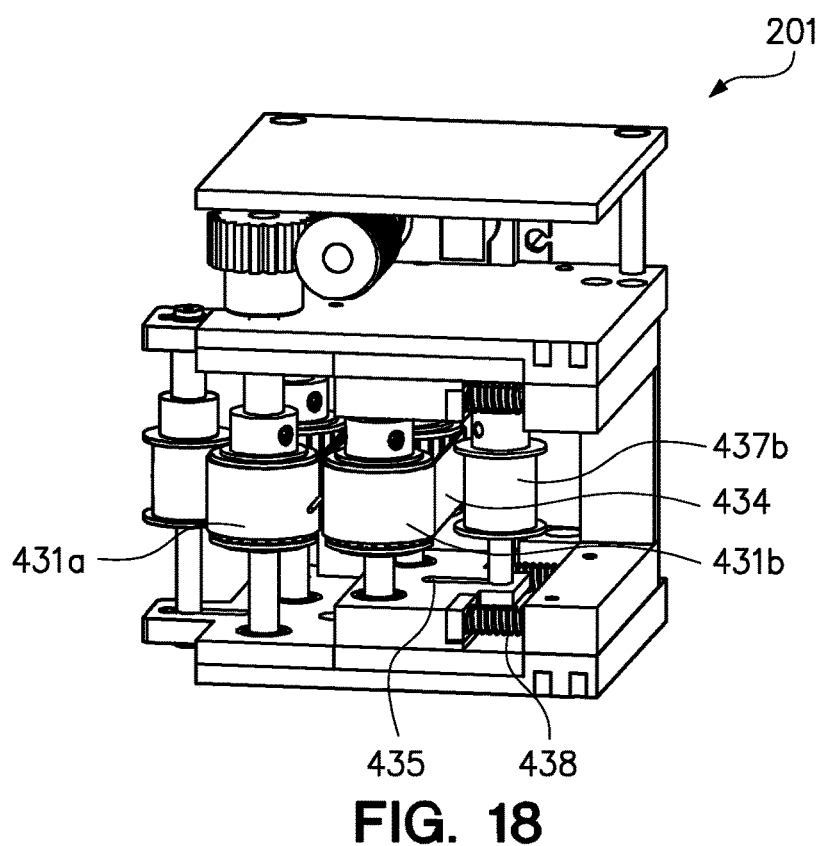
FIG. 18 is a perspective view of an alternative case with a guide barrel removed to reveal the positions of the components therein.

FIG. 18 is a perspective view of the alternative case 201 of FIG. 17 with the guide barrel 411 removed to reveal the positions of the components therein. Drive spools 431a and 431b are seen straddling the actuation part 100 of the medical device 10 as they do in the embodiment of FIG. 17. Additionally, the embodiment of the case 201 of the medical device 10 of FIG. 18 includes a tensioner 437b disposed on the case 201 to move as permitted by a slot 435. The tensioner 437b shown in FIG. 18 is biased into engagement with a belt 434 using one or more springs 438 that maintain the tensioner 437b engaged with the belt 434 to keep the belt 434 in non-slipping engagement with the drive spool 431b.

Figure 19:
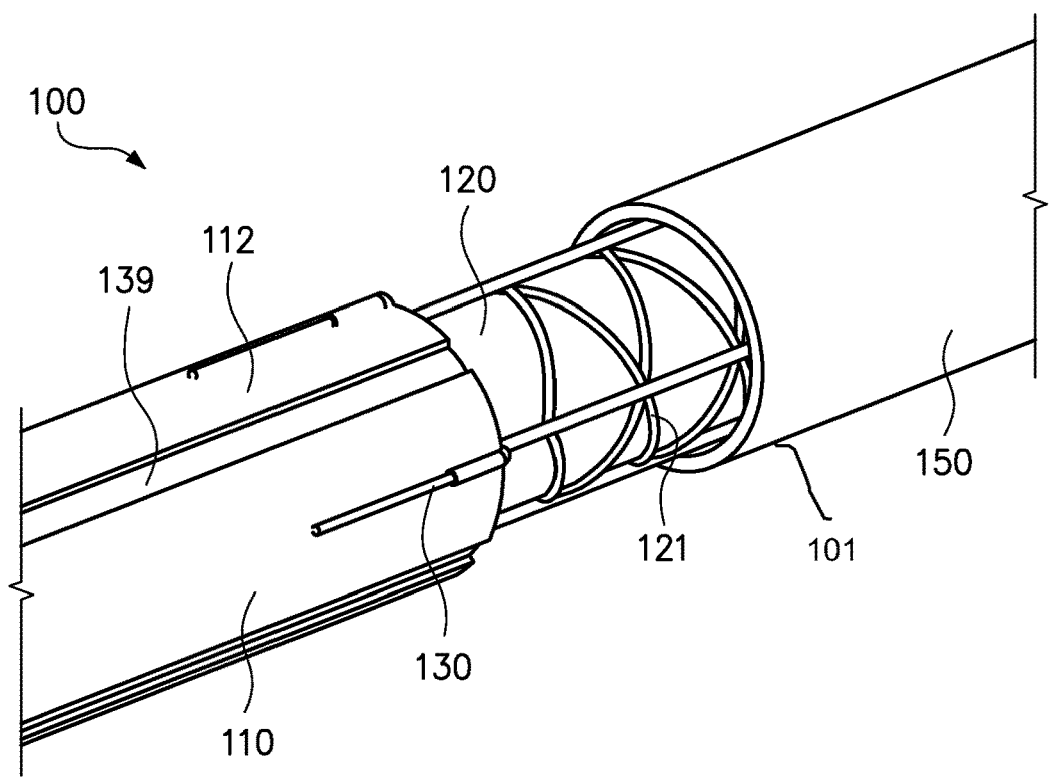
FIG. 19 is perspective view of an elongate, flexible portion of an actuation part of a medical device with a section of an outer member removed to reveal details of the components of the actuation part of this embodiment of the medical device.

FIG. 19 is a perspective view of an elongate, flexible portion 101 of an actuation part 100 of an embodiment of a medical device 10 with a section of an outer member 150 removed to reveal details of the interior of the actuation part 100 of this embodiment of the medical device 10. The medical device 10 herein may be a micro-catheter with an interior bore 140 (e.g., FIGS. 2-4B) or a guidewire without the interior bore 140 (e.g., FIG. 29). The outer member 150 is shown to the right side of FIG. 19 but is removed from the left side of FIG. 19 to reveal the bendable portion 110 of the actuation part 100 including the inner member 120, and the electrodes 112 circumferentially distributed about a polymer electrolyte layer 139. Each electrode 112 is connected to an electrically-conductive conduit 130 that delivers an energizing electrical signal to one or more selected electrode(s) 112 to actuate the polymer electrolyte layer 139 to bend. FIG. 19 further illustrates a reinforcing mesh 121 comprising a wire or filament that is braided or wound radially intermediate the inner member 120 and the outer member 150 to provide enhanced structural rigidity and resistance to axial compression and enhanced resistance to torsional deformation of the actuation part 100 for improved control and steerability. It will be understood that the structure of the reinforcing mesh 121 may vary. Other embodiments of the actuation part 100 of the medical device 10 may include encircling coils of reinforcing wire (not shown) as opposed to braids or mesh. The material of the reinforcing mesh 121 may include, but is not limited to, stainless steel, tungsten or nylon. In one embodiment of the actuation part 100 of the medical device 10, the electrically-conductive conduits 130 through which electrical signals are delivered to the bendable portion 110 of the actuation part 100 comprise a plurality of very slender wires available from, among others, MK Electron Co., Ltd. of Gyeonggy-do, Korea. These wires may have a diameter of 25 μm, or 15 μm or less, and may comprise gold, gold-silver alloy or other highly conductive metals that demonstrate high chemical stability. These wires may be embedded in an insulating medium and may be of a multiple-layer braided construction.

Figure 20:
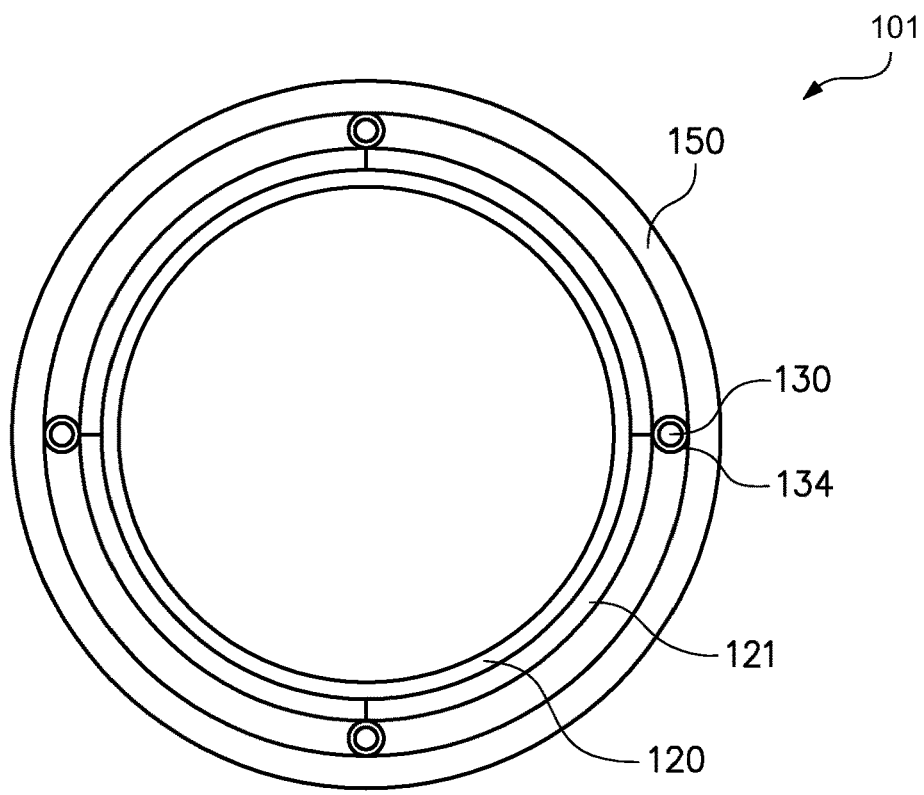
FIG. 20 is cross-sectional view of an embodiment of an elongate, flexible portion of an actuation part of a medical device. The elongate, flexible portion may include electrically-conductive conduits and a metal reinforcing mesh or braid.

FIG. 20 is cross-sectional view of an embodiment of an elongate, flexible portion 101 of an actuation part 100 of an embodiment of a medical device 10. The medical device 10 herein may be a micro-catheter with an interior bore 140 (e.g., FIGS. 2-4B) or a guidewire without the interior bore 140 (e.g., FIG. 29). It will be understood that the elongate, flexible portion 101 includes an inner member 120 and a reinforcing mesh 121. An insulating layer 133 is disposed about the reinforcing mesh to isolate the reinforcing mesh 121 from the electrically-conductive conduits 130 to prevent electrical shorts. As shown in FIG. 20 the electrically-conductive conduits 130 are circular in cross-section and are formed within a space defined within the insulating layer 133 between the outer member 150 and the reinforcing mesh 121. The elongate, flexible portion 101 illustrated in FIG. 20 further includes an insulation coating 134 to further insulate the electrically-conductive conduits 130 from the outer member 150 and also from the reinforcing mesh 121.

Figure 21:
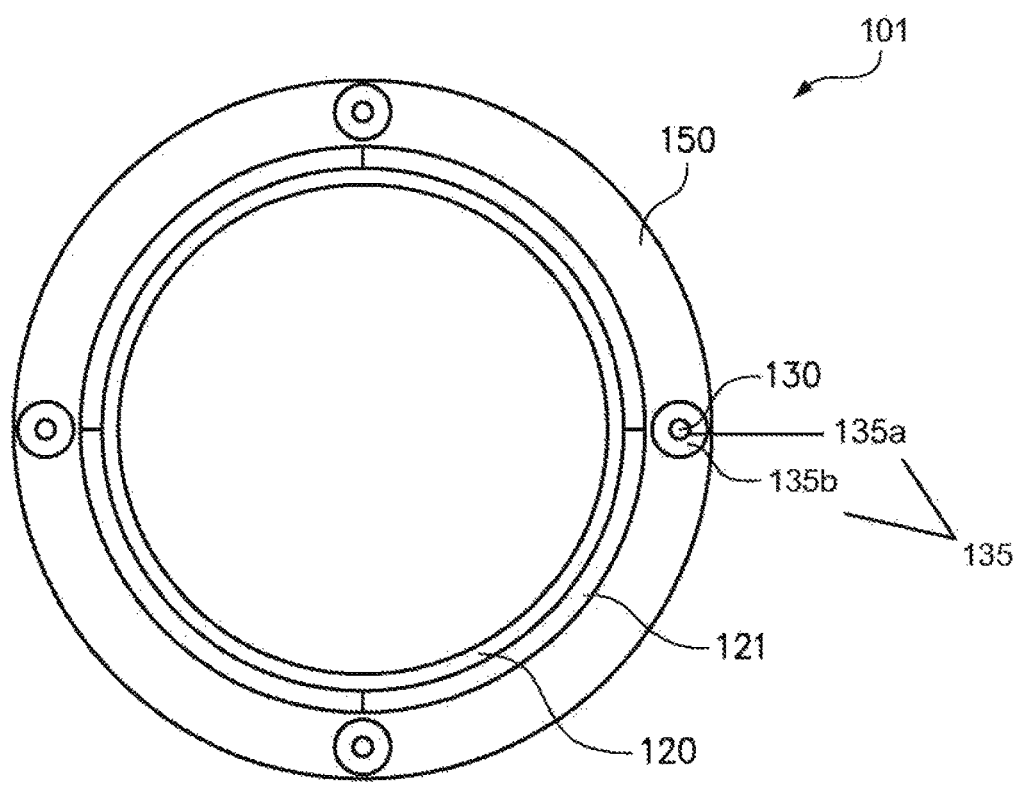
FIG. 21 is a cross-sectional view of an alternative embodiment of the elongate, flexible portion of an actuation part of the medical device in which each of the electrically-conductive conduits are embedded within a lumen structure and each electrically-conductive conduit and its lumen structure are together encased within the material of the outer member.

FIG. 21 is a cross-sectional view of an alternative embodiment of the elongate, flexible portion 101 of the actuation part 100 of an embodiment of the medical device 10 having an inner member 120, a reinforcing mesh 121 and electrically-conductive conduits 130. The medical device 10 herein may be a micro-catheter with an interior bore 140 (e.g., FIGS. 2-4B) or a guidewire without the interior bore 140 (e.g., FIG. 29). The elongate, flexible portion 101 of FIG. 21 illustrates that the electrically-conductive conduits 130 and one or more lumens 135 around each electrically-conductive conduit 130 are together encapsulated or encased within the material of the outer member 150. The lumens 135 herein may be placed longitudinally within the outer member 150. Each lumen 135 defines an interior space 135a passing through the outer member 150 and an exterior wall 135b. Each electrically-conductive conduit 130 may be correspondingly placed through the each interior space of each lumen 135, so that each electrically-conductive conduit 130 can be insulated by the exterior wall 135b of each lumen 135 to prevent electrical shorts.

Figure 22:
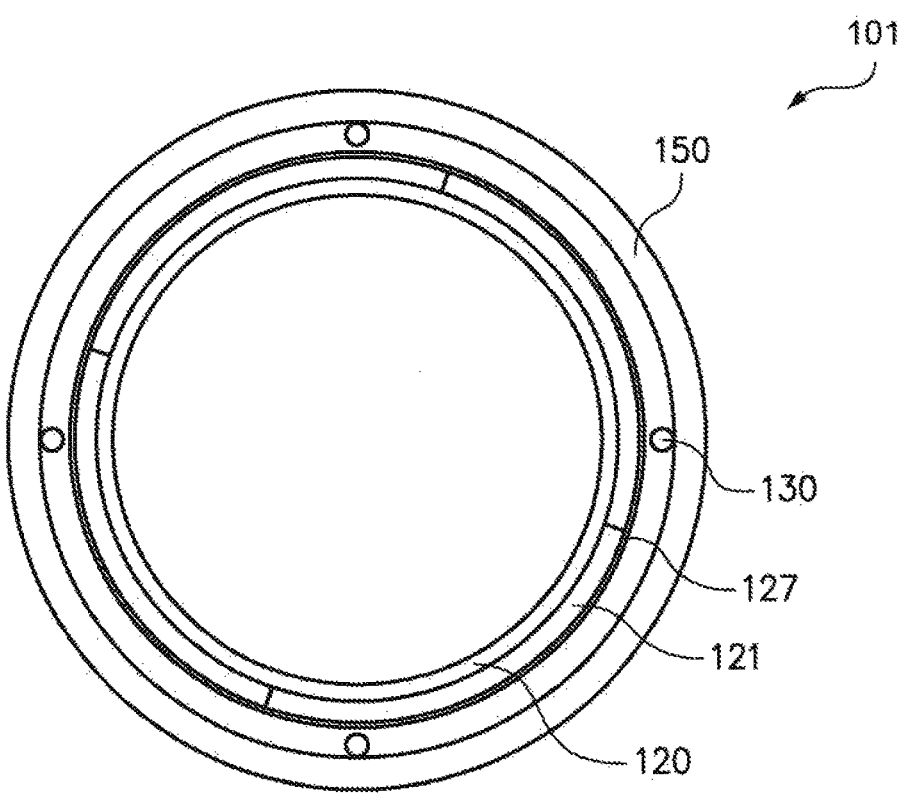
FIG. 22 a cross-sectional view of an alternative embodiment of the elongate, flexible portion of an actuation part of the medical device in which each of the electrically-conductive conduits are electrically insulated encased within a single, tubular insulation member that is surrounded by the outer member.

FIG. 22 a cross-sectional view of an alternative embodiment of the elongate, flexible portion 101 of the actuation part 100 of an embodiment of the medical device 10 having an inner member 120, a reinforcing mesh 121 and an outer member 150. The medical device 10 herein may be a micro-catheter with an interior bore 140 (e.g., FIGS. 2-4B) or a guidewire without the interior bore 140 (e.g., FIG. 29). The embodiment of the elongate, flexible portion 101 of FIG. 22 further includes a tubular insulation member 127 surrounding the reinforcing mesh 121 to further insulate the electrically-conductive conduits 130 from the reinforcing mesh 121.

Figure 23:
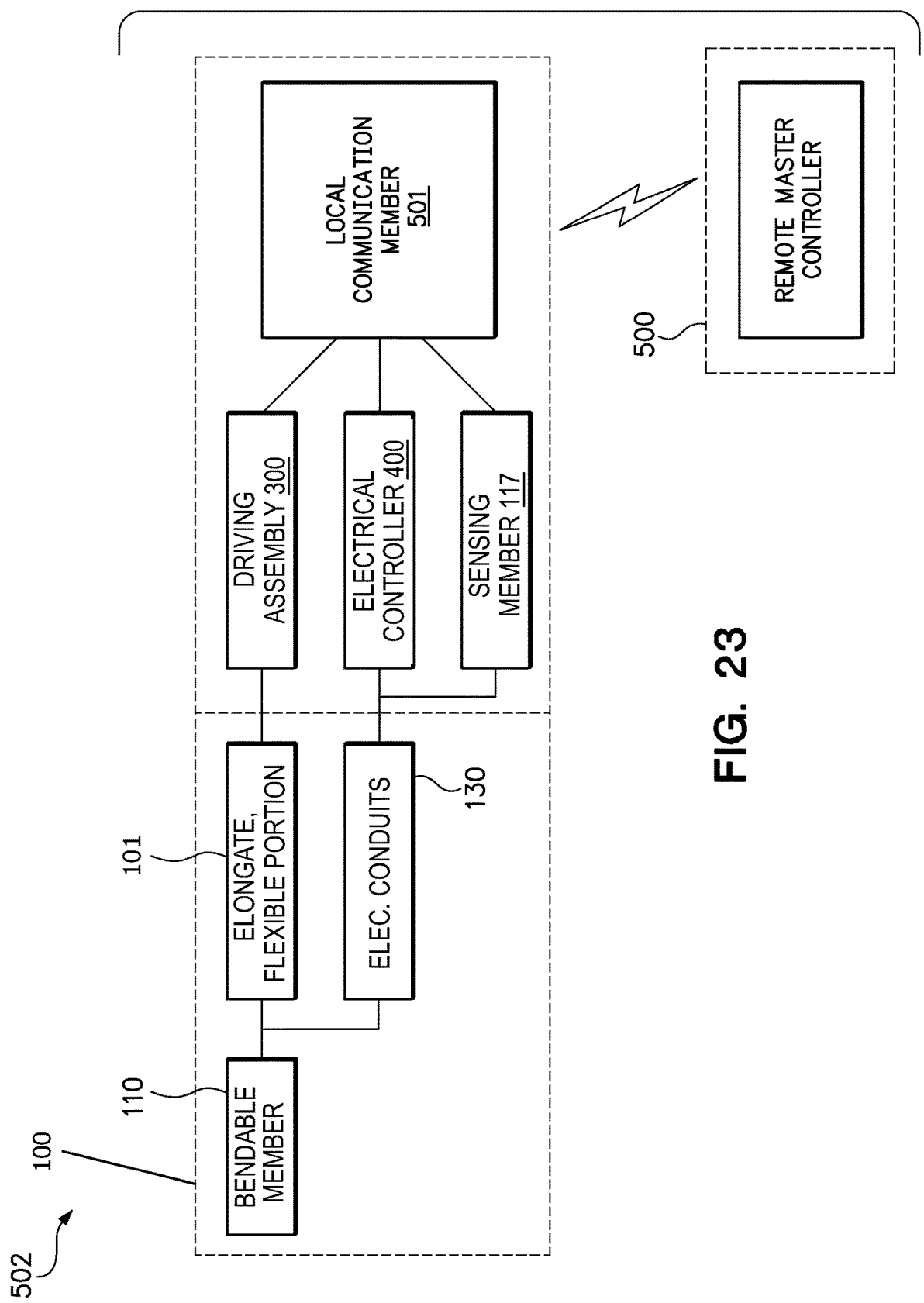
FIG. 23 is a modification of the block diagrams of FIGS. 6 and 12 illustrating a control system for an alternative embodiment of the medical device including an actuation part and a case.

FIG. 23 is a modification of the block diagrams of FIGS. 6 and 12 illustrating a control system 502 for an alternative embodiment of the medical device 10 including an actuation part 100 and a case 200. FIG. 23 illustrates a system for remotely controlling a medical device 10 having an actuation part 100 introduced within a lumen or passage of the body of a patient. The medical device 10 herein may be a micro-catheter with an interior bore 140 (e.g., FIGS. 2-4B) or a guidewire without the interior bore 140 (e.g., FIG. 29). The system 502 comprises a local communication member 501 that remotely communicates with the remote master controller 500. The surgeon, operator or user uses the master controller 500 to remotely operate the medical device 10 that includes the actuation part 100, the drive assembly 300 in the case 200 of the medical device, and the electrically-conductive conduits 130 that carry electrical signals to the bendable portion 110. FIG. 23 illustrates that the surgeon, operator or user may remotely control the medical device 10 from a remote location using the master controller 500 and the local communication member 501, and that the master controller 500 and the local communication member 501 may communicate through telephonic systems, Bluetooth, wireless 802.11 communication and/or the Internet.

In an alternative embodiment of the medical device 10, the electrically-conductive conduits 130 are embedded in a radially exterior surface 122 of the inner member 120, as discussed in connection with FIG. 24.

Figure 24:
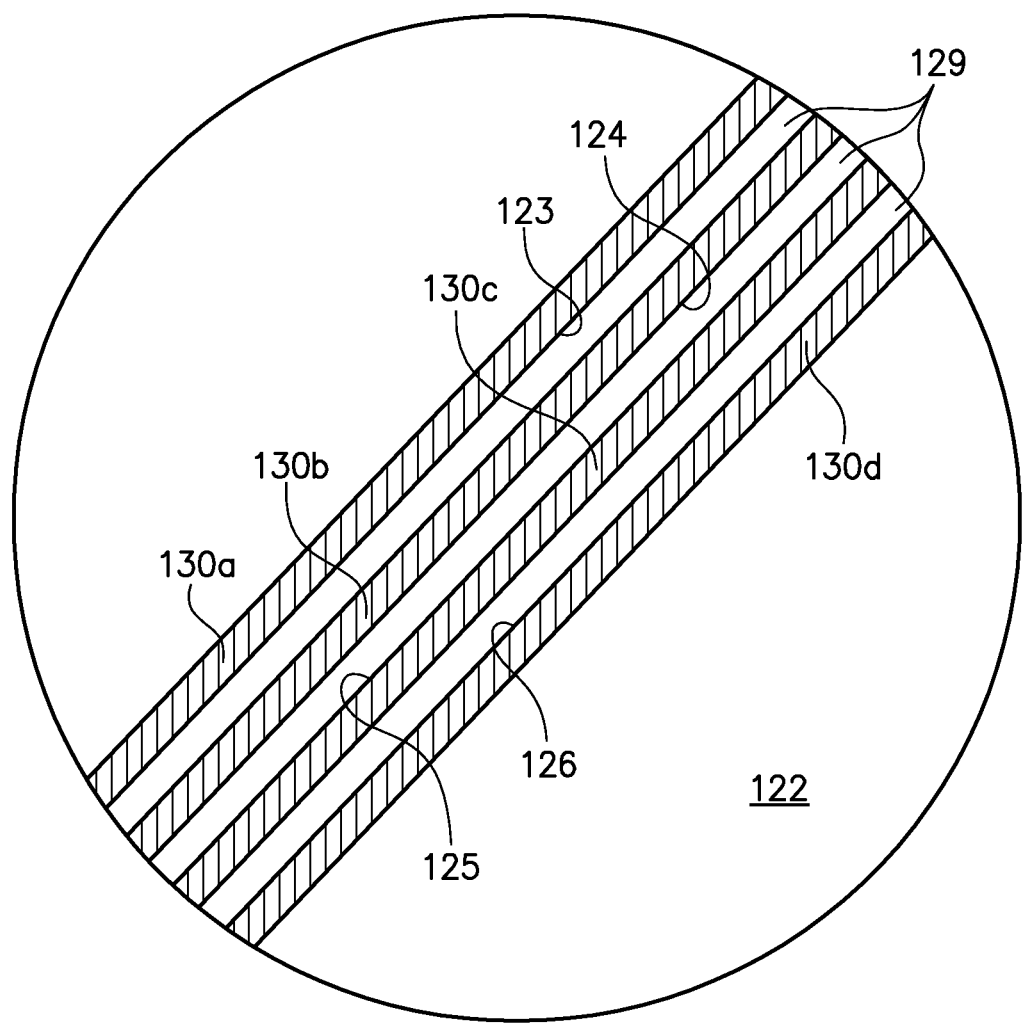
FIG. 24 is an enlarged view of a portion of FIG. 5 showing an arrangement of four electrically-conductive conduits adhered to an exterior surface of the inner member of the elongate, flexible portion of a medical device.

FIG. 24 is an enlarged view of a portion of FIG. 5 and illustrates a plurality of four electrically-conductive conduits 130a, 130b, 130c and 130d disposed within a plurality of four parallel and spaced-apart channels 123, 124, 125 and 126 formed into the exterior surface 122 of the inner member 120. It will be understood that the four electrically-conductive conduits 130a, 130b, 130c and 130d are each isolated one from the others by the barrier portions 129 of the exterior surface 122 disposed intermediate each pair of adjacent channels 123, 124, 125 and 126.

While FIGS. 2-5 and 7 illustrate embodiments of the bendable portion 110 of the actuation part 100 of the medical device 10, it will be understood that other embodiments may be easier to fabricate or may provide improved responsiveness to the electrical signals generated to manipulate and steer the intraluminal the medical device 10 to the targeted location within a body. The discussion that follows relates to an embodiment of the bendable portion 110 of the actuation part 100 of the medical device 10 that provides additional benefits.

Figure 25:
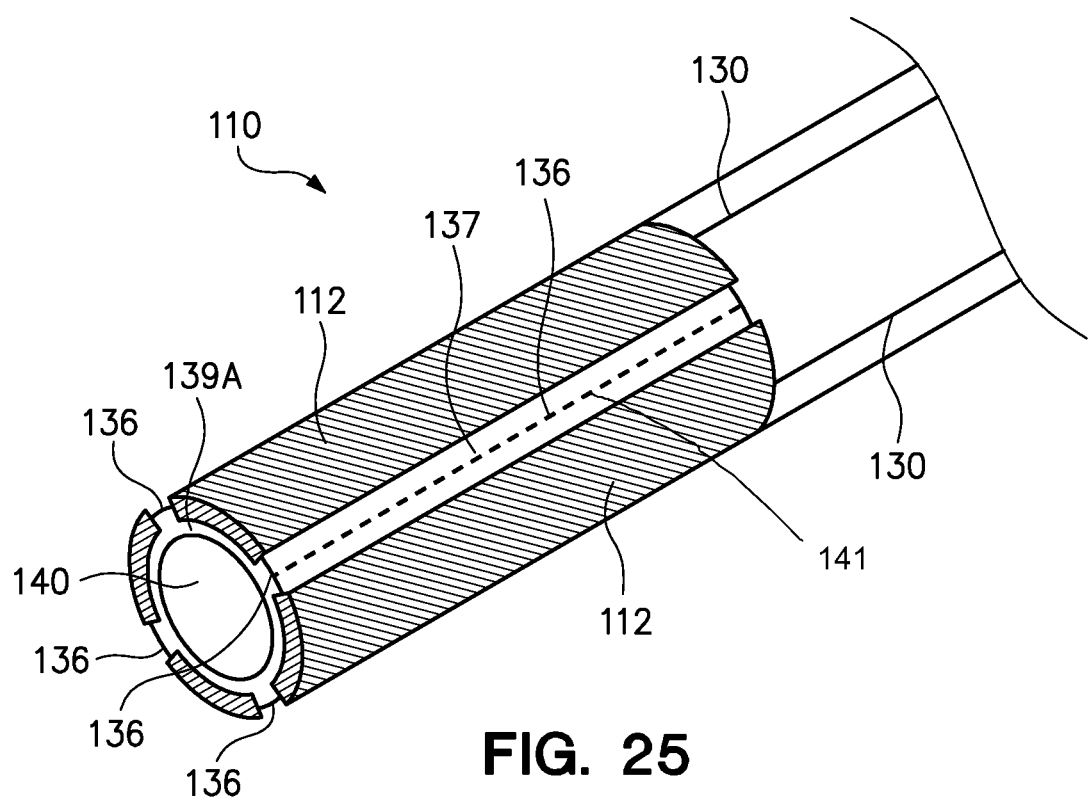
FIG. 25 is an enlarged perspective view of an ionic electroactive polymer actuator that is included in the bendable portion of an actuation part of an alternate embodiment of the medical device.

FIG. 25 is an enlarged perspective view of an alternative tubular polymer electrolyte layer 139A that is included in a bendable portion 100 of an actuation part 100 of an alternate embodiment of the medical device 10 (e.g., a micro-catheter). FIG. 25 shows a bendable portion 110 having a plurality of electrodes 112 circumferentially distributed about the exterior wall 137 of a polymer electrolyte layer 139. The electrodes 112 in FIG. 25 are each coupled to an electrically-conductive conduit 130 for transmitting one or more electrical signals from an electrical source (not shown in FIG. 25) to the electrodes 112. The bendable portion 110 of FIG. 25 includes electrodes 112 that may extend radially further from an axis 141 of the bendable portion 110 (in a relaxed condition) than the exterior wall 137 of the tubular polymer electrolyte layer 139A intermediate adjacent pairs of electrodes 112. The configuration of the bendable portion 110 illustrated in FIG. 25 is the result of a method for making the bendable portion 110, which is discussed in detail below.

The alternate embodiment of the bendable portion 110 illustrated in FIG. 25 is made by forming a tubular polymer electrolyte layer 139A from a polymer, such as Nafion®, available from The Chemours Company of Wilmington, Del., USA. The exterior wall 137 of the tubular polymer electrolyte layer 139A is pre-conditioned by roughening the exterior wall 137 using an abrasive such as, for example, sandpaper, or by an abrasive process such as, for example, sandblasting, followed by cleaning the roughened exterior wall 137 of the tubular polymer electrolyte layer 139A using a reducing agent such as, for example, a hydrogen peroxide ($H_2O_2$) solution and/or a sulfuric acid ($H_2SO_4$) solution, and de-ionized water. The now-roughened and cleaned exterior wall 137 of the tubular polymer electrolyte layer 139A is then deposition-plated with a conductive metal such as, for example, platinum. It will be understood that common methods of depositing a solid coating or layer onto a substrate may be used. In one embodiment of the method, an electroless chemical deposition process is used to deposit platinum onto the roughened and cleaned exterior wall 137 of the tubular polymer electrolyte layer 139A. The roughened and cleaned tubular ionic electroactive polymer 139A is impregnated in a complex platinum salt solution such as, for example, a solution including $[Pt(NH_3)_4]Cl_2$, for several hours at about 68° F. (20° C.). That impregnation step is followed by a reduction process using an aqueous solution containing a reducing agent such as, for example, sodium borohydride ($NaBH_4$), during which the platinum ions in the polymer are chemically reduced to metallic form at the exterior wall 137 of the tubular polymer electrolyte layer 139A.

After an additional cleaning with a reducing agent such as, for example, sulfuric acid, and deionized water, the exterior wall 137 of the now platinum-coated tubular polymer electrolyte layer 139A may be further plated with a thin layer of gold (Au) using a conventional electrochemical deposition process to increase the thickness and electrical conductivity of the presently undivided metal electrodes 112 that will be ultimately formed onto the exterior wall 137 of the tubular polymer electrolyte layer 139A. Following the gold deposition processes, the circumferentially continuous sleeve-shaped platinum and gold-coated exterior wall 137 of the tubular polymer electrolyte layer 139A can be sectored into four circumferentially-distributed and isolated metal electrodes 112 using a micro-machining process. More specifically, a computer-controlled milling machine with a micro end-mill tool may be used to mechanically remove a thin layer of platinum-gold material and, optionally, a small portion of the underlying exterior wall 137 of the tubular polymer electrolyte layer 139A at a depth of, for example, twenty to forty (20 to 40) microns. In FIG. 25, the plurality of milled grooves 136 indicate where the previously circumferentially continuous platinum-gold electrode has been sectored into plurality of metal electrodes 112, each coupled to an electrically-conductive conduit 130. FIG. 25 shows four equally sized and circumferentially distributed metal electrodes 112 centered 90° apart on the exterior wall 137 of the tubular polymer electrolyte layer 139A. The bendable portion 110 illustrated in FIG. 25 can be manipulated by selectively introducing energizing electrical signals into the metal electrodes 112 by way of the conduits 130 to provide actuation. In a final step, the finished tubular polymer electrolyte layer 139A with sectored platinum-gold electrodes 112 is cleaned and ion-exchanged into a desired cationic form (typically using lithium ions) by soaking in a metal-salt solution such as, for example, lithium chloride. During this final soaking process, the hydrogen ions (H+) in the tubular polymer electrolyte layer 139A are exchanged with lithium ions ($Li^+$).

A embodiment of a method of disposing the carbon-based electrodes 112 on the tubular polymer electrolyte layer 139A is also provided. In one example, the bendable portion 110 illustrated, e.g., in FIG. 25, is made by forming carbon-based electrodes 112 on a tubular polymer electrolyte layer 139A from a polymer, such as Nafion® using a reflow process. Since the electrode integration by the reflow process involves high temperature treatment, the exemplary example provided below herein is a wet assembly method applicable with thermally stable and non-volatile electrolytes such as ionic liquids.

In this exemplary example, the tubular polymer electrolyte layer 139A is pre-conditioned by roughening its exterior wall 137 using an abrasive (e.g., sandpaper) or by an abrasive process (e.g., sandblasting), followed by being cleaned using a reducing agent, for example, a hydrogen peroxide ($H_2O_2$) solution and/or a sulfuric acid ($H_2SO_4$) solution, and de-ionized water, but not limited to this. The roughened and cleaned tubular polymer electrolyte layer 139A is further deposition-plated with a carbon-based conductive powder, such as carbide-derived carbon, carbon nanotube, carbon aerogel, graphene, or the combination thereof.

In this exemplary example, one or more electrolytes are then incorporated in the cleaned tubular polymer electrolyte layer 139A which is first dried under vacuum (30 in Hg) at about 100 to about 140° C. for several hours to remove humidity. Thereafter, the dried tubular polymer electrolyte layer 139A is impregnated with an ionic liquid (such as EMI-BF4 or EMI-TFSI, but not limited to this) by soaking in respective ionic liquid at elevated temperature for several hours.

In this exemplary example, after being ionic liquid-impregnated, a layer of carbon-based electrodes 112 are fabricated directly onto the tubular polymer electrolyte layer 139A as follows. The conductive powder material of carbide-derived carbon (or other carbon allotrope (e.g., carbon nanotube, carbon aerogel, graphene) or the mixture thereof, but not limited to this) is dispersed in a volatile solvent of isopropanol (or the like). In an alternative embodiment, the conductive powder may further comprise fillers such as transition metal oxide powder (such as $MnO_2$ or $RuO_2$) or metal powder (such as Pt or Au). Ionic polymer (Nafion) dispersion in alcohol (or PVDF) is further added in the above-mentioned conductive powder dispersion for a binder. The mixture is homogenized by a treatment in an ultrasonic bath. The prepared conductive powder dispersion is then directly applied onto the tubular polymer electrolyte layer 139A using a conventional brush or spray coating technique to form a layer of carbon-based electrode 112. Volatile solvents are evaporated by a mild heating process after the desired thickness of the layer of carbon-based electrode 112 is achieved.

The electrical conductivity of the obtained layer of carbon-based electrode 112 is often inadequate to ensure proper electromechanical functionality for the ionic electroactive polymer actuator. In this exemplary example, the electrical conductivity of the obtained layer of carbon-based electrode 112 may be increased by further attaching Au microwire onto the surface of the obtained layer or by embedding Au wire in the obtained layer. Additionally, Au foil with a thickness of 50-150 nm may be rolled around the tubular polymer electrolyte layer 139A to serve as a highly conductive current collector.

Then, in this exemplary example, the layer of carbon-based electrode 112 is integrated with the tubular polymer electrolyte layer 139A by a reflow process. In this process, the heat-shrink polymer tube such as fluorinated ethylene-propylene (FEP) is fitted over the tubular polymer electrolyte layer 139A and heated up to a recovery temperature of the heat-shrink material. The supplied heat and applied compressive load by the heat-shrink tube may cause reflow of the ionic polymer from the tubular polymer electrolyte layer 139A, so that the layer of carbon-based electrode 112 and Au foil are thermally bonded with the tubular polymer electrolyte layer 139A. After this reflow process, the heat shrink tube is removed and the layer of carbon-based electrode 112 is sectored into four isolated carbon-based electrode sectors 112 using a micromachining process, where the computer-controlled milling machine with micro end-mill tool is used to mechanically remove a thin layer of carbon-Au composite and the tubular polymer electrolyte layer 139A at a depth of 30-50 microns. This process creates four equally sized carbon-based electrode sectors 112 at every 90° on the tubular polymer electrolyte layer 139A which can be independently controlled by electrical power to achieve two degrees-of-freedom actuation.

In another example, the bendable portion 110 illustrated, e.g., in FIG. 25, is made by forming carbon-based electrodes 112 on a tubular polymer electrolyte layer 139A from a polymer, such as Nafion® using a reflow process. This example is directed to a dry assembly applicable with both volatile (such as aqueous) and non-volatile (ionic liquids) electrolytes. The tubular polymer electrolyte layer 139A (Nafion®, DuPont) is provided and pre-conditioned as described above. To prepare a layer of carbon-based electrodes 112 onto the conditioned the tubular polymer electrolyte layer 139A, the conductive powder material of carbide-derived carbon (or other carbon allotrope, e.g., carbon nanotube, carbon aerogel, graphene, or mixtures thereof) is dispersed in a volatile solvent of isopropanol (or the like). In some embodiments, the conductive powder may further comprise transition metal oxide powders (such as $MnO_2$ or $RuO_2$, but not limited to this) or metal powder (Pt or Au, but not limited to this).

In this exemplary example, ionic polymer (Nafion) dispersion in alcohol (or PVDF) is further added in the conductive material dispersion for a binder. The mixture is homogenized by a treatment in an ultrasonic bath. Next, the prepared conductive powder dispersion is directly applied onto the tubular polymer electrolyte layer 139A using a brush or spray coating technique after being ionic liquid-impregnated. Volatile solvents are evaporated by a mild heating process until the desired thickness of the layer of carbon-based electrodes 112 is achieved.

The electrical conductivity of the obtained layer is often inadequate to ensure proper electromechanical functionality for the ionic electroactive polymer actuator. In terms of this, in this exemplary example, the electrical conductivity of the obtained layer of carbon-based electrodes 112 may be increased by attaching Au microwire onto the surface of the layer of carbon-based electrodes 112 or by embedding Au wire in the layer of carbon-based electrodes 112. Then, the layer of carbon-based electrodes 112 is integrated with the tubular polymer electrolyte layer 139A by a reflow process. In this process, the heat-shrink polymer tube such as fluorinated ethylene-propylene (FEP) is fitted over the tubular polymer electrolyte layer 139A and heated up to a recovery temperature of the heat-shrink material. The supplied heat and applied compressive load by the heat-shrink tube cause reflow of the ionic polymer, so that the layer of carbon-based electrodes 112 and Au foil are thermally bond with the tubular polymer electrolyte layer 139A. After reflow process, the heat shrink tube is removed. Additionally, the electrical conductivity of the layer of carbon-based electrodes 112 may be further increased by applying a thin layer of Pt thereon using the electroless chemical deposition and subsequent electrochemical deposition of Au.

Then, in this exemplary example, the obtained layer of carbon-based electrodes 112 is sectored into four isolated electrode sectors 112 using a micromachining process, where the computer-controlled milling machine with micro end-mill tool is used to mechanically remove a thin layer of carbon-based electrodes 112 and the tubular polymer electrolyte layer 139A at a depth of 30-50 microns. This process thus creates four equally sized electrode sectors 112 at every 90° on the surface of the tubular polymer electrolyte layer 139A which can be independently controlled by electrical power to achieve two degrees-of-freedom actuation.

Finally, in this exemplary example, the electrolyte is incorporated in the cleaned tubular polymer electrolyte membrane layer 139A. First, the tubular polymer electrolyte layer 139A is dried under vacuum (30 in Hg) at 100-140° C. for several hours to remove humidity. Thereafter, the dried tubular polymer electrolyte layer 139A is impregnated with an ionic liquid (such as EMI-BF4 or EMI-TFSI) by soaking in respective ionic liquid at elevated temperature for several hours.

In another embodiment, the flexible and elongate portion 101 of the medical device 10 (see FIGS. 1, 7, 8A, 8B, 17, 19 and 25) used to move the bendable portion 110 as described above can be formed using conventional processes known in the art. Alternately, an inner member 120 may comprise a polytetrafluoroethylene (PTFE) material, a reinforcing mesh 121 (see FIG. 19), which may be a braided wire or a coiled wire, and an outer member 150 are placed over a slender rod or a pin to be used as a mandrel. Four electrically-conductive conduits 130, which may comprise gold wires having a small diameter of, for example, 25 μm, are aligned with and secured along the length of the insulating tube using an adhesive such as, for example, an epoxy adhesive or, more specifically, a photo-activated (for example, such as a ultraviolet light-activated) adhesive. An outer member 150, which functions as a sheath or a jacket comprising a resilient material such as, for example, PEBAX®, available from Arkema of Colombes, France, is sheathed over inner member 120 and the electrically-conductive conduits 130 adhered thereto. The inner member 120, the reinforcing mesh 121 (which may be, for example, braided wire or coiled wire), the tubular insulation member 127 and the outer member 150 may be assembled using a reflow process. For subsequent coupling with the polymer electrolyte layer 139, the inner member 120 is left longer in length than the outer member 150, resulting in an extended portion of the inner member 120 that extends further beyond the distal end of the outer member 150. A polymer electrolyte layer 139 is placed over the extended portion of the inner member 120 and moved proximal to the distal end of the outer member 150 and the electrically-conductive conduits 112 are connected to the four electrodes 112 formed onto the exterior of the polymer electrolyte layer 139 using epoxy, followed by a reflow process.

The polymer electrolyte layer 139 may have an outer diameter of, for example, one millimeter (1 mm), a length of, for example, twenty millimeters (20 mm). It will be understood that the size may vary with the intended application. The polymer electrolyte layer 139 may be clamped in a vertical cantilever configuration using a custom-made connector clamp with four spring-loaded prong contacts that attach to each electrode 112 formed on the polymer electrolyte layer 139 (see FIG. 25). The free-length of the polymer electrolyte layer 139 may be up to eighteen millimeters (18 mm) or more. Electrical wires from the clamp may be connected to a custom-made controller device. A digital microscope camera such as, for example, a Plugable® USB 2.0, may be used to record images of the actuation of the polymer electrolyte layer 139.

Figure 26:
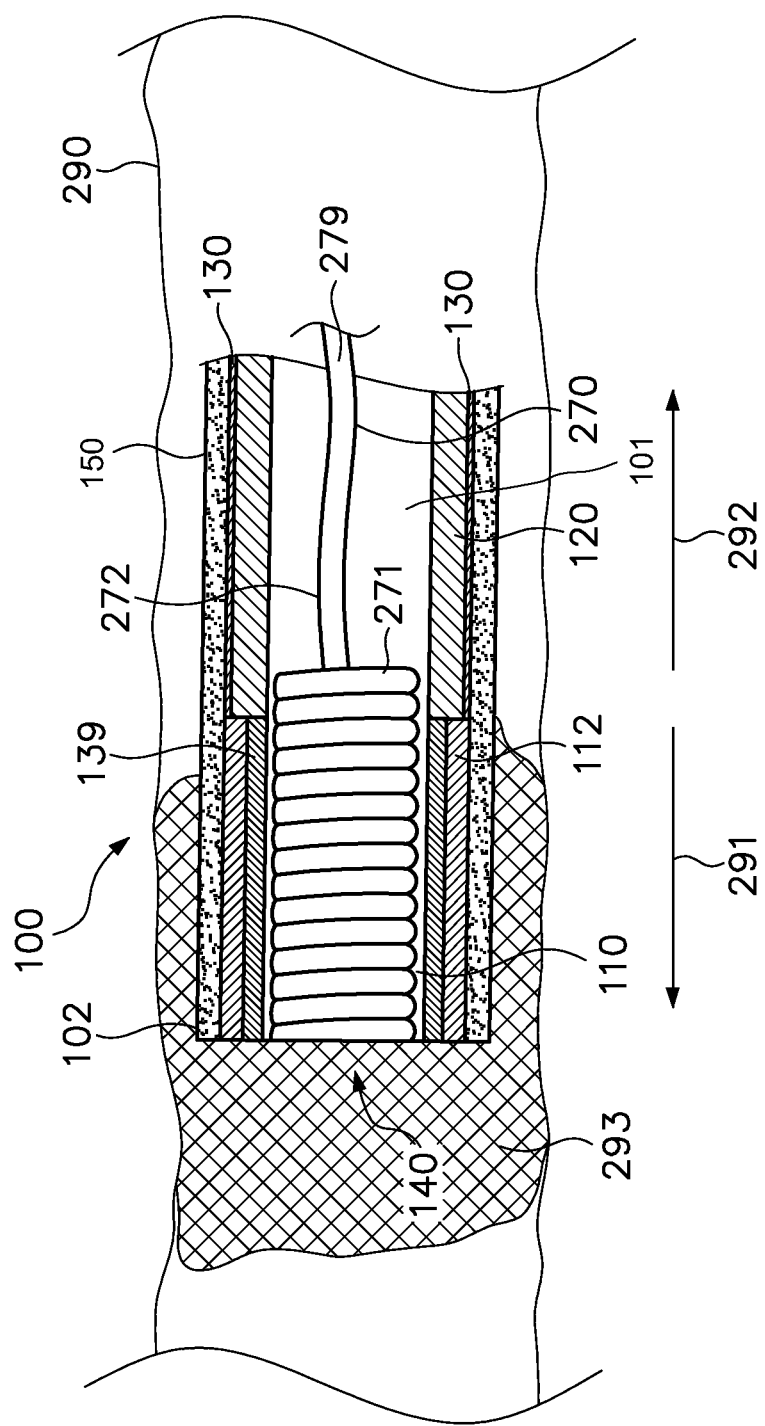
FIG. 26 is an illustration of a distal end of an actuation part of an embodiment of a medical device with a spring member, in a radially compressed configuration, coupled to a center wire advanced through the bore of the actuation part to dispose the spring element adjacent to an obstruction in a lumen.

In one embodiment of the medical device 10 (e.g., a micro-catheter), the bore 140 of the inner member 120 can be used to guide an inserted center wire 270 having an effector attached thereto to a predetermined position within a lumen of the body. For example, but not by way of limitation, FIG. 26 illustrates a distal end 102 of an actuation part 100, comprising: a radially interior bore 140, at least one polymer electrolyte layer 139, the polymer electrolyte layer 139 secured adjacent to the distal end 102 of the actuation part 100 in alignment with the inner member 120. A plurality of electrodes 112 are circumferentially distributed about the at least one polymer electrolyte layer 139 and connected to a source of electrical current through a plurality of electrically-conductive conduits 130, each having a proximal end coupled to the source of electrical current (not shown) and a distal end coupled to at least one of the plurality of electrodes 112. An elongate and flexible center wire 270 having a proximal end (not shown), a distal end 272 and a diameter 279 therebetween that is smaller than the diameter of the bore 140 of the inner member 120 of the actuation part 100 is introduced into the bore 140 of the actuation part 100 with a spring member 271 connected to the distal end 272 of the center wire 270. The spring member 271 is radially compressed to the state illustrated in FIG. 26 to enable it to be introduced, while connected to the distal end 272 of the center wire 270, into the bore 140 of the actuation part 100. The spring member 271 and the center wire 270 are pushed through the bore 140 of the actuation part 100 until the spring member 271 is in the bore 140 of the bendable portion 110 at the distal end 102 of the actuation part 100 to position the distal end 272 of the center wire 270 adjacent to the distal end 102 of the actuation part 110. The spring member 271 is a radially compressible and resilient spring member 271 coupled to the distal end 272 of the center wire 270. The spring member 271 is sized for exceeding the diameter 279 of the bore 140 of the actuation part 100 in an expanded configuration and for fitting within and being positioned in the bore 140 of the actuation part 100 by the center wire 270 in a radially compressed configuration as shown in FIG. 26. The center wire 270 can be used to advance, in the direction of arrow 291, and to position the spring member 271 immediately adjacent to the distal end 102 of the actuation part 100 with the actuation part 100 disposed within or immediately adjacent to an obstruction 293 in a blood vessel (lumen) 290 into which the actuation part 100 is introduced.

Figure 27:
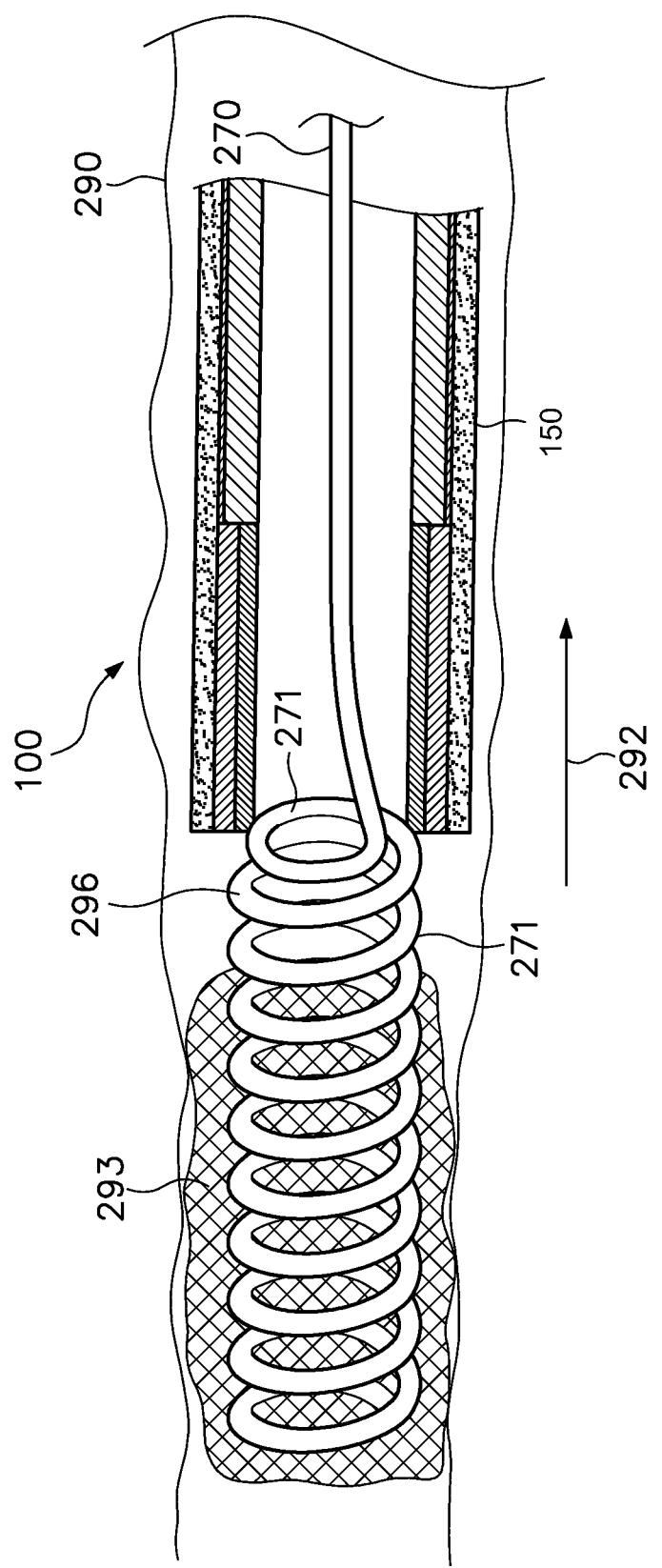
FIG. 27 is an illustration of the spring member in an expanded configuration, obtained by withdrawal of the bore of the actuation part while holding the center wire stationary, to expand and grip the obstruction for removal with the actuation part and the center wire.

The spring member 271 can be expanded to engage and grip the obstruction 293 in the blood vessel 290 by retracting the actuation part 100 in the direction of arrow 292 while maintaining the center wire 270 stationary to cause the actuation part 100 to be withdrawn from a surrounding position about the spring member 271, thereby causing the spring member 271 to be released from the radially compressed configuration to the expanded configuration shown in FIG. 27. FIG. 27 illustrates how the obstruction 293 is gripped by the expanded spring member 271, thereby allowing the obstruction 293 to be retrieved in the direction of the arrow 292 from the blood vessel 290 by retrieving the center wire 270 and the actuation part 100 together from the blood vessel 290.

Figure 28:
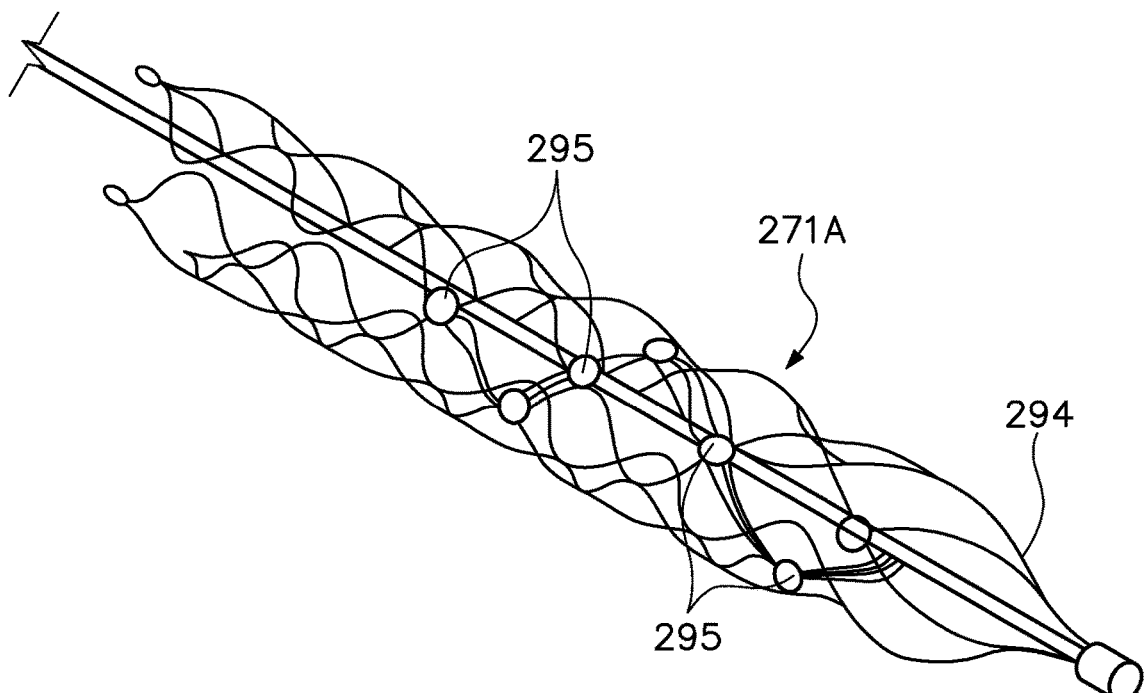
FIG. 28 is an alternative embodiment of the spring member that can be used to implement the method illustrated by FIGS. 26 and 27.

In one embodiment, the spring member 271 is a coil spring having a plurality of coils 296 in a series as shown in FIG. 26. In another embodiment, the spring member 271 includes a plurality of corrugated or sinusoidally shaped wires 294 as shown in FIG. 28, each coupled at the apexes of the waves or peaks 295 to the apexes of the waves or peaks 295 of an adjacent wire 294 to form a generally tubular or cylindrically shaped spring assembly 271A, as shown in FIG. 28. It will be understood that expandable spring elements of this type generally elongate as they radially expand from a radially compressed configuration to a radially expanded configuration.

Figure 29:
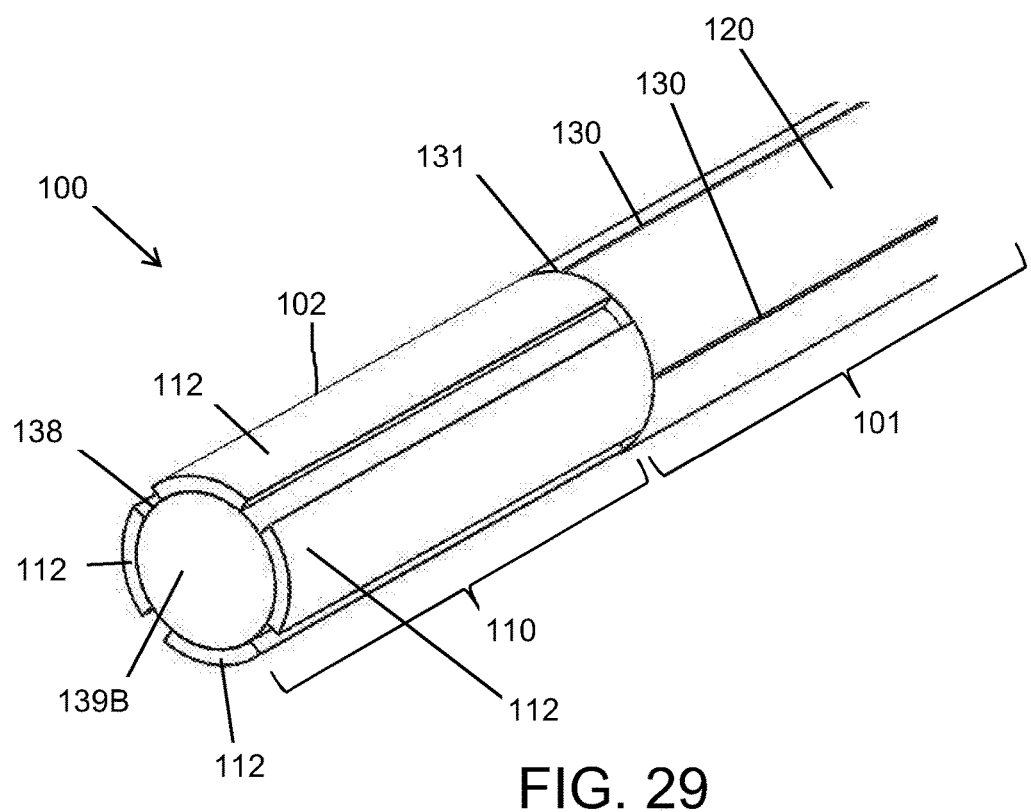
FIG. 29 is a perspective view of the elongate, flexible portion and a bendable portion disposed at the distal end of the actuation part of another embodiment of the medical device of FIG. 1.

FIG. 29 is a perspective view of the elongate, flexible portion 101 and a bendable portion 110 disposed at the distal end 102 of the actuation part 100 of another embodiment of the medical device 10 of FIG. 1. Unlike a micro-catheter (e.g., the medical device shown in FIGS. 2-4B), FIG. 29 illustrates a medical device 10 without an interior bore that may, for example, be a guidewire. The bendable portion 110 of the actuation part 100 includes an ionic electroactive polymer actuator comprising a polymer electrolyte body 139B disposed adjacent to the inner member 120 of the elongate, flexible portion 101 and centrally to an angularly-distributed plurality of energizable electrodes 112. Each of the plurality of electrodes 112 that surrounds the exterior wall 138 of the polymer electrolyte body 139B is connected to a distal end 131 of an electrically-conductive conduit 130 through which an electrical signal or current may be supplied to the connected electrode 112. To increase the function of the guidewire (e.g., support, steering, tracking, visibility, tactile feedback, lubricity, and/or trackability), it will be understood that the elongate, flexible portion 101 may optionally further comprise a protective outer member (not shown, such as a cover and/or coating) to surround the inner member 120 while a helical coil may be optionally further covered over the protective outer member. The bendable portion 110 of FIG. 29 is illustrated in the straight mode, which can be selectively and controllably deformed to a bent mode by selective energization of one or more of the plurality of electrodes 112, as explained above.

Figure 30:
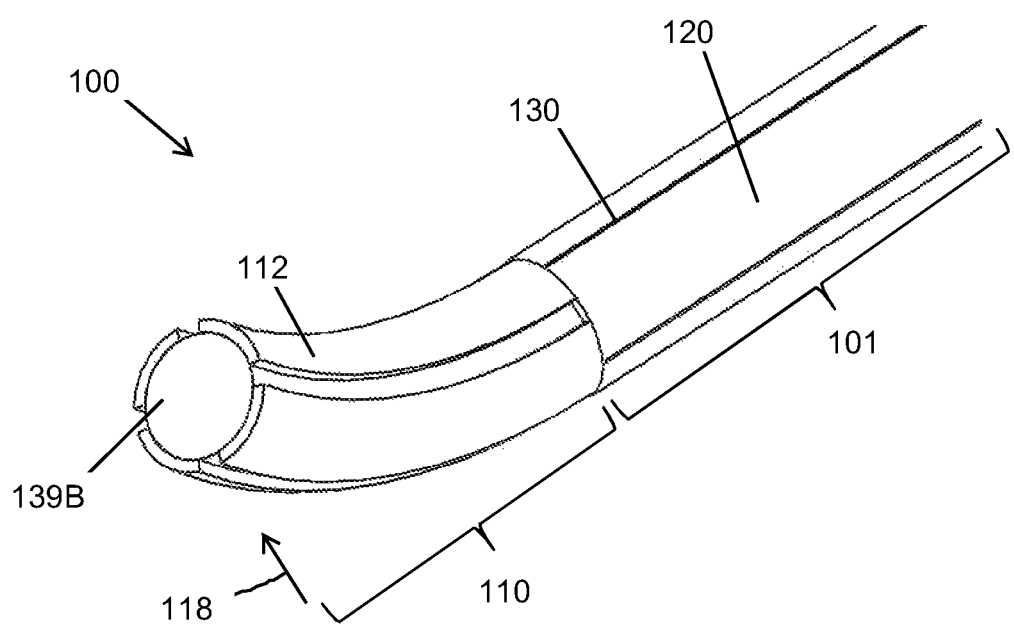
FIG. 30 is the perspective view of the distal, bendable portion at the distal end of the actuation part of FIG. 29 illustrating the bending mode.

FIG. 30 is the perspective view of the bendable portion 110 at the distal end 102 of the actuation part 100 of FIG. 29 illustrating the deformed or bending mode. The bendable portion 110 of the actuation part 100 of the medical device 10 is illustrated as having been actuated from the straight mode shown in FIG. 29 to the deformed or bent mode of FIG. 30 through the selective application of electrical signals to selected electrodes 112 to deform the polymer electrolyte body 139B. The energization of selected electrodes 112 causes the bendable portion 110 to be deformed from the straight mode to the bent mode by application of an external force indicated by arrow 118. It will be understood that the medical device 10 in FIGS. 29 and 30, as a guidewire, may be used to navigate vessels to reach a lesion or vessel segment. Once the bendable portion 110 of the medical device 10 arrives at its destination, it acts as a guide so that larger catheters having a bore for passing through the guidewire can rapidly follow for easier delivery to the treatment site.

In some embodiments a medical device 10 comprises an elongate flexible portion 101 that comprises an outer tubular layer; an inner tubular layer, wherein a space is formed between the outer tubular layer and the inner tubular layer; a support layer positioned within the space, wherein the support layer comprises: a braided wire, a coil or the combination thereof being covered on an outer surface of the inner tubular layer; a bendable portion 110 provided at a distal end 102 of the elongate flexible portion 101, comprising an ionic electroactive polymer layer, that is bendable in a desired direction in response to an applied electrical signal, wherein the ionic electroactive polymer layer comprises: an ionomer tubular layer comprising an electrolyte and a plurality of electrodes placed in contact with the ionomer tubular layer; and a transmitting member which comprises a plurality of wires respectively arranged along the space of the flexible elongate member and electrically connecting the electrodes. In some embodiments the wires further comprise an insulating layer.

In some embodiments a medical device comprises a flexible elongated member; and a bending member provided at a distal end of the flexible elongated member, made from an electroactive polymer, and bendable in a desired direction in response to an applied electrical signal, wherein the bending member comprises a main body made of an ionic electroactive polymer and a plurality of electrodes placed in contact with the main body. In some embodiments the outer surfaces of the flexible elongated member and the bending member are coated with a hydrophilic material.

In some embodiments the bendable portion 110 further comprises an encapsulation layer covering the bendable portion 110. In some embodiments the flexible inner member 120 and the bendable portion 110 are coated with a hydrophilic material and/or the bendable portion 110 further comprises a tubular insulation member 127 between the reinforcing mesh and electrically-conducting conduit 130. In some embodiments the outer tubular member further comprises a plurality of insulation layers. In some embodiments each wire passes through each insulation layer respectively. In some embodiments, the electrodes are selected from the group consisting of Pt electrodes, Au electrodes, carbon electrodes, or the combination thereof. In some embodiments the carbon electrodes are selected from the group consisting of carbide-derived carbon, carbon nanotube, graphene, a composite of carbide-derived carbon and ionomer, and a composite of carbon nanotube and ionomer. In some embodiments, the electrodes are symmetrically arranged along the circumference of the ionic electroactive polymer layer and in some embodiments there are four electrodes.

In some embodiments the device further comprises an electrical controller that transmits electrical signals through the electrically-conducting conduit 130 to the electrodes and inducing bending of the bendable portion 110. In some embodiments the electrical controller is configured to generate electrical signals in response to user manipulation such that the bendable portion 110 responds to user manipulation. In some embodiments the medical device is a catheter or a guide wire.

In some embodiments, the device further comprises a drive assembly configured to move the flexible inner member 120 lengthwise. In some embodiments the drive assembly is configured to come into partial contact with the surface of the flexible inner member 120 using a friction-based mechanism that acts between the drive assembly and the surface.

In some embodiments, the drive assembly comprises at least a pair of rotary drive members 330a, 330b and a motor 310 that operates the rotary drive members 330a, 330b. The flexible inner member 120 is arranged to pass between the pair of rotary drive members 330a, 330b and is moved along lengthwise with the operation of the rotary drive members 330a, 330b.

In some embodiments the pair of rotary drive members 330a, 330b comprise spools rotatably placed, and the flexible inner member 120 is placed to be movable between the pair of spools by the rotation of the spools. In some embodiments the drive system comprises a pair of belts that are arranged on either side of the flexible inner member 120, and the flexible inner member 120 is placed to be movable between the pair of belts by the operation of the belts.

In some embodiments the medical device further comprises: a upper case portion 210 that accommodates the flexible inner member 120; and a lower case portion 210 that is detachable from the upper case portion 210, wherein some or all parts of the drive assembly and the electrical control member are placed in the lower case portion 210. In some embodiments, the moving parts are arranged in the upper case portion 210. In some embodiments the drive assembly further comprises: a current distributor 410 electrically connecting the wires and being inside the upper case portion 210; an interlocking part for transmitting driving force from the motor 310 to the moving parts, being provided in the lower case portion 210; and an interface device 420 being connected to the electrical controller and provided in the lower case portion 210. In some embodiments the upper case portion 210 and the lower case portion 210 are fastened together, the worm gear 320 of the lower case portion 210 is connected to the moving parts of the upper case portion 210 to transmit the driving force, and the interface device 420 of the lower case portion 210 is connected to the current distributor 410 of the upper case portion 210 to transmit electrical signals from the electrical controller to the wires. Some embodiments further comprise a sensing member that senses an electrical signal at the bendable portion 110 when a deformation occurs to the bending member. In some embodiments the bendable sensing member 117 is configured to determine whether an external force is applied to the bendable portion 110 or not, considering an electrical signal generated by bending control from the electrical control member, out of electrical signals sensed at the bending member. Some embodiments further comprise a master controller that remotely instructs the electrical controller and the drive assembly. In some embodiments the medical device is a catheter in which the flexible inner member 120 and the bendable portion 110 have a conduit inside and in some embodiments the medical device is a guide wire. In some embodiments the bendable portion 110 further comprises an encapsulation layer being covered the bending member. In some embodiments the outer surfaces of the flexible inner member 120 and the bendable portion 110 are coated with a hydrophilic material. In some embodiments the medical device the wires further comprise an insulation layer. In some embodiments the bendable portion 110 further comprises a tubular insulation member 127 between the reinforcing mesh and electrically-conducting conduit 130. In some embodiments the outer tubular member further comprises a plurality of insulation layers. In some embodiments each wire passes through each insulation layer respectively. In some embodiments the electrodes are Pt electrodes, Au electrodes, carbon electrodes or the combination thereof. In some embodiments the ionic electroactive polymer layer further comprises carbon-based electrodes consisting of carbide-derived carbon, carbon nanotube, graphene, a composite of carbide-derived carbon and ionomer, and a composite of carbon nanotube and ionomer. In some embodiments the electrodes are symmetrically arranged along the circumference of the ionic electroactive polymer layer. In some embodiments there are four electrodes.

In some embodiments the electrical controller is configured to generate electrical signals, and the drive assembly is configured to move the flexible inner member 120 in response to user manipulation.

In some embodiments a system for remotely controlling the positioning of a medical device within the body of a patient comprises: a remote control member that comprises a master controller that remotely instructs the medical device to be positioned within the body of the patient; and a local communication member configured to communicate a control signal between the remote control member and the medical device. In some embodiments the communication member wirelessly transmits information using Bluetooth or wireless 802.11 communication over the internet. In some embodiments the system drive assembly is configured to come into partial contact with the surface of the flexible inner member 120 and move the flexible inner member 120 based on a friction-based mechanism acting between the drive assembly and the surface. In some embodiments the system drive assembly comprises at least a pair of rotary drive members 330a, 330b and a motor 310 that operates the rotary drive members 330a, 330b, and the flexible inner member 120 is arranged to pass through between the pair of rotary drive members 330a, 330b and moves lengthwise along with the operation of the rotary drive members 330a, 330b.

In some embodiments of the system the pair of rotary drive members 330a, 330b comprises a pair of spools that are rotatably placed, and the flexible inner member 120 is placed to be movable between the pair of spools by the rotation of the spools. In some embodiments the system the pair of rotary drive members 330a, 330b comprises a pair of belts that are arranged on either side of the flexible inner member 120, and the flexible inner member 120 is placed to be movable between the pair of belts by the operation of the belts. In some embodiments the system further comprises an upper case portion 210 that accommodates a tubular flexible inner member 120; and a lower case portion 210 that is placed to be detachable from the upper case portion 210, wherein some or all parts of the drive assembly and the electrical controller are placed in the lower case portion 210. In some embodiments the system the rotary drive members 330a, 330b are arranged in the upper case portion 210. In some embodiments the system the drive assembly further comprises: a current distributor 410 electrically connecting the wires and being inside the upper case portion 210; a worm gear 320 for transmitting driving force from the motor 310 to the moving parts, being provided in the lower case portion 210; and a interface device 420 being connected to the electrical controller and provided in the seconding module. In some embodiments of the system the upper case portion 210 and the lower case portion 210 are fastened together, the worm gear 320 of the lower case portion 210 is connected to the rotary drive members 330a, 330b of the upper case portion 210 to transmit the driving force, and the interface device 420 of the lower case portion 210 is connected to the current distributor 410 of the upper case portion 210 to transmit electrical signals from the electrical controller/processor to the wires.

In some embodiments the system further comprises a sensing member 117 that senses an electrical signal at the bendable portion 110 when a deformation occurs to the bending member. In some embodiments the sensing member 117 is configured to determine whether an external force is applied to the bendable portion 110 or not, considering an electrical signal generated by bending control from the electrical control member, out of electrical signals sensed at the bending member. In some embodiments the system further comprises a master controller that remotely instructs the electrical controller and the drive assembly. In some embodiments of the system the medical device is a catheter in which the flexible inner member 120 and the bendable portion 110 have a conduit inside. In some embodiments the medical device is a guide wire. In some embodiments of the system the bendable portion 110 further comprises an encapsulation layer being covered the bending member. In some embodiments of the system the outer surfaces of the flexible inner member 120 and the bendable portion 110 are coated with a hydrophilic material. In some embodiments the system the wires further comprise an insulation layer. In some embodiments of the system the bendable portion 110 further comprises a tubular insulation member 127 between the reinforcing mesh and electrically-conducting conduit 130. In some embodiments of the system the outer tubular member further comprises a plurality of insulation layers. In some embodiments of the system each wire passes through each insulation layer respectively. In some embodiments of the system the electrodes are Pt electrodes, Au electrodes, carbon electrodes or the combination thereof. In some embodiments of the system the ionic electroactive polymer layer further comprises carbon-based electrodes consisting of carbide-derived carbon, carbon nanotube, graphene, a composite of carbide-derived carbon and ionomer, and a composite of carbon nanotube and ionomer. In some embodiments of the system the electrodes are symmetrically arranged along the circumference of the ionic electroactive polymer layer. In some embodiments of the system there are four electrodes. In some embodiments of the system the electrical controller is configured to generate electrical signals, and the drive assembly is configured to move the flexible inner member 120 in response to user manipulation. In some embodiments, the inner member 120 is tubular. In some embodiments the ionomer tubular layer comprising an electrolyte is a polymer electrolyte layer 139. In some embodiments the ionic electroactive polymer layer comprises a polymer electrolyte layer 139 and a plurality of electrodes 112.

Certain embodiments include methods for preparing the bendable portion 110 of a device comprising the steps of: providing a polymer electrolyte layer 139 and a mandrel against an inner surface of the ionomer tube; forming a carbon electrode layer on an outer surface of the polymer electrolyte layer 139, wherein a mixture of a carbon-based conductive power is applied onto the outer surface of the polymer electrolyte layer 139; attaching an electrically-conducting conduit 130 on the carbon electrode layer, wherein the electrically-conducting conduit 130 comprises a plurality of wires respectively being electrically connected to the carbon electrode layer; providing a heat-shrink tubular layer covered around the carbon electrode layer and the polymer electrolyte layer 139; heating the heat-shrink polymer to cause reflow of the ionic electroactive polymer from the polymer electrolyte layer 139, so that the carbon electrode layer and the polymer electrolyte layer 139 are thermally bonded; and removing the heat-shrink tubular layer and the mandrel to form the bending member.

In some embodiments the method further comprises the steps of: forming a platinum layer on the carbon electrode layer; forming a gold layer on the platinum layer; micromachining the carbon electrode layer to be sectored into a plurality of carbon electrodes; and incorporating electrolytes into the bending member, wherein the bendable portion 110 is dried to remove humidity and impregnated with an ionic liquid. In some embodiments the platinum layer is disposed on the carbon electrode layer using electroless chemical deposition. In some embodiments the gold layer is disposed on the platinum layer using electrochemical deposition. In some embodiments a computer-controlled milling machine with a micro end-mill tool is used to mechanically remove a thin layer from the carbon electrode layer and the polymer electrolyte layer 139 at a predetermined depth. In some embodiments the predetermined depth is about 30 to about 50 microns.

In some embodiments the method for preparing a bendable portion 110 of a medical device, comprises steps of: providing a mandrel against an outer surface of a polymer electrolyte layer 139 comprising at least a ionic electroactive polymer; incorporating electrolytes into the bending member, wherein the bendable portion 110 is dried to remove humidity and impregnated with an ionic liquid; forming a carbon electrode layer on the polymer electrolyte layer 139, wherein at least a carbon-based conductive power is dispersed in a volatile solvent to form an a mixture of the carbon electrode and the mixture is applied onto the polymer electrolyte layer 139 to form a carbon electrode layer; attaching an electrically-conducting conduit 130 on the carbon electrode layer, wherein the electrically-conducting conduit 130 comprises a plurality of wires respectively being electrically connected to the carbon electrode layer; disposing a heat-shrink polymer around the carbon electrode layer and the polymer electrolyte layer 139; heating the heat-shrink polymer, the carbon electrode layer and the polymer electrolyte layer 139 to cause reflow of the ionic electroactive polymer from the polymer electrolyte layer 139, whereby the carbon electrode and the polymer electrolyte layer 139 are thermally bonded; and removing the first heat shrink material and the mandrel to form the bending member. Some embodiments further comprise the steps of: micromachining the carbon electrode layer to be sectored into a plurality of carbon electrodes. While in other embodiments a computer-controlled milling machine with micro end-mill tool is used to mechanically remove a thin layer from the carbon electrode layer and the polymer electrolyte layer 139 at a predetermined depth, for example a predetermined depth is about 30 to about 50 microns.

In some embodiments the bendable portion 110 is dried to remove humidity, and then is impregnated with an ionic liquid. In some embodiments the drying occurs under vacuum at about 100 to about 140° C. In some embodiments the ionic liquid is 1-ethyl-3-methylimidazolium tetrafluoroborate (EMI-BF4), 1-Ethyl-3-methylimidazolium bis(trifluoromethylsulfonyl)imide (EMI-TFSI) or a combination thereof. In some embodiments the ionic electroactive polymer is an ionic polymer-metal composite (IPMC). In some embodiments the ionic polymer-metal composite (IPMC) is Nafion. In some embodiments of the method the carbon-based conductive powder is selected from carbide-derived carbon, carbon nanotube, carbon aerogel, graphene, or the combination thereof. In some embodiments the carbon-based conductive powder further comprises: transition metal oxide powder or metal powder or the combination thereof. In some embodiments the transition metal oxide powder comprises: $MnO_2$, $RuO_2$ or the combination thereof. In some embodiments the metal powder comprises: Pt, Au or the combination thereof. In some embodiments attaching a electrically-conducting conduit 130 on the carbon electrode layer further comprises a step of attaching a gold foil layer covered the polymer electrolyte layer 139.

In some embodiments of the method at least one carbon-based conductive powder is dispersed in a volatile solvent to form a mixture that is applied onto outer surface of the polymer electrolyte layer 139 to form a carbon electrode layer. In some embodiments the mixture is applied onto the polymer electrolyte layer 139 using brush coating or spray coating to form a carbon electrode layer. In some embodiments the volatile solvent is isopropanol. In some embodiments the polymer electrolyte layer 139 is pretreated to roughen and clean the outer surface thereof. In some embodiments the outer surface of the polymer electrolyte layer 139 is roughened by a mechanical treatment, such as, but not limited to sandpapering or sandblasting. In some embodiments wherein the outer surface of the polymer electrolyte layer 139 is cleaned with hydrogen peroxide ($H_2O_2$), sulfuric acid ($H_2SO_4$) solutions, and de-ionized (DI) water.

Some embodiments provide a method for preparing a polymer electrolyte layer 139 in tubular shape for a bendable portion 110 of a device, comprising steps of: providing a liquid dispersion of a base material that is selected from the group consisting of ionic polymer, fluoropolymer and intrinsically conductive polymer; casting the liquid dispersion on a substrate; forming a polymer film on the substrate by curing the liquid dispersion; providing a mandrel, wherein the mandrel is further rolled around with the polymer film being removed from the substrate; and providing a heat-shrink tube to cover the rolled polymer film around the mandrel, and heating the heat-shrink tube to cause reflow of the rolled polymer film to form a polymer electrolyte layer 139. In some embodiments the ionic polymer comprises Nafion or Flemion. In some embodiments the fluoropolymer comprises Poly[(vinylidene difluoride)-co-(chlorotrifluoroethylene) (PVDF) or the co-polymer thereof. In some embodiments the co-polymer comprises Poly(vinylidene difluoride-co-chlorotrifluoroethylene) (P(VDF-CTFE)) or Poly(vinylidene fluoride-co-hexafluoropropylene) (P(VDF-HFP)).

In some embodiments the intrinsically conductive polymer comprises: polyaniline (PANI), polypyrrole (Ppy), poly (3,4-ethylenedioxythiophene) (PEDOT), or poly(p-phenylene sulfide) (PPS). In some embodiments the bendable portion 110 is an electroactive polymer actuator. In some embodiments the medical device is a catheter. In some embodiments the substrate is a PTFE plate or a glass plate. In some embodiments the heat-shrink tube is a fluorinated ethylene-propylene (FEP) tube. In some embodiments the heat-shrink tube is heated at a temperature of 200 to 230° C.

It is to be noted that various modifications or alterations can be made to the above-described exemplary embodi-

We claim:
1. A medical device, comprising:
   an elongate, flexible portion having a distal end and a proximal end, an outer member having a continuous outer surface over its circumference and length and an inner surface, and an inner member having a continuous outer surface over its circumference and length and an inner surface;
   at least one ionic electroactive polymer actuator, the actuator comprising:
   at least one polymer electrolyte layer secured adjacent to the distal end of the elongate, flexible portion; and
   a plurality of electrodes circumferentially distributed about the at least one polymer electrolyte layer; and
   a plurality of electrically-conductive conduits, each having a proximal end disposed adjacent to the proximal end of the elongate flexible portion and a distal end coupled to at least one of the plurality of electrodes wherein the conduits extend within the elongate flexible portion between the outer surface of the outer member and the inner surface of the inner member;
   wherein the at least one polymer electrolyte layer deforms asymmetrically in response to the application of an electrical signal through at least one of the plurality of electrically-conductive conduits to at least one of the plurality of electrodes.

2. The medical device of claim 1, wherein each of the plurality of electrodes comprises one of platinum, gold, carbon, or a combination of two or more of platinum, gold and carbon.

3. The medical device of claim 1, wherein each of the plurality of electrodes comprises one of carbide-derived carbon, carbon nanotube, graphene, a composite of carbide-derived carbon and ionomer, or a composite of carbon nanotube and ionomer.

4. The medical device of claim 1, wherein the plurality of electrodes are circumferentially distributed about the at least one polymer electrolyte layer by equal angles about their circumferential centers.

5. The medical device of claim 1, wherein wherein the conduits extend within the elongate flexible portion between the inner surface of the outer member and the outer surface of the inner member.

6. The medical device of claim 1, wherein the inner member and the at least one polymer electrolyte layer further form a bore, and the polymer electrolyte layer is secured adjacent to the distal end of the inner member with the bore of the polymer electrolyte layer aligned with the bore of the inner member.

7. The medical device of claim 1, wherein each of the electrically-conductive conduits is electrically isolated from one another.

8. The medical device of claim 5, wherein the outer member comprises a plurality of lumens embedded within the outer member, each lumen having an interior space extending longitudinally along the outer member through which each of the plurality of electrically-conductive conduits pass.

9. The medical device of claim 1, wherein each of the plurality of electrically-conductive conduits further comprises an insulation coating covered thereon.

10. The medical device of claim 5, further comprising at least one wire helically or interweavingly wrapped around the inner member intermediate the proximal end and the distal end.

11. The medical device of claim 10, further comprising an insulation member surrounding the at least one wire.

12. The medical device of claim 1, further comprising an electrical controller provided at the proximal end of the elongate, flexible portion and electrically connected to the electrically-conductive conduits, the electrical controller configured to selectively control the electrical charge on the electrically-conducting conduits and imparted thereby to the plurality of electrodes to manipulate the at least one ionic electroactive polymer actuator of the medical device.

13. The medical device of claim 12, further comprising a master controller having a manipulatable control member for selecting the electrical charge on the at least one ionic electroactive polymer actuator and thereby provide at least one degree of freedom of bending of the elongate flexible member.

14. The medical device of claim 12, further comprising a drive assembly configured to move the medical device lengthwise, the drive assembly including:
   a first rotary drive member with a gripping surface;
   an adjacent second rotary drive member with a gripping surface disposed proximal to the gripping surface of the first rotary drive member; and
   at least one electrically powered motor coupled to controllably rotate at least one of the first rotary drive member and the second rotary drive member;
   wherein the medical device is disposed intermediate of, and engaged by, the gripping surface of the first rotary drive member and the gripping surface of the adjacent second rotary drive member so that rotation of one of the first rotary drive member and the second rotary drive member axially moves the medical device.

15. The medical device of claim 14, wherein clockwise rotation of the first rotary drive member and counterclockwise rotation of the adjacent second rotary drive member moves the medical device in a first direction; and counterclockwise rotation of the first rotary drive member and clockwise rotation of the adjacent second rotary drive member moves the medical device in a second direction opposite to the first direction.

16. The medical device of claim 14, further comprising a master controller having a manipulatable control member for inputting a bending control signal to the electrical controller to set the charge on the at least one ionic electroactive polymer actuator for providing at least one degree of freedom of bending through the electrical controller, and for inputting advance and retract control signals to the drive assembly for providing one degree of freedom of translation.

17. The medical device of claim 14, further comprising a case that includes:
   a first portion having a sealed interior portion containing the first rotary drive member, the second rotary drive member, a proximal port through which the medical device passes, a distal port through which the medical device passes, and an interior cavity for storing windings of the medical device; and
   a second portion supporting the motor.

18. The medical device of claim 17, wherein the second portion of the case and the first portion of the case are adapted for being coupled one to the other to operatively engage the motor with at least one of the first rotary member and the second rotary member.

19. The medical device of claim 1, further comprising a sensing member electrically connected to the plurality of electrodes to sense changes in the electrical signal at each of the plurality of electrodes.

20. The medical device of claim 16, further comprising:
a transmitter coupled to the master controller configured to transmit a signal corresponding to the manipulation of the master controller; and
a receiver electrically connected to the drive assembly and the electrical controller configured to receive the signal transmitted by the transmitter to the drive assembly, or the electrical controller, or to the drive assembly and the electrical controller to correspond to the manipulation of the master controller.

* * * * *